(12) United States Patent
Bridges et al.

(10) Patent No.: US 6,344,459 B1
(45) Date of Patent: *Feb. 5, 2002

(54) IRREVERSIBLE INHIBITORS OF TYROSINE KINASES

(75) Inventors: Alexander James Bridges, Saline, MI (US); William Alexander Denny, Auckland (NZ); Ellen Myra Dobrusin, Ann Arbor, MI (US); Annette Marian Doherty, Paris (FR); David William Fry, Ypsilanti, MI (US); Dennis Joseph McNamara; Howard Daniel Hollis Showalter, both of Ann Arbor, MI (US); Jeffrey B. Smaill, Auckland (NZ); Hairong Zhou, Ann Arbor, MI (US)

(73) Assignee: Warner-Lambert Company, Morris Plains, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 150 days.

(21) Appl. No.: 09/155,501

(22) PCT Filed: Apr. 8, 1997

(86) PCT No.: PCT/US97/05778

§ 371 Date: Jun. 8, 1999

§ 102(e) Date: Jun. 8, 1999

(87) PCT Pub. No.: WO97/38983

PCT Pub. Date: Oct. 23, 1997

Related U.S. Application Data

(60) Provisional application No. 60/015,351, filed on Apr. 12, 1996.

(51) Int. Cl.$^7$ ................ A61K 31/517; C07D 239/72
(52) U.S. Cl. ................ 514/259; 514/258; 544/293; 544/283
(58) Field of Search ................ 514/259, 258; 544/284, 293, 283

(56) References Cited

U.S. PATENT DOCUMENTS

| | | | |
|---|---|---|---|
| 5,321,030 A | 6/1994 | Kaddurah-Daouk et al. | 514/275 |
| 5,457,105 A | 10/1995 | Barker | 514/234.5 |
| 5,475,001 A | 12/1995 | Barker | 514/258 |
| 5,654,307 A | 8/1997 | Bridges et al. | 514/258 |
| 5,679,683 A | 10/1997 | Bridges et al. | 514/267 |
| 5,760,041 A | 6/1998 | Wissner et al. | 514/259 |

FOREIGN PATENT DOCUMENTS

| | | |
|---|---|---|
| EP | 0520722 A1 | 12/1992 |
| EP | 0566226 A1 | 10/1993 |
| EP | 0602851 A1 | 6/1994 |
| EP | 566226 * | 7/1994 |
| EP | 607439 * | 7/1994 |
| EP | 0635498 A1 | 1/1995 |
| EP | 0635507 A1 | 1/1995 |
| EP | 0682027 A1 | 11/1995 |
| EP | 0787722 A1 | 8/1997 |
| TW | 270117 | 7/1983 |
| WO | 92/20642 | 11/1992 |
| WO | 95/03283 | 2/1995 |
| WO | 95/15758 | 6/1995 |
| WO | 95/19774 | 7/1995 |
| WO | 95/19970 | 7/1995 |
| WO | 95/23141 | 8/1995 |
| WO | 95/24190 | 9/1995 |
| WO | 96/07657 | 3/1996 |
| WO | 96/09294 | 3/1996 |
| WO | 96/15118 | 5/1996 |
| WO | 96/29331 | 9/1996 |
| WO | 96/30347 | 10/1996 |
| WO | 96/33977 | 10/1996 |
| WO | 96/33978 | 10/1996 |
| WO | 96/33979 | 10/1996 |
| WO | 96/33980 | 10/1996 |
| WO | 96/33981 | 10/1996 |

(List continued on next page.)

OTHER PUBLICATIONS

Thompson, A. M., et al., "Tyrosine Kinase Inhibitors. 7. 7–Amino–4–(phenylamino)–and 7–Amino–4–[(phenylmethyl)–amino]pyrido[4,3–d]pyrimidines: A New Class of Inhibitors of the Tyrosine Kinase Activity of the Epidermal Growth Factor Receptor," *Journal of Medicinal Chemistry*, 1995, vol. 38, pp. 3780–3788.

Rewcastle, G. W., et al, "Tyrosine Kinase Inhibitors. 5. Synthesis and Structure–Activity Relationships for 4–[(Phenylmethyl)amino]–and 4–(Phenylamino)quinazolines as Potent Adenosine 5'–Triphosphate Binding Site Inhibitors of the Tyrosine Kinase Domain of the Epidermal Growth Factor Receptor," *Journal of Medicinal Chemistry*, 1995, vol. 38, pp. 3482–3487.

Wilson, T., *Sugen, Inc., Company Report*, Nov. 7, 1994, pp. 1–20.

Primary Examiner—Mukund J. Shah
Assistant Examiner—Sudhaker B. Patel
(74) Attorney, Agent, or Firm—Todd M Crissey; Linda A. Vag; Suzanne M. Harvey

(57) ABSTRACT

The present invention provides compounds that are irreversible inhibitors of tyrosine kinases. Also provided is a method of treating cancer, restenosis, atherosclerosis, endometriosis, and psoriasis and a pharmaceutical composition that comprises a compound that is an irreversible inhibitor of tyrosine kinases.

17 Claims, No Drawings

FOREIGN PATENT DOCUMENTS

| | | |
|---|---|---|
| WO | 96/39145 | 12/1996 |
| WO | 96/40142 | 12/1996 |
| WO | 96/40648 | 12/1996 |
| WO | 97/03069 | 1/1997 |
| WO | 97/13760 | 4/1997 |
| WO | 97/13771 | 4/1997 |
| WO | 97/17329 | 5/1997 |
| WO | 97/18212 | 5/1997 |
| WO | 97/22596 | 6/1997 |
| WO | 97/30034 | 8/1997 |
| WO | 97/30035 | 8/1997 |
| WO | 99/09016 | 2/1999 |

* cited by examiner

IRREVERSIBLE INHIBITORS OF TYROSINE KINASES

This application is a 35 USC 371 filing of PCT/US97/05778, filed on Apr. 8, 1997. This application claim the benefit of U.S. Provisional No. 60/015,351 filed Apr. 12, 1996.

FIELD OF THE INVENTION

This invention relates to compounds that are irreversible inhibitors of tyrosine kinases. This invention also relates to a method of treating cancer, atherosclerosis, restenosis, endometriosis, and psoriasis, and to a pharmaceutical composition that comprises a compound that is an irreversible inhibitor of tyrosine kinases.

BACKGROUND OF THE INVENTION

Cancer has been viewed as a disease of the intracellular signalling system, or signal transduction mechanism. Cells receive instructions from many extracellular sources, instructing them to either proliferate or not to proliferate. The purpose of the signal transduction system is to receive these and other signals at the cell surface, get them into the cell, and then pass the signals on to the nucleus, the cytoskeleton, and transport and protein synthesis machinery.

The most common cause of cancer is a series of defects, either in these proteins, when they are mutated, or in the regulation of the quantity of the protein in the cell such that it is over or under produced. Most often, there are key lesions in the cell which lead to a constitutive state whereby the cell nucleus receives a signal to proliferate, when this signal is not actually present. This can occur through a variety of mechanisms. Sometimes the cell may start to produce an authentic growth factor for its own receptors when it should not, the so-called autocrine loop mechanism. Mutations to the cell surface receptors, which usually signal into the cell by means of tyrosine kinases, can lead to activation of the kinase in the absence of ligand, and passing of a signal which is not really there. Alternatively, many surface kinases can be overexpressed on the cell surface leading to an inappropriately strong response to a weak signal. There are many levels inside the cell at which mutation or overexpression can lead to the same spurious signal arising in the cell, and there are many other kinds of signalling defects involved in cancer. This invention touches upon cancers which are driven by the three mechanisms just described, and which involve cell surface receptors of the epidermal growth factor receptor tyrosine kinase family (EGFR). This family consists of the EGF receptor (also known as Erb-B1), the Erb-B2 receptor, and its constitutively active oncoprotein mutant Neu, the Erb-B3 receptor and the Erb-B4 receptor. Additionally, other biological processes driven through members of the EGF family of receptors can also be treated by compounds of the invention described below.

The EGFR has as its two most important ligands Epidermal Growth Factor (EGF) and Transforming Growth Factor alpha (TGFalpha). The receptors appear to have only minor functions in adult humans, but are apparently implicated in the disease process of a large portion of all cancers, especially colon and breast cancer. The closely related Erb-B2, Erb-B3, and Erb-B4 receptors have a family of Heregulins as their major ligands, and receptor overexpression and mutation have been unequivocally demonstrated as the major risk factor in poor prognosis breast cancer. Additionally, it has been demonstrated that all four of the members of this family of receptors can form heterodimeric signalling complexes with other members of the family, and that this can lead to synergistic transforming capacity if more than one member of the family is overexpressed in a malignancy. Overexpression of more than one family member has been shown to be relatively common in human malignancies.

In addition to cancer, restenosis is also a disease in which undesired cellular proliferation occurs. Restenosis involves the proliferation of vascular smooth muscle cells. Restenosis is a major clinical problem associated with coronary angioplasty and other medical procedures. Restenosis generally occurs within about 0 to 6 months in about 30% to 50% of patients who undergo balloon angioplasty to clear clogged coronary arteries in an effort to treat heart disease due to occluded arteries. The resulting restenosis causes substantial patient morbidity and health care expense.

The process of restenosis is initiated by injury of the blood vessel, including arteries and veins, with the subsequent release of thrombogenic, vasoactive, and mitogenic factors. Endothelial and deep vessel injury leads to platelet aggregation, thrombus formation, inflammation, and activation of macrophages and smooth muscle cells. These events induce the production of and release of growth factors and cytokines, which in turn may promote their own synthesis and release from target cells. Thus, a self-perpetuating process involving growth factors such as EGF, platelet derived growth factor (PDGF) or fibroblast growth factor (FGFs) is initiated. Thus, it would be useful to have irreversible inhibitors of signal transduction pathways, particularly of tyrosine kinases like EGF, PDGF, FGF, or src tyrosine kinases.

The proliferative skin disease psoriasis has no good cure at present. It is often treated by anticancer agents such as methotrexate, which have very serious side effects, and which are not very effective at the toxicity limited doses which have to be used. It is believed that TGF alpha is the major growth factor overproduced in psoriasis, since 50% of transgenic mice which over express TGF alpha develop psoriasis. This suggests that a good inhibitor of EGFR signalling could be used as antipsoriatic agent, preferably, but not necessarily, by topical dosing.

It is especially advantageous to have irreversible tyrosine kinase inhibitors when compared to reversible inhibitors, because irreversible inhibitors can be used in prolonged suppression of the tyrosine kinase, limited only by the normal rate of receptor resynthesis, also called turnover.

Additional information on the role of src tyrosine kinases in biological processes relating to cancer and restenosis can be found in the following documents, which are all hereby incorporated by reference.

Benjamin C. W. and Jones D. A, Platelet-Derived Growth Factor Stimulates Growth Factor Receptor Binding Protein-2 Association With Src In Vascular Smooth Muscle Cells, *JBC,* 1994;269:30911–30916.

Kovalenko M., et al., Selective Platelet-Derived Growth Factor Receptor Kinase Blockers Reverse Cis-transformation, *Cancer Res,* 1994;54:6106–6114.

Schwartz R. S., et al., The Restenosis Paradigm Revisted: An Alternative Proposal for Cellular Mechanisms, *J Am Coll Cardiol,* 1992;20:1284–1293.

Libby P., et al., Cascade Model for Restenosis—A Special Case of Atherosclerosis Progression, *Circulation,* 1992;86:47–52.

Additional information on the role of EGF tyrosine kinases in biological processes relating to cancer and restenosis can be found in the following document which is hereby incorporated by reference.

Jonathan Blay and Morley D. Hollenberg, Heterologous Regulation Of EGF Receptor Function In Cultured Aortic Smooth Muscle Cells, *Eur J Pharmacol, Mol Pharmacol Sect*, 1989;172(1):1–7.

Information that shows that antibodies to EGF or EGFR show in vivo antitumor activity can be found in the following documents which are hereby incorporated by reference.

Modjtahedi H., Eccles S., Box G., Styles J., Dean C, Immunotherapy Of Human Tumour Xenografts Overexpressing The EGF Receptor With Rat Antibodies That Block Growth Factor-Receptor Interaction, *Br J Cancer*, 1993;67:254–261.

Kurachi H., Morishige K. I., Amemiya K., Adachi H., Hirota K., Miyake A., Tanizawa O, Importance Of Transforming Growth Factor Alpha/Epidermal Growth Factor Receptor Autocrine Growth Mechanism In An Ovarian Cancer Cell Line In Vivo, *Cancer Res*, 1991;51:5956–5959.

Masui H., Moroyama T., Mendelsohn J. Mechanism Of Antitumor Activity In Mice For Anti-Epidermal Growth Factor Receptor Monoclonal Antibodies With Different Isotypes, *Cancer Res*, 1986;46:5592–5598.

Rodeck U., Herlyn M., Herlyn D., Molthoff C., Atkinson B., Varello M., Steplewski Z., Koprowski H., Tumor Growth Modulation By A Monoclonal Antibody To The Epidermal Growth Factor Receptor: Immunologically Mediated And Effector Cell-Independent Effects, *Cancer Res*, 1987;47:3692–3696.

Guan E., Zhou T., Wang J., Huang P., Tang W., Zhao M., Chen Y., Sun Y, Growth Inhibition Of Human Nasopharyngeal Carcinoma In Athymic Mice By Anti-Epidermal Growth Factor Receptor Monoclonal Antibodies, *Internat J Cell Clon*, 1989;7:242–256.

Masui H., Kawamoto T., Sato J. D., Wolf B., Sato G., Mendelsohn J, Growth Inhibition Of Human Tumor Cells In Athymic Mice By Anti-Epidermal Growth Factor Receptor Monoclonal Antibodies, *Cancer Res*, 1984;44:1002–1007.

In addition, the following documents show the antitumor activity of protein tyrosine kinase inhibitors. The documents are hereby incorporated by reference.

Buchdunger E., Trinks U., Mett H., Regenass U., Muller M., Meyer T., McGlynn E., Pinna L. A., Traxler P., Lydon N. B. 4,5-Dianilinophthalimide: A Protein Tyrosine Kinase Inhibitor With Selectivity For The Epidermal Growth Factor Receptor Signal Transduction Pathway And Potent In Vivo Antitumor Activity, *Proc Natl Acad Sci USA*, 1994;91:2334–2338.

Buchdunger E., Mett H., Trinks U., Regenass U., Muller M., Meyer T., Beilstein P., Wirz B., Schneider P., Traxler P., Lydon N. 4,5-Bis(4-Fluoroanilino)Phthalimide: A Selective Inhibitor Of The Epidermal Growth Factor Receptor Signal Transduction Pathway With Potent In Vivo Mdd Antitumor Activity, *Clinical Cancer Research*, 1995; 1:813–821.

Compounds that are reversible inhibitors of tyrosine kinases have been described in U.S. Pat. Nos. 5,457,105, 5,475,001, and 5,409,930 and in PCT publication Numbers WO 9519774 and WO 9519970. The presently disclosed compounds, which are structurally different from the tyrosine kinase inhibitors described in the above-identified documents, are irreversible inhibitors of tyrosine kinases.

SUMMARY OF THE INVENTION

The present invention provides compounds having the Formula I

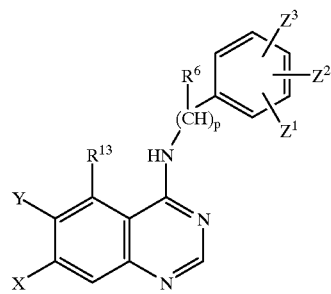

wherein X is —D—E—F and Y is —$SR^4$, halogen, —$OR^4$, —$NHR^3$, or hydrogen, or X is —$SR^4$, halogen, —$OR^4$, —$NHR^3$, or hydrogen, and Y is —D—E—F;

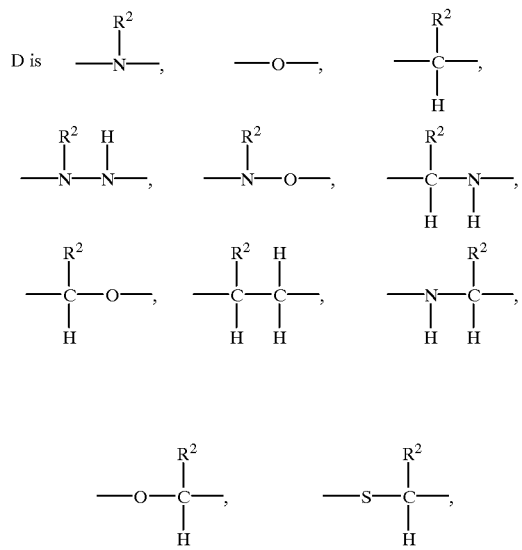

or absent;

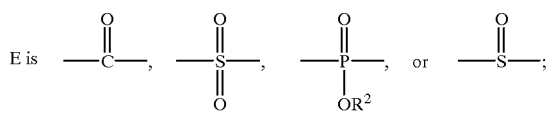

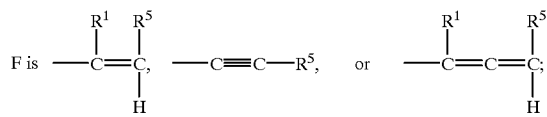

provided that when E is

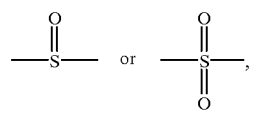

D is not $$-\underset{H}{\overset{R^2}{\underset{|}{N}}}-\underset{H}{\overset{|}{\underset{|}{C}}}-, \quad \text{or} \quad -\underset{H}{\overset{R^2}{\underset{|}{OC}}};$$

$R^1$ is hydrogen, halogen, or $C_1$–$C_6$ alkyl;

$R^2$, $R^3$, and $R^4$ are independently hydrogen, $C_1$–$C_6$ alkyl, —$(CH_2)_n$-N-piperidinyl, —$(CH_2)_n$-N-piperazinyl, —$(CH_2)_n$-$N_1$-piperazinyl[$N_4$-($C_1$–$C_6$)alkyl], —$(CH_2)_n$-N-pyrrolidyl, —$(CH_2)_n$-pyridinyl, —$(CH_2)_n$-N-imidazoyl, —$(CH_2)_n$-imidazoyl, —$(CH_2)_n$-N-morpholino, —$(CH_2)_n$-N-thiomorpholino, —$(CH_2)_n$-N-hexahydroazepine or substituted $C_1$–$C_6$ alkyl, wherein the substituents are selected from —OH, —$NH_2$, or $$-\underset{\underset{B}{\overset{|}{\underset{|}{N}}}}{\overset{A}{\underset{|}{\phantom{N}}}}-$$

A and B are independently hydrogen, $C_1$–$C_6$ alkyl, —$(CH_2)_n$OH, —$(CH_2)_n$-N-piperidinyl, —$(CH_2)_n$-N-piperazinyl, —$(CH_2)$ —$N_1$-piperazinyl[$N_4$-($C_1$–$C_6$)alkyl], —$(CH_2)_n$-N-pyrrolidyl, —$(CH_2)_n$-N-pyridyl, —$(CH_2)_n$-imidazoyl, or —$(CH_2)_n$-N-imidazoyl;

$Z^1$, $Z^2$, or $Z^3$ are independently hydrogen, halogen, $C_1$–$C_6$ alkyl, $C_3$–$C_8$ cycloalkyl, $C_1$–$C_6$ alkoxy, $C_3$–$C_8$ cycloalkoxy, nitro, $C_1$–$C_6$ perfluoroalkyl, hydroxy, $C_1$–$C_6$ acyloxy, —$NH_2$, —NH($C_1$–$C_6$ alkyl), —N($C_1$–$C_6$ alkyl)$_2$, —NH($C_3$–$C_8$ cycloalkyl), —N($C_3$–$C_8$ cycloalkyl)$_2$, hydroxymethyl, $C_1$–$C_6$ acyl, cyano, azido, $C_1$–$C_6$ thioalkyl, $C_1$–$C_6$ sulfinylalkyl, $C_1$–$C_6$ sulfonylalkyl, $C_3$–$C_8$ thiocycloalkyl, $C_3$–$C_8$ sulfinylcycloalkyl, $C_3$–$C_8$ sulfonylcycloalkyl, mercapto, $C_1$–$C_6$ alkoxycarbonyl, $C_3$–$C_8$ cycloalkoxycarbonyl, $C_2$–$C_4$ alkenyl, $C_4$–$C_8$ cycloalkenyl, or $C_2$–$C_4$ alkynyl;

$R^5$ is hydrogen, halogen, $C_1$–$C_6$-perfluoroalkyl, 1,1-difluoro($C_1$–$C_6$)alkyl, $C_1$–$C_6$alkyl, —$(CH_2)_n$-N-piperidinyl, —$(CH_2)_n$-piperazinyl, —$(CH_2)_n$-piperazinyl[$N_4$-($C_1$–$C_6$)alkyl], —$(CH_2)_n$-N-pyrrolidyl, —$(CH_2)_n$-pyridinyl, —$(CH_2)_n$-N-imidazoyl, —$(CH_2)_n$-N-morpholino, —$(CH_2)_n$-N-thiomorpholino, $$-\underset{H}{\overset{|}{\underset{|}{C}}}=CH_2,$$

—CH=CH—($C_1$–$C_6$)alkyl, —$(CH_2)_n$-N-hexahydroazepine, —$(CH_2)_n$NH$_2$, —$(CH_2)_n$NH ($C_l$–$C_6$alkyl), —$(CH_2)_n$N($C_1$–$C_6$alkyl)$_2$, -1-oxo($C_1$–$C_6$) alkyl, carboxy, ($C_1$–$C_6$)alkyloxycarbonyl, N—($C_1$–$C_6$) alkylcarbamoyl, phenyl or substituted phenyl, wherein the substituted phenyl can have from one to three substituents independently selected from $Z^1$, $Z^{22}$, $Z^3$ or a monocyclic heteroaryl group, and each $C_1$–$C_6$ alkyl group above in $R^5$ can be substituted with —OH, —$NH_2$ or —NAB, where A and B are as defined above, $R^6$ is hydrogen or $C_1$–$C_6$ alkyl; $R^{13}$ is hydrogen or halogen; and n is 1 to 4, p is 0 or 1, and the pharmaceutically acceptable salts, esters, amides, and prodrugs thereof.

In a preferred embodiment of the compound of Formula I, $Z^1$ and $Z^2$ are hydrogen, and $Z^3$ is a halogen.

In a more preferred embodiment of the compounds of Formula I, $Z^3$ is bromine.

In another more preferred embodiment of the compounds of Formula I, the bromine is located at the 3 or meta position of the phenyl ring.

In another preferred embodiment, $Z^1$ is hydrogen, $Z^2$ is F, and $Z^3$ is Cl.

In another more preferred embodiment, $Z^1$ is hydrogen, $Z^2$ is F, and $Z^3$ is Cl, wherein $Z^2$ is located at the 4 position, and $Z^3$ is located at the 3 position of the phenyl ring.

In another preferred embodiment of the compounds of Formula I,

X is $$-\underset{}{\overset{R^2}{\underset{|}{N}}}-\underset{}{\overset{O}{\underset{\|}{C}}}-\underset{}{\overset{CHR^5}{\underset{|}{C}}}-R^1,$$

and Y is hydrogen, or
X is hydrogen, and Y is $$-\underset{}{\overset{R^2}{\underset{|}{N}}}-\underset{}{\overset{O}{\underset{\|}{C}}}-\underset{}{\overset{CHR^5}{\underset{|}{C}}}-R^1.$$

In another preferred embodiment of the compounds of Formula I, Y is —D—E—F, and —D—E—F is $$-\underset{}{\overset{R^2}{\underset{|}{N}}}-\underset{}{\overset{O}{\underset{\|}{C}}}-\underset{}{\overset{R^1}{\underset{|}{C}}}=\underset{}{\overset{R^5}{\underset{|}{CH}}}, \quad -\underset{}{\overset{R^2}{\underset{|}{N}}}-\underset{\underset{O}{\|}}{\overset{O}{\underset{\|}{S}}}-\underset{}{\overset{R^1}{\underset{|}{C}}}=\underset{}{\overset{R^5}{\underset{|}{CH}}}, \text{or}$$

$$-\underset{}{\overset{R^2}{\underset{|}{N}}}-\underset{\underset{OR^2}{|}}{\overset{O}{\underset{\|}{P}}}-\underset{}{\overset{R^1}{\underset{|}{C}}}=\underset{}{\overset{R^5}{\underset{|}{CH}}}.$$

In another preferred embodiment of the compounds of Formula I, X is —D—E—F, and —D—E—F is $$-\underset{}{\overset{R^2}{\underset{|}{N}}}-\underset{}{\overset{O}{\underset{\|}{C}}}-\underset{}{\overset{R^1}{\underset{|}{C}}}=\underset{}{\overset{R^5}{\underset{|}{CH}}}, \quad -\underset{}{\overset{R^2}{\underset{|}{N}}}-\underset{\underset{O}{\|}}{\overset{O}{\underset{\|}{S}}}-\underset{}{\overset{R^1}{\underset{|}{C}}}=\underset{}{\overset{R^5}{\underset{|}{CH}}}, \text{or}$$

$$-\underset{}{\overset{R^2}{\underset{|}{N}}}-\underset{\underset{OR^2}{|}}{\overset{O}{\underset{\|}{P}}}-\underset{}{\overset{R^1}{\underset{|}{C}}}=\underset{}{\overset{R^5}{\underset{|}{CH}}}.$$

In another preferred embodiment of the compounds of Formula I, $R^2$ is hydrogen.

In another preferred embodiment of the compounds of Formula I, Y is —D—E—F and X is —O($CH_2$)$_n$-morpholino.

In another preferred embodiment of the compounds of Formula I, $R^5$ is carboxy, ($C_1$–$C_6$ alkyl)oxycarbonyl or $C_1$–$C_6$ alkyl.

In another preferred embodiment of the compounds of Formula I, Y is —D—E—F and X is —O($CH_2$)$_n$morpholino.

In another preferred embodiment of the compounds of Formula I, Y is —D—E—F and X is —O—($CH_2$)$_n$-$N_1$piperazinyl[$N_4$-($C_1$–$C_6$)alkyl].

In another preferred embodiment of the compounds of Formula I, Y is —D—E—F and X is —O—(CH$_2$)$_n$-imidazoyl.

In another embodiment, the present invention provides compounds having the Formula II

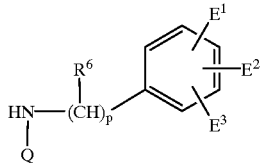

II wherein Q is

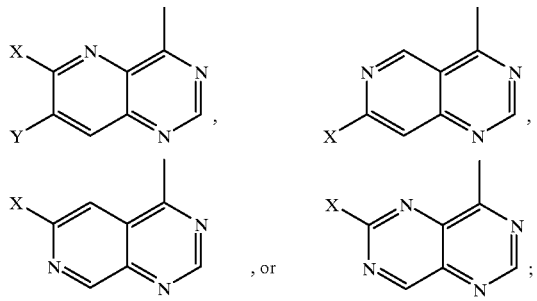

p is 0 or 1;

X is —D—E—F, and Y is —SR$^4$, —OR$^4$, —NHR$^3$ or hydrogen, or X is —SR$^4$, —OR$^4$, NHR$^3$ or hydrogen, and Y is —D—E—F;

D is

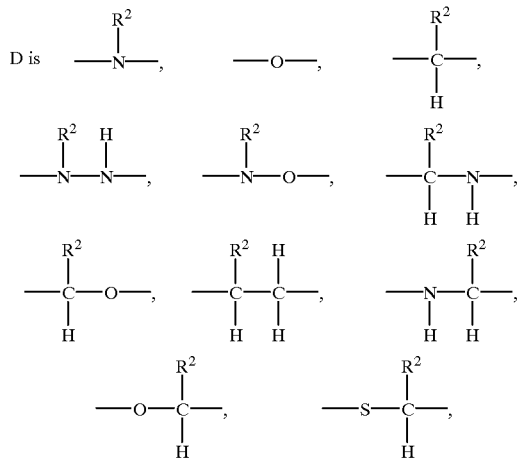

or absent;

E is

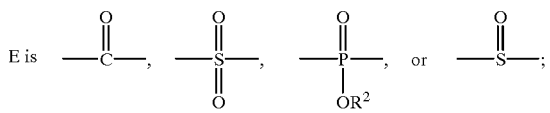

F is

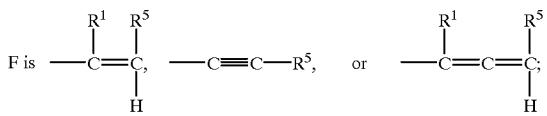

provided that when E is

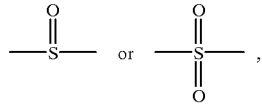

D is not

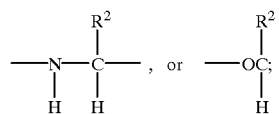

R$^1$ is hydrogen, halogen, or C$_1$–C$_6$ alkyl;

R$^2$, R$^3$, and R$^4$ are independently hydrogen, C$_1$–C$_6$ alkyl, —(CH$_2$)$_n$-N-piperidinyl, —(CH$_2$)$_n$-N-piperazinyl, —(CH$_2$)$_n$-N$_1$-piperazinyl[N$_4$-(C$_1$–C$_6$)alkyl], —(CH$_2$)$_n$-N-pyrrolidyl, —(CH$_2$)$_n$-pyridinyl, —(CH$_2$)$_n$-N-imidazoyl, —(CH$_2$)$_n$-imidazoyl, —(CH$_2$)$_n$-N-morpholino, —(CH$_2$)$_n$-N-thiomorpholino, —(CH$_2$)$_n$-N-hexahydroazepine or substituted C$_1$–C$_6$ alkyl, wherein the substituents are selected from —OH, —NH$_2$, or

A and B are independently hydrogen, C$_1$–C$_6$ alkyl, —(CH$_2$)$_n$OH —(CH$_2$)$_n$-N-piperidinyl, —(CH$_2$)$_n$-N-piperazinyl, —(CH$_2$)$_n$-N$_1$-piperazinyl[N$_4$-(C$_1$–C$_6$) alkyl], —(CH$_2$)$_n$-N-pyrrolidyl, —(CH$_2$)$_n$-N-pyridyl, —(CH$_2$)$_n$-imidazoyl, or —(CH$_2$)$_n$-N-imidazoyl;

E$^1$, E$^2$, and E$^3$ are independently halogen, C$_1$–C$_6$ alkyl, C$_3$–C$_8$ cycloalkyl, C$_1$–C$_6$ alkoxy, C$_3$–C$_8$ cycloalkoxy, nitro, C$_1$–C$_6$ perfluoroalkyl, hydroxy, C$_1$–C$_6$ acyloxy, —NH$_2$, —NH(C$_1$–C$_6$ alkyl), —N(C$_1$–C$_6$ alkyl)$_2$, —NH(C$_3$–C$_8$ cycloalkyl), —N(C$_3$–C$_8$ cycloalkyl)$_2$, hydroxymethyl, C$_1$–C$_6$ acyl, cyano, azido, C$_1$–C$_6$ thioalkyl, C$_1$–C$_6$ sulfinylalkyl, C$_1$–C$_6$ sulfonylalkyl, C$_3$–C$_8$ thiocycloalkyl, C$_3$–C$_8$ sulfinylcycloalkyl, C$_3$–C$_8$ sulfonylcycloalkyl, mercapto, C$_1$–C$_6$ alkoxycarbonyl, C$_3$–C$_8$ cycloalkoxycarbonyl, C$_2$–C$_4$ alkenyl, C$_4$–C$_8$ cycloalkenyl, or C$_2$–C$_4$ alkynyl;

R$^5$ is hydrogen, halogen, C$_1$–C$_6$-perfluoroalkyl, 1,1-difluoro(C$_1$–C$_6$)alkyl, C$_1$–C$_6$ alkyl, —(CH$_2$)$_n$-N-piperidinyl, —(CH$_2$)$_n$-piperazinyl, —(CH$_2$)$_n$-piperazinyl[N$_4$-(C$_1$–C$_6$)alkyl], —(CH$_2$)$_n$-N-pyrrolidyl, —(CH$_2$)$_n$-pyridinyl, —(CH$_2$)$_n$-N-imidazoyl, —(CH$_2$)$_n$-N-morpholino, —(CH$_2$)$_n$-N-thiomorpholino,

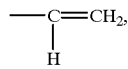

—CH=CH—(C$_1$-C$_6$)alkyl, —(CH$_2$)$_n$-N-hexahydroazepine, —(CH$_2$)$_n$NH$_2$, —(CH$_2$)$_n$NH(C$_1$-C$_6$ alkyl), —(CH$_2$)$_n$N(C$_1$-C$_6$ alkyl)$_2$, -1-oxo(C$_1$-C$_6$)alkyl, carboxy, (C$_1$-C$_6$)alkyloxycarbonyl, N-(C$_1$-C$_6$)alkylcarbamoyl, phenyl or substituted phenyl, wherein the substituted phenyl can have from one to three substituents independently selected from Z$^1$, Z$^2$, Z$^3$ or a monocyclic heteroaryl group, and each C$_1$-C$_6$ alkyl group can be substituted with —OH, —NH$_2$ or —NAB, where A and B are as defined above, R$^6$ is hydrogen or C$_1$-C$_6$ alkyl; and n is 1 to 4, p is 0 and 1, and the pharmaceutically acceptable salts, esters, amides, and prodrugs thereof.

In a preferred embodiment of the compounds of Formula II, E$^1$ and E$^2$ are hydrogen, and E$^3$ is a halogen.

In a more preferred embodiment of the compounds of Formula II, the halogen is bromine.

In another more preferred embodiment of the compounds of Formula II, the bromine is located at the three or meta position of the phenyl ring.

In another more preferred embodiment, E$^1$ is hydrogen, E$^2$ is chlorine, and E$^3$ is fluorine.

In another preferred embodiment of the compounds of Formula II, Q is

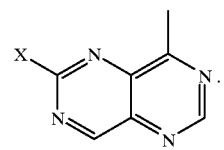

In another preferred embodiment of the compounds of Formula II, Q is

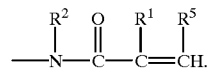

In another preferred embodiment of the compounds of Formula II, Q is

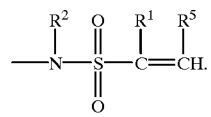

In another preferred embodiment of the compounds of Formula II, Q is

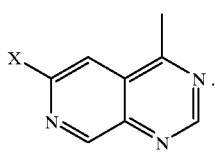

In another preferred embodiment of the compounds of Formula II, X is

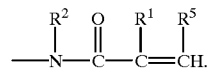

In another preferred embodiment of the compounds of Formula II, X is $$\underset{R^2}{\overset{}{N}}-\overset{O}{\underset{}{C}}-\overset{R^1}{\underset{}{C}}=\overset{R^5}{\underset{}{C}}H.$$

In another preferred embodiment of the compounds of Formula II, X is $$\underset{R^2}{\overset{}{N}}-\overset{O}{\underset{O}{S}}-\overset{R^1}{\underset{}{C}}=\overset{R^5}{\underset{}{C}}H.$$

In another embodiment, the present invention provides compounds having the Formula III

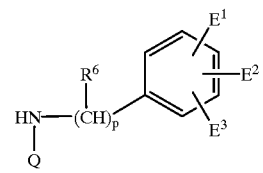

wherein Q is

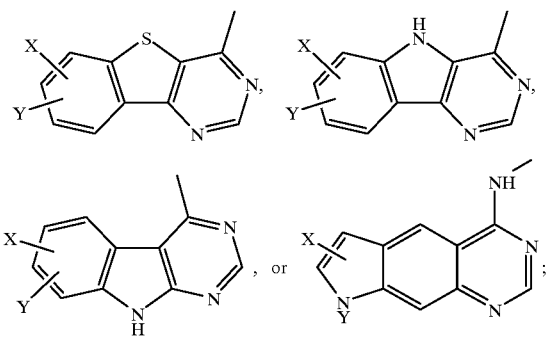

p is 0 or 1;

X is —D—E—F, and Y is —SR$^4$, —OR$^4$, —NHR$^3$ or hydrogen, or X is —SR$^4$, —OR$^4$, —NHR$^3$ or hydrogen, and Y is —D—E—F;

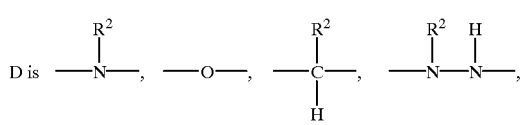

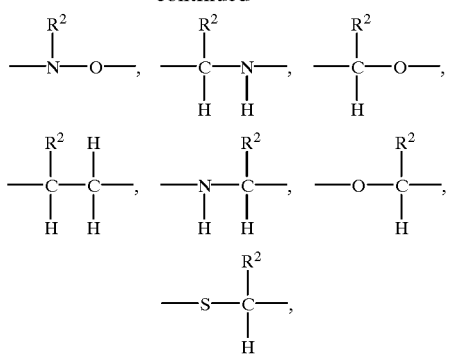

or absent;

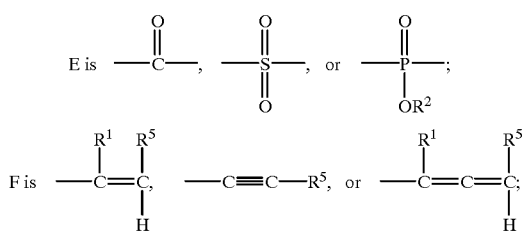

provided that when E is

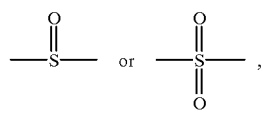

D is not

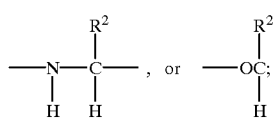

$R^1$ is hydrogen, halogen, or $C_1$–$C_6$ alkyl;

$R^2$, $R^3$, and $R^4$ are independently hydrogen, $C_1$–$C_6$ alkyl, —$(CH_2)_n$-N-piperidinyl, —$(CH_2)_n$-N-piperazinyl, —$(CH_2)_n$-N$_1$-piperazinyl[N$_4$-($C_1$–$C_6$)alkyl], —$(CH_2)_n$-N-pyrrolidyl, —$(CH_2)_n$-pyridinyl, —$(CH_2)_n$-N-imidazoyl, —$(CH_2)_n$-N-morpholino, —$(CH_2)_n$-N-thiomorpholino, —$(CH_2)_n$-N-hexahydroazepine or substituted $C_1$–$C_6$ alkyl, wherein the substituents are selected from —OH, —NH$_2$, or

A and B are independently hydrogen, $C_1$–$C_6$ alkyl, —$(CH_2)_n$OH, —$(CH_2)_n$-N-piperidinyl, —$(CH_2)_n$-N-piperazinyl, —$(CH_2)_n$-N$_1$-piperazinyl[N$_4$-($C_1$–$C_6$)alkyl], —$(CH_2)_n$-N-pyrrolidyl, —$(CH_2)_n$-N-pyridyl, —$(CH_2)_n$-imidazoyl, or —$(CH_2)_n$-N-imidazoyl;

$E^1$, $E^2$, and $E^3$ are independently halogen, $C_1$–$C_6$ alkyl, $C_3$–$C_8$ cycloalkyl, $C_1$–$C_6$ alkoxy, $C_3$–$C_8$ cycloalkoxy, nitro, $C_1$–$C_6$ perfluoroalkyl, hydroxy, $C_1$–$C_6$ acyloxy, —NH$_2$, —NH($C_1$–$C_6$ alkyl), —N($C_1$–$C_6$ alkyl)$_2$, —NH($C_3$–$C_8$ cycloalkyl), —N($C_3$–$C_8$ cycloalkyl)$_2$, hydroxymethyl, $C_1$–$C_6$ acyl, cyano, azido, $C_1$–$C_6$ thioalkyl, $C_1$–$C_6$ sulfinylalkyl, $C_1$–$C_6$ sulfonylalkyl, $C_3$–$C_8$ thiocycloalkyl, $C_3$–$C_8$ sulfinylcycloalkyl, $C_3$–$C_8$ sulfonylcycloalkyl, -mercapto, $C_1$–$C_6$ alkoxycarbonyl, $C_3$–$C_8$ cycloalkoxycarbonyl, $C_2$–$C_4$ alkenyl, $C_4$–$C_8$ cycloalkenyl, or $C_2$–$C_4$ alkynyl;

$R^5$ is hydrogen, halogen, $C_1$–$C_6$-perfluoroalkyl, 1,1-difluoro($C_1$–$C_6$)alkyl, $C_1$–$C_6$ alkyl, —$(CH_2)_n$-N-piperidinyl, —$(CH_2)_n$-piperazinyl, —$(CH_2)_n$-piperazinyl[N$_4$-($C_1$–$C_6$)alkyl], —$(CH_2)_n$-N-pyrrolidyl, —$(CH_2)_n$-pyridinyl, —$(CH_2)_n$-N-imidazoyl, —$(CH_2)_n$-N-morpholino, —$(CH_2)_n$-N-thiomorpholino,

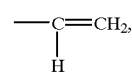

—CH=CH—($C_1$–$C_6$)alkyl, —$(CH_2)_n$-N-hexahydroazepine, —$(CH_2)_n$NH$_2$, —$(CH_2)_n$NH($C_1$–$C_6$ alkyl), —$(CH_2)_n$N($C_1$–$C_6$ alkyl)$_2$, -1-oxo($C_1$–$C_6$)alkyl, carboxy, ($C_1$–$C_6$)alkyloxycarbonyl, N-($C_1$–$C_6$) alkylcarbamoyl, phenyl or substituted phenyl, wherein the substituted phenyl can have from one to three substituents independently selected from $Z^1$, $Z^{21}$, $Z^3$ or a monocyclic heteroaryl group, and each $C_1$–$C_6$ alkyl group can be substituted with —OH, —NH$_2$ or —NAB, where A and B are as defined above, $R^6$ is hydrogen or $C_1$–$C_6$ alkyl; and n is 1 to 4, and the pharmaceutically acceptable salts, esters, amides, and prodrugs thereof.

In another preferred embodiment of the compounds of Formula III, Q is

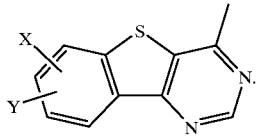

In another preferred embodiment of the compounds of Formula III, Q is

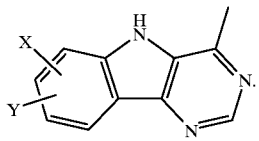

In another preferred embodiment of the compounds of Formula III, X is

In another preferred embodiment of the compounds of Formula III, $E^1$ and $E^2$ are hydrogen and $E^3$ is bromine.

In another preferred embodiment of the compounds of Formula III, $E^1$ is hydrogen, $E^2$ is chlorine, and $E^3$ is fluorine.

In another preferred embodiment of the compounds of Formula III, X is

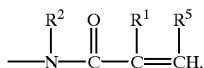

In another preferred embodiment, Q is a 6-substituted benzothieno[3,2-d]pyrmid-4-yl.

The present invention also provides a pharmaceutically acceptable composition that comprises a compound of Formula I, II, or III.

The present invention also provides a method of treating cancer, the method comprising administering to a patient having cancer a therapeutically effective amount of a compound of Formula I, II, or III.

The present invention also provides a method of treating or preventing restenosis, the method comprising administering to a patient having restenosis or at risk of having restenosis, a therapeutically effective amount of a compound of Formula I, II, or III.

The present invention also provides a method of treating psoriasis, the method comprising administering to a patient having psoriasis a therapeutically effective amount of a compound of Formula I, II, or III.

The present invention also provides a method of treating atherosclerosis, the method comprising administering to a patient having atherosclerosis a therapeutically effective amount of a compound of Formula I, II, or III.

The present invention also provides a method of treating endometriosis, the method comprising administering to a patient having endometriosis a therapeutically effective amount of a compound of Formula I, II, or III.

The present invention also provides a method of irreversibly inhibiting tyrosine kinases, the method comprising administering to a patient in need of tyrosine kinase inhibition a tyrosine kinase inhibiting amount of a compound of Formula I, II or III.

The present invention provides the following compounds:

N-[4-(3-Bromo-phenylamino)-pyrido[4,3-d]pyrimidin-7-yl]-N-(3-morpholin-4-yl-propyl)-acrylamide;
N-[4-(3-Bromo-phenylamino)-pyrido[3,4-d]pyrimidin-6-yl]-N-(3-morpholin-4-yl-propyl)-acrylamide;
N-[4-(3-Bromo-phenylamino)-quinazolin-7-yl]-acrylamide;
N-[4-[(3-Bromophenyl)amino]quinazolin-7-yl]N-[3-morpholinopropyl]-acrylamide;
3-[4-(3-Bromo-phenylamino)-guinazolin-7-ylcarbamoyl]-acrylic acid;
3-[4-(3-Bromo-phenylamino)-quinazolin-7-ylcarbamoyl]-acrylic acid ethyl ester;
But-2-enoic acid [4-(3-bromo-phenylamino)quinazolin-7-yl]-amide;
N-[4-(3-Bromo-phenylamino)-6-(3-morpholin-4-ylpropylamino)-quinazolin-7-yl]-acrylamide;
N-[4-[(3-Bromophenyl)amino]quinazolin-6-yl]-acrylamide;
N-[4-(3-Methyl-phenylamino)-quinazolin-7-yl]-acrylamide;
N-[4-(3-Chloro-phenylamino)-quinazolin-7-yl]-acrylamide;
N-[4-(3- Bromo-phenylamino)-quinazolin-7-yl]-methacrylamide;
N-[4-(3-Bromo-phenylamino)-quinazolin-7-yl] ethenylsulfonamide;
N-[4-[(3-Chlorophenyl)amino]quinazolin-6-yl]-acrylamide;
N-[4-[(3-Methylphenyl)amino]quinazolin-6-yl]-acrylamide;
N-[4-[(3-(Trifluoromethyl)phenyl)amino]quinazolin6-yl]-acrylamide;
N-[4-[(3-Bromophenyl)amino]-7-[3-(4-morpholino)propoxy]quinazolin-6-yl]-acrylamide;
N-[4-[(3-Methylphenyl)amino]-7-[3-(4-morpholino)propoxy]quinazolin-6-yl]-acrylamide;
N-[4-[(3-Methylphenyl)amino]-7-[3-(4,N-methyl-1,N-piperazino)propoxy]quinazolin-6-yl]-acrylamide;
N-[4-[(3-Bromophenyl)amino]-7-[3-(4,N-methyl-1,N-piperazino)propoxy]quinazolin-6-yl]-acrylamide;
N-[4-[(3-Bromophenyl)amino]-7-[3-(1,N-imidazyl)propoxy]quinazolin-6-yl]acrylamide;
N-[4-[(3-Bromophenyl)amino]-7-[4-(N,N-dimethylamino)butoxy]quinazolin-6-yl]-acrylamide;
N-[4-[(3-Bromophenyl)amino]quinazolin-6-yl]-N[3-morpholinopropyl]-acrylamide;
N-[4-[(3-Bromophenyl)amino]quinazolin-6-yl]-methacrylamide;
N-[4-(3-Bromo-phenylamino)-quinazolin-7-yl]-ethenylsulfonamide;
N-[4-[(3-Bromophenyl)amino]quinazolin-6-yl]-E-but-2-enamide;
N-[4-[(3-Bromophenyl)amino]quinazolin-6-yl]4,4,4-trifluoro-E-but-2-enamide;
N-[4-[(3-Bromophenyl)amino]quinazolin-6-yl] propynamide;
N-[4-[(3-Bromophenyl)amino]quinazolin-6-yl]but2-ynamide;
N-[4-(3-Bromo-phenylamino)-pyrido[4,3-d]pyrimidin7-yl]-acrylamide;
N-[4-(3-Bromo-phenylamino)-pyrido[3,4-d]pyrimidin6-yl]-acrylamide;
N-[4-(3-Methyl-phenylamino)-pyrido[3,4-d]pyrimidin-6-yl]-acrylamide;
N-[4-(3-Bromo-phenylamino)-pyrido[3,4-d]pyrimidin6-yl]-N-methyl acrylamide;
N-[4-(3-Bromo-phenylamino)-pyrido[3,4-d]pyrimidin6-yl]-methacrylamide;
N-[4-(3-Bromo-phenylamino)-pyrido[3,4-d]pyrimidin6-yl]-ethenylsulfonamide;
N-[4-(3-Bromo-phenylamino)-pyrido[3,2-d]pyrimidin6-yl]-acrylamide;
N-[4-(3-Bromo-phenylamino)-benzo[b]thieno[3,2-d]pyrimidin-8-yl]acrylamide;
N-[4-(3-Bromo-phenylamino)-benzo[b]thieno[3,2-d]pyrimidin-6-yl]acrylamide;
N-[4-(3-Bromo-phenylamino)-benzo[b]thieno[3,2-d]pyriimidin-7-yl]acrylamide;
N-[4-[(3-Bromophenyl)amino]quinazolin-6-yl]buta2,3-dienamide;
N-[4-[(3-Bromophenyl)amino]quinazolin-6-yl]-E,4oxopent-2-enamide;
N-[4-[(3-Bromophenyl)amino]quinazolin-6-yl]-E,4ethoxy-4-oxobut-2-enamide;
N-[4-(3-Bromo-phenylamino)-pyrido[3,4-d]pyrimidin6-yl]penta-2,4-dienamide;
N-[4-(3-Bromo-phenylamino)-pyrido[3,4-d]pyrimidin6-yl]-N-(2-(N,N-dimethylamino)ethyl)acrylamide;
N-[4-(3-Bromo-phenylamino)-pyrido [3,4-d]pyrimidin6-yl]E-but-2-enamide;

N-[4-(3-Bromo-phenylamino)-pyrido[3,4-d]pyrimidin6-yl]cinnamide;

N-[4-(3-Bromo-phenylamino)-pyrido[3,4-d]pyrimidin6-yl]-E,3-chloroacrylamide;

N-[4-(3-Bromo-phenylamino)-pyrido[3,4-d]pyrimidin6-yl]-propynamide;

N-[4-[(3-Bromophenyl)amino]quinazolin-6-yl]-E,4(3-(N,N-dimethylamino)propoxy-4-oxobut-2-enamide tris trifluoroacetate;

3-[4-(3-Bromo-phenylamino)-quinazolin-6ylcarbamoyl]-acrylic acid (Z);

N-[4-[(3-Bromophenyl)amino]quinazolin-6-yl]-E,4(3-(N,N-dimethylamino)propylamino-4-oxobut-2-enamide;

4-[(3-Bromo-phenyl)amino]-6-(ethenesulfonyl)pyrido[3,4-d]pyrimidine;

1-[4-(3-Bromo-phenylamino)-quinazolin-6-yl]pyrrole-2,5-dione;

1-[4-(3-Bromo-phenylamino)-quinazolin-6-yl]-prop2-en-1-one;

Acrylic acid 4-(3-bromo-phenylamino)-quinazolin-6-yl ester;

Methyl N-[4-[(3-bromophenyl)amino]-P-ethenylpyrido[3,$^4$-d]pyrimidin-6-yl]phosphonamidate;

Acrylic acid 4-(3-bromo-phenylamino)-quinazolin7-yl ester;

1-[4-(3-Bromo-phenylamino)-quinazolin-6-yl]-but-3en-2-one;

Acrylic acid 4-(3-chloro-4-fluoro-phenylamino)-7methoxy-quinazolin-6-yl ester;

N-[4-(3-Bromo-phenylamino)-7-(3-morpholin-4-ylpropoxy)-pyrido[3,2-d]pyrimidin-6-yl]-acryl amide;

Penta-2,3-dienoic acid [4-(3-bromo-phenylamino)quinazolin-6-yl]-amide;

Propa-1,2-diene-1-sulfonic acid [4-(3-bromophenylamino)-quinazolin-6-yl]-amide;

Methyl N-[4-[(3-bromophenyl)amino]-6quinazolinyl]-P-(1,2-propadienyl)phosphonamidate;

N-[1-(3-Bromo-phenylamino)-9H-2,4,9-triazafluoren-7-yl]-acrylamide;

N-[4-(3-Bromo-phenylamino)-9H-1,3,9-triazafluoren-6-yl]-acrylamide;

N-[4-(3-Chloro-4-fluoro-phenylamino)-quinazolin-6yl]-acrylamide;

N-(4-Phenylmethylamino-quinazolin-6-yl)acrylamide;

(S) -N-[4-(1-Phenyl-ethylamino)-quinazolin-6-yl]-acrylamide;

(R)-N-[4-(1-Phenyl-ethylamino)-quinazolin-6-yl]-acrylamide;

But-2-enedioic acid [4-(3-chloro-4-fluorophenylamino)-guinazolin-6-yl]-amide (3-dimethylaminopropyl)-amide;

N-[4-(3-Chloro-4-fluoro-phenylamino)-pyrido[3,4-d]pyrimidin-6-yl]-acrylamide;

N-[4-(3-Chloro-4-fluoro-phenylamino)-pyrido [3,4-d]pyrimidin-6-yl]-N-methyl-acrylamide;

But-2-enedioic acid [4-(3-chloro-4-fluorophenylamino)-pyrido[3,4-d]pyrimidin-6-yl]-amide (3-dimethylamino-propyl)-amide;

But-2-enedioic acid [4-(3-chloro-4-fluorophenylamino)-pyrido[3,4-d]pyrimidin-6-yl]-amide (3-imidazol-1-yl-propyl)-amide;

4,4-Difluoro-8-morpholin-4-yl-oct-2-enoic acid [4-[3-chloro-4-fluoro-phenylamino)-pyrido[3,4-d]pyrimidin-6-yl]-amide;

8-Dimethylamino-4,4-difluoro-oct-2-enoic acid (4-(3-chloro-4-fluoro-phenylamino)-pyrido[3,4-d]pyrimidin-6-yl]-amide;

7-Dimethylamino-4,4-difluoro-hept-2-enoic acid [4-(3-chloro-4-fluoro-phenylamino)-pyrido[3,4-d]pyrimidin-6-yl]-amide;

4,4-Difluoro-7-morpholin-4-yl-hept-2-enoic acid [4-(3-chloro-4-fluoro-phenylamino)-pyrido[3,4-d]pyrimidin-6-yl]-amide;

6-Dimethylamino-hex-2-ynoic acid [4-(3-chloro-4fluoro-phenylamino)-pyrido[3,4-d]pyrimidin-6-yl]-amide;

6-Morpholin-4-yl-hex-2-ynoic acid [4-(3-chloro-4fluoro-phenylamino)-pyrido[3,4-d]pyrimidin-6-yl]-amide;

7-Dimethylamino-hept-2-ynoic acid [4-(3-chloro-4fluoro-phenylamino)-pyrido[3,4-d]pyrimidin-6-yl]-amide;

7-Morpholin-4-yl-hept-2-ynoic acid [4-(3-chloro-4fluoro-phenylamino)-pyrido[3,4-d]pyrimidin-6-yl]-amide;

5-Dimethylamino-pent-2-ynoic acid [4-(3-chloro-4fluoro-phenylamino)-pyrido[3,4-d]pyrimidin-6-yl]-amide;

5-Morpholin-4-yl-pent-2-ynoic acid [4-(3-chloro-4-fluoro-phenylamino)-pyrido [3,4-d]pyrimidin-6-yl]-amide;

5-Imidazol-1-yl-pent-2-ynoic acid [4-(3-chloro-4fluoro-phenylamino)-pyrido[3,4-d]pyrimidin-6-yl]-amide;

5-(4-Methyl-piperazin-1-yl-pent-2-ynoic acid [4-(3-chloro-4-fluoro-phenylamino)-pyrido[3,4-d]pyrimidin-6-yl]-amide;

4-[4-(3-Chloro-4-fluoro-phenylamino)-pyrido[3,4-d]pyrimidin-6-ylcarbamoyl]-but-3-enoic acid 2-(4-methylpiperazin-1-yl)-ethyl ester;

4-[4-(3-Chloro-4-fluoro-phenylamino)-pyrido[3,4-d]pyrimidin-6-ylcarbamoyl]-but-3-enoic acid 2-(imidazol1-yl)-ethyl ester;

Pent-2-enedioic acid 1-{[4-(3-chloro-4-fluorophenylamino)-pyrido[3,4-d]pyrimidin-6-yl]-amide} 5-[(3morpholin-4-yl-propyl)-amide];

Pent-2-enedioic acid 1-{[4-(3-chloro-4-fluorophenylamino)-pyrido[3,4-d]pyrimidin-6-yl]-amide} 5-[(3-diethylamino-propyl)-amide];

4-[4-(3-Chloro-4-fluoro-phenylamino)-pyrido[3,4-d]pyrimidin-6-ylcarbamoyl]-but-3-enoic acid 2-morpholin4-yl-ethyl ester;

Pent-2-enedioic acid 1-{[4-(3-chloro-4-fluorophenylamino)-pyrido[3,4-d]pyrimidin-6-yl]-amide} 5-{[3,4-methyl-piperazin-1-yl)-propyl]-amide};

(3-Chloro-4-fluoro-phenyl)-{6-[2-(3-dimethylaminopropoxy)-ethenesulfonyl-pyrido[3,4-d]pyrimidin-4-yl}amine;

(3-Chloro-4-fluoro-phenyl)-(6-{2-[4-(4-methylpiperazin-1-yl)-butylamino]-ethenesulfonyl}pyrido[3,4-d]pyrimidin-4-yl)-amine;

(3-Chloro-4-fluoro-phenyl)-[6-(5-morpholin-4-ylpent-1-ene-1-sulfonyl)-pyrido[3,4-d]pyrimidin-4-yl]amine;

(3-Chloro-4-fluoro-phenyl)-(6-ethenesulfinylpyrido[3,4-d]pyrimidin-4-yl]-amine;

3-[4-(1-Phenyl-ethylamino)-quinazolin-6ylcarbamoyl]-acrylic acid 2-morpholin-4-yl-ethyl ester;

But-2-enedioic acid (4-imidazol-1-yl-butyl)-amide [4-(1-phenyl-ethylamino)-quinazolin-6-yl]-amide;

4-[4-(1-Phenyl-ethylamino)-quinazolin-6ylcarbamoyl]-but-3-enoic acid 3-diethylamino-propyl ester;

Pent-2-enedioic acid 5-{[2-(4-methyl-piperazin-1yl)-ethyl]-amide} 1-{[4-(1-phenyl-ethylamino)quinazolin-6-yl]-amide};

4,4-Difluoro-7-morpholin-4-yl-hept-2-enoic acid [4-(1-phenyl-ethylamino)-quinazolin-6-yl]-amide;

7-Dimethylamino-4,4-difluoro-hept-2-enoic acid [4-(1-phenyl-ethylamino)-quinazolin-6-yl]-amide;

7-Imidazol-1-yl-hept-2-ynoic acid [4-(1-phenylethylamino)-quinazolin-6-yl]-amide;

6-Dimethylamino-hex-2-ynoic acid [4-(1-phenylethylamino)-quinazolin-6-yl]-amide;

But-2-enedioic acid [4-(3-bromo-phenylamino)pyrido[3,4-d]pyrimidin-6-yl]-amide (3-dimethylaminopropyl)-amide;

But-2-enedioic acid [4-(3-bromo-phenylamino)pyrido[3,4-d]pyrimidin-6-yl]-amide (3-imidazol-1-ylpropyl)-amide;

4,4-Difluoro-8-morpholin-4-yl-oct-2-enoic acid [4-(3-bromo-phenylamino)-pyrido[3,4-d]pyrimidin-6-yl]-amide;

8-Dimethylamino-4,4-difluoro-oct-2-enoic acid [4-(3-bromo-phenylamino)-pyrido[3,4-d]pyrimidin-6-yl]-amide;

7-Dimethylamino-4,4-difluoro-hept-2-enoic acid [4-(3-bromo-phenylamino)-pyrido[3,4-d]pyrimidin-6-yl]-amide;

4,4-Difluoro-7-morpholin-4-yl-hept-2-enoic acid [4-(3-bromo-phenylamino)-pyrido[3,4-d]pyrimidin-6-yl]-amide;

6-Dimethylamino-hex-2-ynoic acid [4-(3-bromophenylamino)-pyrido[3,4-d]pyrimidin-6-yl]-amide;

6-Morpholin-4-yl-hex-2-ynoic acid [4-(3-bromophenylamino)-pyrido[3,4-d]pyrimidin-6-yl]-amide;

7-Dimethylamino-hept-2-ynoic acid [4-(3-bromophenylamino)-pyrido[3,4-d]pyrimidin-6-yl]-amide;

7-Morpholin-4-yl-hept-2-ynoic acid [4-(3-bromophenylamino)-pyrido[3,4-d]pyrimidin-6-yl]-amide;

5-Dimethylamino-pent-2-ynoic acid [4-(3-bromophenylamino)-pyrido[3,4-d]pyrimidin-6-yl]-amide;

5-Morpholin-4-yl-pent-2-ynoic acid [4-(3-bromophenylamino)-pyrido[3,4-d]pyrimidin-6-yl]-amide;

5-Imidazol-1-yl-pent-2-ynoic acid [4-(3-bromophenylamino)-pyrido[3,4-d]pyrimidin-6-yl]-amide;

5-(4-Methyl-piperazin-1-yl)-pent-2-ynoic acid [4-(3-bromo-phenylamino)-pyrido[3,4-d]pyrimidin-6-yl] amide;

4-[4-(3-Bromo-phenylamino)-pyrido[3,4-d]pyrimidin6-ylcarbamoyl]-but-3-enoic acid 2-(4-methyl-piperazin-1-yl)-ethyl ester;

4-[4-(3-Bromo-phenylamino)-pyrido[3,4-d]pyrimidin-6-ylcarbamoyl]-but-3-enoic acid 2-imidazol-1-yl-ethyl ester;

Pent-2-enedioic acid 1-{[4-(3-bromo-phenylamino) pyrido[3,4-d]pyrimidin-6-yl]-amide} 5-[(3-morpholin4-yl-propyl)-amide];

Pent-2-enedioic acid 1-{[4-(3-bromo-phenylamino) pyrido[3,4-d]pyrimidin-6-yl]-amide} 5-[(3-diethylaminopropyl)-amide];

4-[4-(3-Bromo-phenylamino)-pyrido[3,4-d]pyrimidin6-ylcarbamoyl]-but-3-enoic acid 2-morpholin-4-yl-ethyl ester;

Pent-2-enedioic acid 1-{[4-(3-bromo-phenylamino) pyrido[3,4-d]pyrimidin-6-yl]-amide} 5-{[3-(4-methylpiperazin-1-yl)-propyl]-amide};

(3-Bromo-phenyl)-{6-[2-(3-dimethylamino-propoxy) ethenesulfonyl]-pyrido[3,4-d]pyrimidin-4-yl}-amine;

(3-Bromo-phenyl)-(6-{2-[4-(4-methyl-piperazin-1-yl)-butylamino]-ethenesulfonyl)-pyrido[3,4-d]pyrimidin 4-yl}-amine;

(3-Bromo-phenyl)-[6-(5-morpholin-4-yl-pent-1-ene-1-sulfonyl)-pyrido[3,4-d]pyrimidin-4-yl]-amine;

(3-Bromo-phenyl)-(6-ethenesulfinyl-pyrido[3,4-d] pyrimidin-4-yl)-amine;

But-2-enedioic acid [4-(3-chloro-4-fluorophenylamino)-quinazolin-6-yl]-amide (3-dimethylaminopropyl)-amide;

But-2-enedioic acid [4-(3-chloro-4-fluorophenylamino)-quinazolin-6-yl]-amide (3-imidazol-1-ylpropyl)-amide;

4,4-Difluoro-8-morpholin-4-yl-oct-2-enoic acid [4-(3-chloro-4-fluoro-phenylamino)-quinazolin-6-yl]-amide;

8-Dimethylamino-4,4-difluoro-oct-2-enoic acid [4-(3-chloro-4-fluoro-phenylamino)-quinazolin-6-yl]-amide;

7-Dimethylamino-4,4-difluoro-hept-2-enoic acid [4-(3-chloro-4-fluoro-phenylamino)-quinazolin-6-yl]-amide;

4,4-Difluoro-7-morpholin-4-yl-hept-2-enoic acid [4-(3-chloro-4-fluoro-phenylamino)-quinazolin-6-yl]-amide;

6-Dimethylamino-hex-2-ynoic acid [4-(3-chloro-4-fluoro-phenylamino)-quinazolin-6-yl]-amide;

6-Morpholin-4-yl-hex-2-ynoic acid [4-(3-chloro-4-fluoro-phenylamino)-quinazolin-6-yl]-amide;

7-Dimethylamino-hept-2-ynoic acid [4-(3-chloro-4-fluoro-phenylamino)-quinazolin-6-yl]-amide;

7-Morpholin-4-yl-hept-2-ynoic acid [4-(3-chloro-4-fluoro-phenylamino)-quinazolin-6-yl]-amide;

5-Dimethylamino-pent-2-ynoic acid [4-(3-chloro-4-fluoro-phenylamino)-quinazolin-6-yl]-amide;

5-Morpholin-4-yl-pent-2-ynoic acid [4-(3-chloro-4-fluoro-phenylamino)-quinazolin-6-yl]-amide;

5-Imidazol-1-yl-pent-2-ynoic acid [4-(3-chloro-4-fluoro-phenylamino)-quinazolin-6-yl]-amide;

5-(4-Methyl-piperazin-1-yl)-pent-2-ynoic acid [4-(3-chloro-4-fluoro-phenylamino)-quinazolin-6-yl]-amide;

Pent-2-enedioic acid 1-{[4-(3-chloro-4-fluorophenylamino)-quinazolin-6-yl]-amide} 5-[(3-morpholin4-yl-propyl)-amide];

Pent-2-enedioic acid 1-{[4-(3-chloro-4-fluorophenylamino)-quinazolin-6-yl]-amide} 5-[(3diethylamino-propyl)-amide];

4-[4-(3-Chloro-4-fluoro-phenylamino)-quinazolin-6-ylcarbamoy]-but-3-enoic acid 2-morpholin-4-yl-ethyl ester;

Pent-2-enedioic acid 1-{[4-(3-chloro-4-fluorophenylamino)-quinazolin-6-yl]-amide} 5-{[3-(4-methylpiperazin-1-yl)-propyl]-amide};

(3-Chloro-4-fluoro-phenyl)-{6-[2-(3-dimethylaminopropoxy)-ethenesulfonyl]-quinazolin-4-yl}-amine;

(3-Chloro-4-fluoro-phenyl)-(6-{2-[4-(4-methylpiperazin-1-yl)-butylamino]-ethenesulfonyl}-quinazolin-4-yl)-amine;

But-2-enedioic acid [4-(3-bromo-phenylamino)quinazolin-6-yl]-amide (3-dimethylamino-propyl)-amide;

But-2-enedioic acid [4-(3-bromo-phenylamino)quinazolin-6-yl]-amide (3-imidazol-1-yl-propyl)-amide;

4,4-Difluoro-8-morpholin-4-yl-oct-2-enoic acid [4-(3-bromo-phenylamino)-quinazolin-6-yl]-amide;

8-Dimethylamino-4,4-difluoro-oct-2-enoic acid [4-(3-bromo-phenylamino)-quinazolin-6-yl]-amide;

7-Dimethylamino-4,4-difluoro-hept-2-enoic acid [4-(3-bromo-phenylamino)-quinazolin-6-yl]-amide;

4,4-Difluoro-7-morpholin-4-yl-hept-2-enoic acid [4-(3-bromo-phenylamino)-quinazolin-6-yl]-amide;

6-Dimethylamino-hex-2-ynoic acid [4-(3-bromophenylamino)-quinazolin-6-yl]-amide;

6-Morpholin-4-yl-hex-2-ynoic acid [4-(3-bromophenylamino)-quinazolin-6-yl]-amide;

7-Dimethylamino-hept-2-ynoic acid [4-(3-bromophenylamino)-quinazolin-6-yl]-amide;

7-Morpholin-4-yl-hept-2-ynoic acid [4-(3-bromo-phenylamino)-quinazolin-6-yl]-amide;

5-Dimethylamino-pent-2-ynoic acid [4-(3-bromophenylamino)-quinazolin-6-yl]-amide;

5-Morpholin-4-yl-pent-2-ynoic acid [4-(3-bromophenylamino)-quinazolin-6-yl]-amide;

5-Imidazol-1-yl-pent-2-ynoic acid [4-(3-bromophenylamino)-quinazolin-6-yl]-amide;

5-(4-Methyl-piperazin-1-yl)-pent-2-ynoic acid [4-(3-bromo-phenylamino)-quinazolin-6-yl]-amide;

4-[4-(3-Bromo-phenylamino)-quinazolin-6-ylcarbamoyl]-but-3-enoic acid 2-(4-methylpiperazin-1-yl)-ethyl ester;

4-[4-(3-Bromo-phenylamino)-quinazolin-6ylcarbamoyl]-but-3-enoic acid 2-imidazol-1-yl-ethyl ester;

Pent-2-enedioic acid 1-{[4-(3-bromo-phenylamino)quinazolin-6-yl]-amide} 5-[(3-morpholin-4-yl-propyl)-amide];

Pent-2-enedioic acid 1-{[4-(3-bromo-phenylamino)quinazolin-6-yl]-amide} 5-[(3-diethylamino-propyl)-amide];

4-[4-(3-Bromo-phenylamino)-quinazolin-6-ylcarbamoyl]-but-3-enoic acid 2-morpholin-4-yl-ethyl ester;

Pent-2-enedioic acid 1-{[4-(3-bromo-phenylamino)quinazolin-6-yl]-amide} 5-{[3-(4-methyl-piperazin1-yl)-propyl]-amide};

3-[4-(1-Phenyl-ethylamino)-pyrido[3,4-d]pyrimidin6-ylcarbamoyl]-acrylic acid 2-morpholin-4-yl-ethyl ester;

But-2-enedioic acid (4-imidazol-1-yl-butyl)-amide [4-(1-phenyl-ethylamino)-pyrido[3,4-d]pyrimidin-6-yl]-amide;

4-[4-(1-Phenyl-ethylamino)-pyrido[3,4-d]pyrimidin-6-ylcarbamoyl]-but-3-enoic acid 3-diethylamino-propyl ester;

Pent-2-enedioic acid 5-{[2-(4-methyl-piperazin1-yl)-ethyl]-amide} 1-{[4-(1-phenyl-ethylamino)pyrido[3,4-d]pyrimidin-6-yl]-amide};

4,4-Difluoro-7-morpholin-4-yl-hept-2-enoic acid [4-(1-phenyl-ethylamino)-pyrido[3,4-d]pyrimidin-6-yl]-amide;

7-Dimethylamino-4,4-difluoro-hept-2-enoic acid [4-(1-phenyl-ethylamino)-pyrido[3,4-d]pyrimidin-6-yl]-amide;

7-Imidazol-1-yl-hept-2-ynoic acid [4-(1-phenylethylamino)-pyrido[3,4-d]pyrimidin-6-yl]-amide;

6-Dimethylamino-hex-2-ynoic acid [4-(1-phenylethylamino)-pyrido[3,4-d]pyrimidin-6-yl]-amide;

But-2-endioic acid [4-(3-chloro-4fluorophenylamino)-7-fluoroquinazolin-6-yl]-amide (3-dimethylaminopropyl)amide;

But-2-endioic acid [7-chloro-4-(3-chloro-4fluorophenylamino))quinazolin-6-yl]-amide (3-dimethylaminopropyl)amide;

N-[4-[3-(Bromophenyl)amino]-5-fluoro-7-[3-(4morpholino)propoxy]quinazolin-6-yl]-acrylamide; and N-[4-[(3-(Chloro-4-fluorophenyl)amino]-5-fluoro-7-(1, N-imidazoyl)propoxy]quinazolin-6-yl]acrylamide.

DETAILED DESCRIPTION OF THE INVENTION

The present invention provides compounds having the Formula I

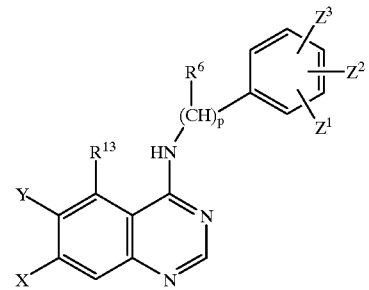

wherein X is —D—E—F, and Y is —SR$^4$, halogen, —OR$^4$, —NHR$^3$, or hydrogen, or X is —SR$^4$, halogen, —OR$^4$, —NHR$^3$, or hydrogen, and Y is —D—E—F;

D is 
$$-\underset{\underset{}{}}{\overset{R^2}{N}}-,\ -O-,\ -\underset{\underset{H}{}}{\overset{R^2}{C}}-,\ -\underset{}{\overset{R^2}{N}}-\underset{}{\overset{H}{N}}-,$$

$$-\underset{}{\overset{R^2}{N}}-O-,\ -\underset{\underset{H}{}}{\overset{R^2}{C}}-\underset{\underset{H}{}}{\overset{}{N}}-,\ -\underset{\underset{H}{}}{\overset{R^2}{C}}-O-,$$

$$-\underset{\underset{H}{}}{\overset{R^2}{C}}-\underset{\underset{H}{}}{\overset{H}{C}}-,\ -\underset{\underset{H}{}}{\overset{}{N}}-\underset{\underset{H}{}}{\overset{R^2}{C}}-,\ -O-\underset{\underset{H}{}}{\overset{R^2}{C}}-,$$

-continued

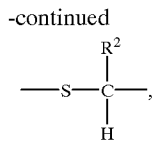

or absent;

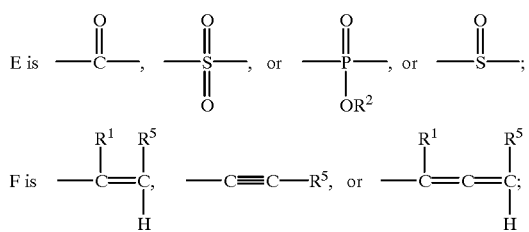

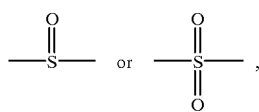

provided that when E is

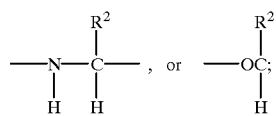

D is not

R¹ is hydrogen, halogen, or $C_1$–$C_6$ alkyl;

R², R³, and R⁴ are independently hydrogen, $C_1$–$C_6$ alkyl, —$(CH_2)_n$-N-piperidinyl, —$(CH_2)_n$-N-piperazinyl, —$(CH_2)_n$-$N_1$-piperazinyl[N—$C_1$–$C_6$)alkyl], —$(CH_2)_n$-N-pyrrolidyl, —$(CH_2)_n$-pyridinyl, —$(CH_2)_n$-N-imidazoyl, —$(CH_2)_n$-imidazoyl, —$(CH_2)_n$-N-morpholino, —$(CH_2)_n$-N-thiomorpholino, —$(CH_2)_n$-N-hexahydroazepine or substituted $C_1$–$C_6$ alkyl, wherein the substituents are selected from —OH, —$NH_2$, or $$-\!\!-\!\!\overset{A}{\underset{}{N}}\!\!-\!\!B,$$

A and B are independently hydrogen, $C_1$–$C_6$ alkyl, —$(CH_2)_n$OH, —$(CH_2)_n$-N-piperidinyl, —$(CH_2)_n$-N-piperazinyl, —$(CH_2)_n$-$N_1$-piperazinyl[$N_4$-($C_1$–$C_6$ alkyl)], —$(CH_2)_n$-N-pyrrolidyl, —$(CH_2)_n$-N-pyridyl, —$(CH_2)_n$-imidazoyl, or —$(CH_2)_n$-N-imidazoyl;

Z¹, Z², or Z³ are independently hydrogen, halogen, $C_1$–$C_6$ alkyl, $C_3$–$C_8$ cycloalkyl, $C_1$–$C_6$ alkoxy, $C_3$–$C_8$ cycloalkoxy, nitro, $C_1$–$C_6$ perfluoroalkyl, hydroxy, $C_1$–$C_6$ acyloxy, —$NH_2$, —NH($C_1$–$C_6$ alkyl), —N($C_1$–$C_6$ alkyl)$_2$, —NH($C_3$–$C_8$ cycloalkyl), —N($C_3$–$C_8$ cycloalkyl)$_2$, hydroxymethyl, $C_1$–$C_6$ acyl, cyano, azido, $C_1$–$C_6$ thioalkyl, $C_1$–$C_6$ sulfinylalkyl, $C_1$–$C_6$ sulfonylalkyl, $C_3$–$C_8$ thiocycloalkyl, $C_3$–$C_8$ sulfinylcycloalkyl, $C_3$–$C_8$ sulfonylcycloalkyl, mercapto, $C_1$–$C_6$ alkoxycarbonyl, $C_3$–$C_8$ cycloalkoxycarbonyl, $C_2$–$C_4$ alkenyl, $C_4$–$C_8$ cycloalkenyl, or $C_2$–$C_4$ alkynyl;

R⁵ is hydrogen, halogen, $C_1$–$C_6$-perfluoroalkyl, 1,1-difluoro($C_1$–$C_6$)alkyl, $C_1$–$C_6$ alkyl, —$(CH_2)_n$-N-piperidinyl, —$(CH_2)_n$-piperazinyl, —$(CH_2)_n$-piperazinyl[$N_4$-($C_1$–$C_6$)alkyl], —$(CH_2)_n$-N-pyrrolidyl, —$(CH_2)_n$-pyridinyl, —$(CH_2)_n$-N-imidazoyl, —$(CH_2)_n$-N-morpholino, —$(CH_2)_n$-N-thiomorpholino,

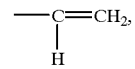

—CH=CH—($C_1$–$C_6$)alkyl, —$(CH_2)_n$-N-hexahydroazepine, —$(CH_2)_n$$NH_2$, —$(CH_2)_n$NH($C_1$–$C_6$ alkyl), —$(CH_2)_n$N($C_1$–$C_6$ alkyl)$_2$, -1-oxo($C_1$–$C_6$)alkyl, carboxy, ($C_1$–$C_6$)alkyloxycarbonyl, N-($C_1$–$C_6$)alkylcarbamoyl, phenyl or substituted phenyl, wherein the substituted phenyl can have from one to three substituents independently selected from Z¹, Z², Z³ or a monocyclic heteroaryl group, and each $C_1$–$C_6$ alkyl group can be substituted with —OH, —$NH_2$ or —NAB, where A and B are as defined above, R⁶ is hydrogen or $C_1$–$C_6$ alkyl; R¹³ is hydrogen or halogen; and n is 1 to 4, p is 0 or 1, and the pharmaceutically acceptable salts, esters, amides and prodrugs thereof.

In another embodiment, present invention also provides compounds having the Formula II

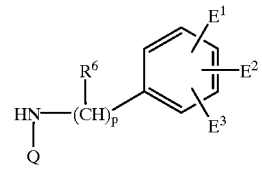

wherein Q is

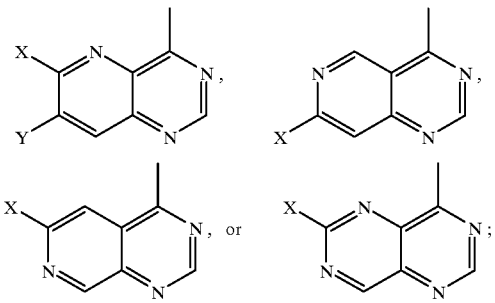

p is 0 or 1;

X is —D—E—F and Y is —SR⁴, —OR⁴, —NHR³ or hydrogen, or X is —SR⁴, —OR⁴, —NHR³ or hydrogen, and Y is —D—E—F;

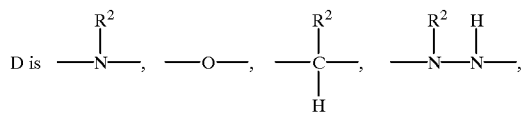

-continued

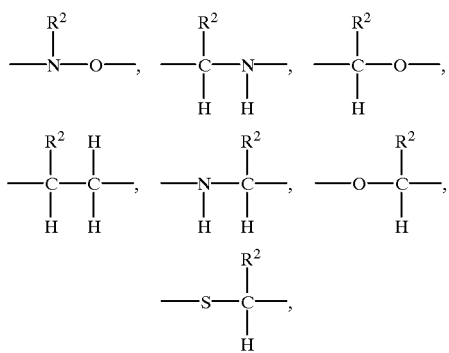

or absent;

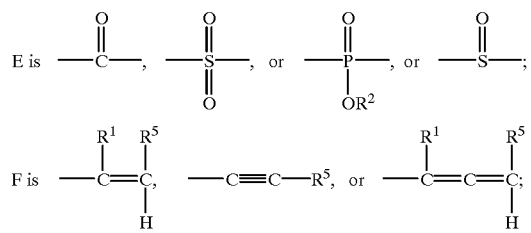

provided that when E is

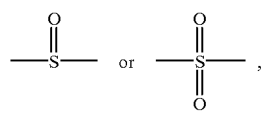

D is not

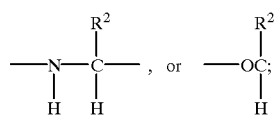

$R^1$ is hydrogen, halogen, or $C_1$–$C_6$ alkyl;

$R^2$, $R^3$, and $R^4$ are independently hydrogen, $C_1$–$C_6$ alkyl, —$(CH_2)_n$-N-piperidinyl, —$(CH_2)_n$-N-piperazinyl, —$(CH_2)_n$-$N_1$-piperazinyl[$N_4$-($C_1$–$C_6$)alkyl]), —$(CH_2)_n$-N-pyrrolidyl, —$(CH_2)_n$-pyridinyl, —$(CH_2)_n$-N-imidazoyl, —$(CH_2)_n$-N-morpholino, —$(CH_2)_n$-N-thiomorpholino, —$(CH_2)_n$-N-hexahydroazepine or substituted $C_1$–$C_6$ alkyl, wherein the substituents are selected from —OH, —$NH_2$, or

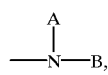

A and B are independently hydrogen, $C_1$–$C_6$ alkyl, —$(CH_2)_n$OH, —$(CH_2)_n$-N-piperidinyl, —$(CH_2)_n$-N-piperazinyl, —$(CH_2)_n$-$N_1$-piperazinyl[$N_4$-($C_1$–$C_6$) alkyl], —$(CH_2)_n$-N-pyrrolidyl, —$(CH_2)_n$-N-pyridyl, —$(CH_2)_n$-imidazoyl, or —$(CH_2)_n$-N-imidazoyl;

$E^1$, $E^2$, and $E^3$ are independently halogen, $C_1$–$C_6$ alkyl, $C_3$–$C_8$ cycloalkyl, $C_1$–$C_6$ alkoxy, $C_3$–$C_8$ cycloalkoxy, nitro, $C_1$–$C_6$ perfluoroalkyl, hydroxy, $C_1$–$C_6$ acyloxy, —$NH_2$, —NH($C_1$–$C_6$ alkyl), —N($C_1$–$C_6$ alkyl)$_2$, —NH($C_3$–$C_8$ cycloalkyl), —N($C_3$–$C_8$ cycloalkyl)$_2$, hydroxymethyl, $C_1$–$C_6$ acyl, cyano, azido, $C_1$–$C_6$ thioalkyl, $C_1$–$C_6$ sulfinylalkyl, $C_1$–$C_6$ sulfonylalkyl, $C_3$–$C_8$ thiocycloalkyl, $C_3$–$C_8$ sulfinylcycloalkyl, $C_3$–$C_8$ sulfonylcycloalkyl, mercapto, $C_1$–$C_6$ alkoxycarbonyl, $C_3$–$C_8$ cycloalkoxycarbonyl, $C_2$–$C_4$ alkenyl, $C_4$–$C_8$ cycloalkenyl, or $C_2$–$C_4$ alkynyl;

$R^5$ is hydrogen, halogen, $C_1$–$C_6$-perfluoroalkyl, 1,1-difluoro($C_1$–$C_6$)alkyl, $C_1$–$C_6$ alkyl, —$(CH_2)_n$-N-piperidinyl, —$(CH_2)_n$-piperazinyl, —$(CH_2)_n$-piperazinyl[$N_4$-($C_1$–$C_6$)alkyl], —$(CH_2)_n$-N-pyrrolidyl, —$(CH_2)_n$-pyridinyl, —$(CH_2)_n$-N-imidazoyl, —$(CH_2)_n$-N-morpholino, —$(CH_2)_n$-N-thiomorpholino,

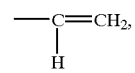

—CH=CH—($C_1$–$C_6$)alkyl, —$(CH_2)_n$-N-hexahydroazepine, —$(CH_2)_nNH_2$, —$(CH_2)_nNH(C_1$–$C_6$ alkyl), —$(CH_2)_nN(C_1$–$C_6$ alkyl)$_2$, -1-oxo($C_1$–$C_6$)alkyl, carboxy, ($C_1$–$C_6$)alkyloxycarbonyl, N-($C_1$–$C_6$) alkylcarbamoyl, phenyl or substituted phenyl, wherein the substituted phenyl can have from one to three substituents independently selected from $Z^1$, $Z^2$, $Z^3$ or a monocyclic heteroaryl group, and each $C_1$–$C_6$ alkyl group can be substituted with —OH, —$NH_2$ or —NAB, where A and B are as defined above, $R^6$ is hydrogen or $C_1$–$C_6$ alkyl; and n is 1 to 4, p is 0 or 1, and the pharmaceutically acceptable salts, esters, amides, and prodrugs thereof.

In another embodiment, the present invention provides compounds having the Formula III

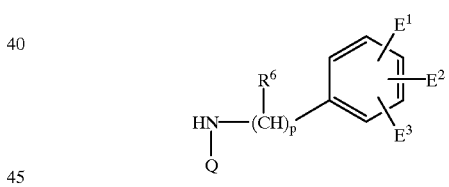

wherein Q is

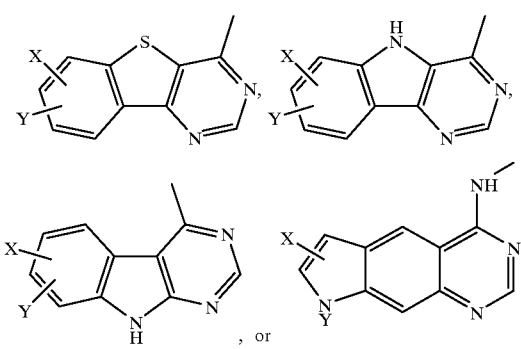

, or ;

p is 0 or 1;

X is —D—E—F, and Y is —$SR^4$, —$OR^4$, —$NHR^3$ or hydrogen, or X is —$SR^4$, —$OR^4$, —$NHR^3$ or hydrogen, and Y is —D—E—F;

D is 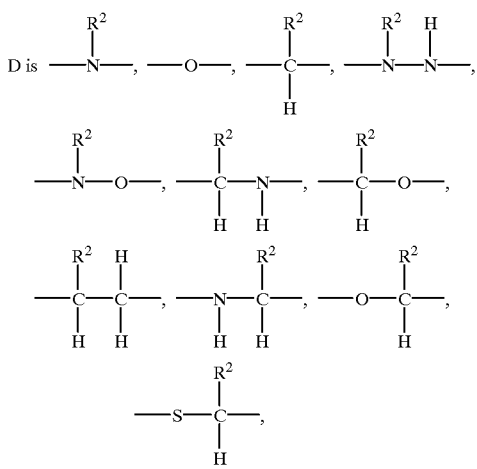

or absent;

E is 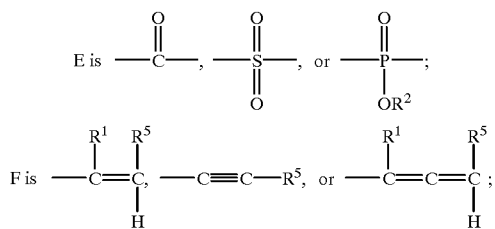

F is 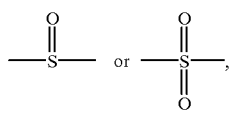

provided that when E is

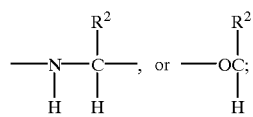

D is not

$R^1$ is hydrogen, halogen, or $C_1-C_6$ alkyl;

$R^2$, $R^3$, and $R^4$ are independently hydrogen, $C_1-C_6$ alkyl, —$(CH_2)_n$-N-piperidinyl, —$(CH_2)_n$-N-piperazinyl, —$(CH_2)_n$-$N_1$-piperazinyl[$N_4$-($C_1-C_6$)alkyl], —$(CH_2)_n$-N-pyrrolidyl, —$(CH_2)_n$-pyridinyl, —$(CH_2)_n$-N-imidazoyl, —$(CH_2)_n$-imidazoyl, —$(CH_2)_n$-N-morpholino, —$(CH_2)_n$-N-thiomorpholino, —$(CH_2)_n$-N-hexahydroazepine or substituted $C_1-C_6$ alkyl, wherein the substituents are selected from —OH, —$NH_2$, or

—N(A)—B,

A and B are independently hydrogen, $C_1-C_6$ alkyl, —$(CH_2)_n$OH, —$(CH_2)_n$-N-piperidinyl, —$(CH_2)_n$-N-piperazinyl, —$(CH_2)_n$-$N_1$-piperazinyl[$N_4$-($C_1-C_6$ alkyl)], —$(CH_2)_n$-N-pyrrolidyl, —$(CH_2)_n$-N-pyridyl, —$(CH_2)_n$-imidazoyl, or —$(CH_2)_n$-N-imidazoyl;

$E^1$, $E^2$, and $E^3$ are independently halogen, $C_1-C_6$ alkyl, $C_3-C_8$ cycloalkyl, $C_1-C_6$ alkoxy, $C_3-C_8$ cycloalkoxy, nitro, $C_1-C_6$ perfluoroalkyl, hydroxy, $C_1-C_6$ acyloxy, —$NH_2$, —NH($C_1-C_6$ alkyl), —N($C_1-C_6$ alkyl)$_2$, —NH($C_3-C_8$ cycloalkyl), —N($C_3-C_8$ cycloalkyl)$_2$, hydroxymethyl, $C_1-C_6$ acyl, cyano, azido, $C_1-C_6$ thioalkyl, $C_1-C_6$ sulfinylalkyl, $C_1-C_6$ sulfonylalkyl, $C_3-C_8$ thiocycloalkyl, $C_3-C_8$ sulfinylcycloalkyl, $C_3-C_8$ sulfonylcycloalkyl, mercapto, $C_1-C_6$ alkoxycarbonyl, $C_3-C_8$ cycloalkoxycarbonyl, $C_2-C_4$ alkenyl, $C_4-C_8$ cycloalkenyl, or $C_2-C_4$ alkynyl;

$R^5$ is hydrogen, halogen, $C_1-C_6$-perfluoroalkyl, 1,1-difluoro($C_1-C_6$)alkyl, $C_1-C_6$ alkyl, —$(CH_2)_n$-N-piperidinyl, —$(CH_2)_n$-piperazinyl, —$(CH_2)_n$-piperazinyl[$N_4$-($C_1-C_6$)alkyl], —$(CH_2)_n$-N-pyrrolidyl, —$(CH_2)_n$-pyridinyl, —$(CH_2)_n$-N-imidazoyl, —$(CH_2)_n$-N-morpholino, —$(CH_2)_n$-N-thiomorpholino,

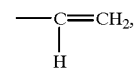

—CH=CH—($C_1-C_6$)alkyl, —$(CH_2)_n$-N-hexahydroazepine, —$(CH_2)_n NH_2$, —$(CH_2)_n$NH($C_1-C_6$ alkyl), —$(CH_2)_n$N($C_1-C_6$ alkyl)$_2$, -1-oxo($C_1-C_6$)alkyl, carboxy, ($C_1-C_6$)alkyloxycarbonyl, N—($C_1-C_6$) alkylcarbamoyl, phenyl or substituted phenyl, wherein the substituted phenyl can have from one to three substituents independently selected from $Z^1$, $Z^2$, $Z^3$ or a monocyclic heteroaryl group, and each $C_1-C_6$ alkyl group can be substituted with —OH, —$NH_2$ or —NAB, where A and B are as defined above, $R^6$ is hydrogen or $C_1-C_6$ alkyl; and n is 1 to 4, and the pharmaceutically acceptable salts, esters, amides, and prodrugs thereof.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "alkenyl" means a branched or straight chain hydrocarbon having one or more carbon-carbon double bond.

The term "cycloalkyl" means a cyclic hydrocarbon. Examples of cycloalkyl groups include cyclopropyl, cyclobutyl, cyclopentyl, and cyclohexyl.

The term "cycloalkoxy" means a cycloalkyl group attached to an oxygen atom.

The term "perfluoroalkyl" means an alkyl group in which all the hydrogen atoms have been replaced by fluorine atoms.

The term "acyl" means a group derived from an organic acid by removal of the hydroxy group (—OH).

The term "acyloxyl" means an acyl group attached to an oxygen atom.

The term "thioalkyl" means an alkyl group attached to a sulfur atom.

The term "sulfinylalkyl" means a sulfinyl group attached to an alkyl group.

The term "sulfonylalkyl" means a sulfonyl group attached to an alkyl group.

The term "thiocycloalkyl" means a cycloalkyl group attached to a sulfur atom.

The term "sulfinylcycloalkyl" means a sulfinyl group attached to a cycloalkyl group.

The term "sulfonylcycloalkyl" means a sulfonyl group attached to a cycloalkyl group.

The term "mercapto" means a —SH group.

The term "alkoxycarbonyl" means an alkoxy group attached to a carbonyl group.

The term "cycloalkoxycarbonyl" means a cycloalkyoxy group attached to a carbonyl group.

The term "cycloalkenyl" means a cyclic hydrocarbon containing one or more carbon-carbon double bond.

The term "alkynyl" means a hydrocarbon having one or more carbon-carbon triple bond.

The term "monocyclic heteroaryl" mean a heterocyclic aryl compound having only one ring structure. The cyclic compound is aromatic and contains one or more heteroatom. Examples of heteroatoms include, but are not limited to, nitrogen, oxygen, sulfur, and phosphorus. Examples of monocyclic heteroaryl groups include, but are not limited to, pyridyl, thienyl, and imidazoyl.

The symbol "-" represents a covalent bond.

The compounds of Formulas I, II, and III are irreversible inhibitors of tyrosine kinases, particularly EGF tyrosine kinase. A therapeutically effective amount of the compounds of Formula I, II, or III can be administered to a patient having cancer or a patient having restenosis or at risk of having restenosis or a patient having psoriasis, atherosclerosis, or endometriosis. Those skilled in the art are readily able to identify patients having cancer, restenosis, psoriasis, atherosclerosis, or endometriosis, and patients who are at risk of developing restenosis. The term "patient" means animals such as dogs, cats, cows, sheep, and also includes humans.

The compounds of the present invention can be administered to humans and animals either orally, rectally, parenterally (intravenously, intramuscularly or subcutaneously), intracisternally, intravaginally, intraperitoneally, intravesically, locally (powders, ointments, or drops), or as a buccal or nasal spray. The compounds can be administered alone or as part of a pharmaceutically acceptable composition that includes pharmaceutically acceptable excipients. It is noted that more than one compound of Formula I, II, III can be administered either concurrently or sequentially.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar, as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine and the like (see, for example, S. M. Berge, et al., "Pharmaceutical Salts," *J Pharm Sci*, 1977;66:1–19 which is incorporated herein by reference).

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

The compounds of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well-known to those skilled in the art.

The compounds of the present invention can exist in different stereoisometric forms by virtue of the presence of asymmetric centers in the compounds. It is contemplated that all stereoisometric forms of the compounds as well as mixtures thereof, including racemic mixtures, form part of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

It is intended that the compounds of Formula I, II, or III be either synthetically produced or biologically produced.

The following examples illustrate particular embodiments of the invention and are not intended to limit the specification, including the claims, in any manner.

GENERAL SYNTHETIC SCHEMES

Amine-Linked Alkylating Michael Acceptor Sidechains

The amine is acylated either by an acid in the presence of a coupling agent such as EDAC, or by an acid chloride. The amine in turn can be made by reduction of the corresponding nitro compound, displacement of a halogen by an amine or ammonia equivalent, or in the case of pyrido[4,3-d] pyrimidines by direct incorporation during the synthesis. 2-Haloalkylsulfonyl halides form vinyl sulfonamides when treated with the aryl amine and excess tertiary amine base.

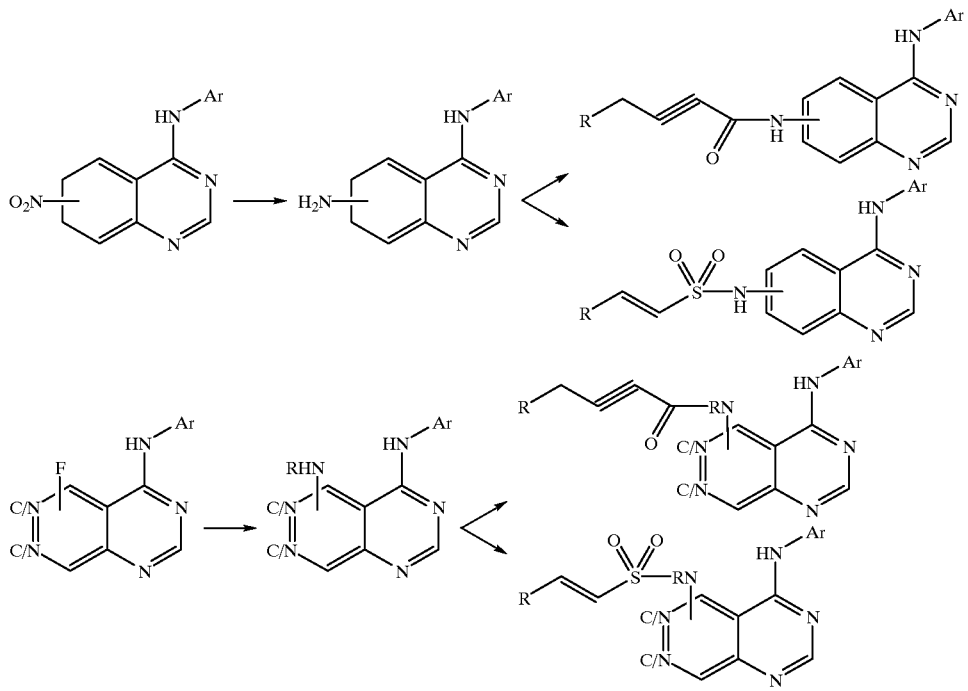

C/N means either a carbon or nitrogen atom is present at that location.

means a bond or no bond.

Oxygen-Linked Alkylating Michael Acceptor Sidechains

The hydroxyl group is acylated either by an acid in the presence of a coupling agent such as EDAC, or by an acid chloride. The hydroxyl compound can in turn can be made by cleavage of the corresponding methyl ether. 3-Methylthioalkanoic acid or their acid chlorides can be used to acylate the oxygen followed by S-alkylation or oxidation and basic or thermal elimination.

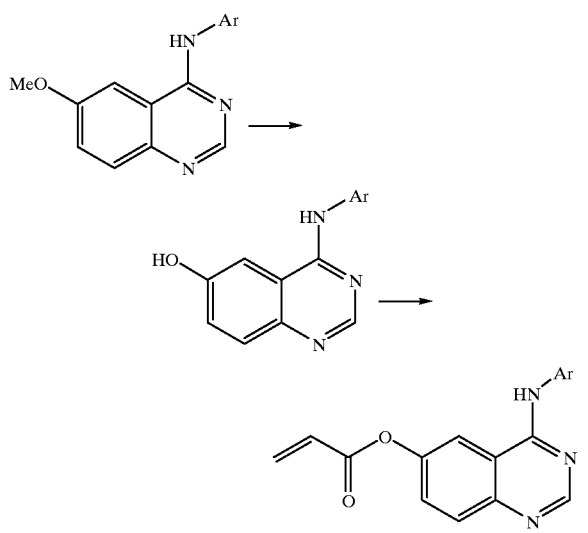

-continued

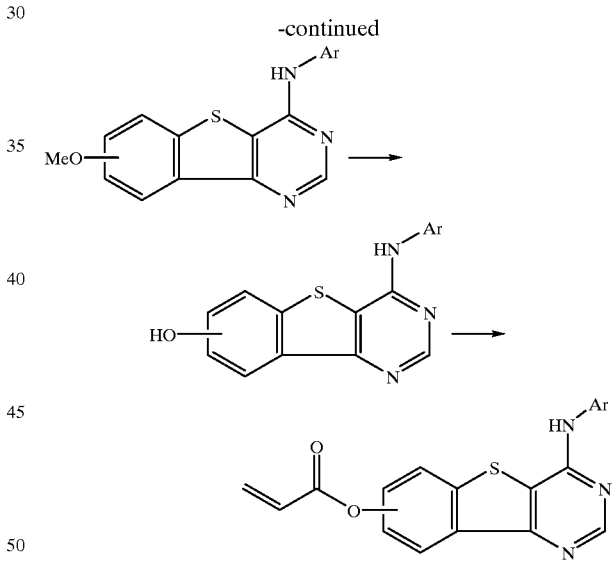

Ar and R denote an aryl group and R denotes an organic group as exemplified herein.

Carbon-Linked Alkylating Michael Acceptor Sidechains

A Stille or Suzuki coupling can be used to couple the sidechain to an appropriately substituted quinazoline/pyridopyrimidine/pyrimidinopyrimidine/tricycle. These in turn can be made as aryl halides by methods known in the art, or as aryl triflates by triflation of the hydroxyl compounds described above, as aryl stannanes by reaction of the abovementioned triflates with hexamethyl distannane, or as arylboronic acids by conversion of aryl iodides to arylorganometallics, followed by treatment with borate esters and hydrolysis. Alternatively, aryl iodides can be converted to the arylzinc species and coupled with activated halides.

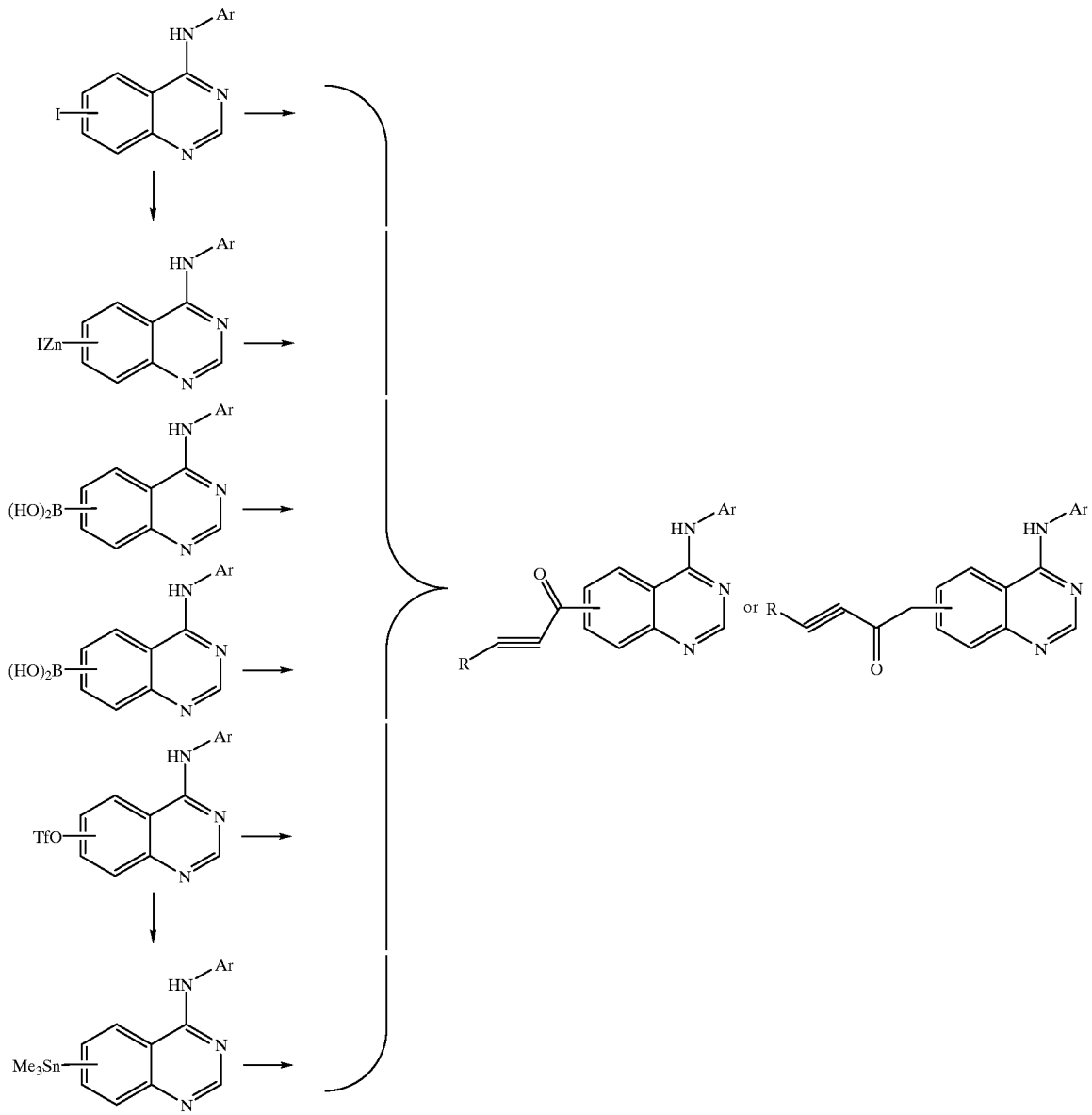

Sulfur-Linked Alkylating Michael Acceptor Sidechains

Activated halides in pyridopyrimidines and pyrimidinopyrimidines can be displaced by suitable 2-hydroxythiolates, and these in turn can be oxidized to sulfones, and then water eliminated by treatment with mesyl chloride and several equivalents of a base. For quinazolines, and claimed tricycles, either an activated halogen especially fluorine can be used in the sequence just described for pyridopyrimidines, or an aryl iodide precursor can be metalated, quenched with sulfur or a suitable sulfur electrophilic progenitor and then the resultant aryl thiol used to open a terminal epoxide, giving a 2-hydroxy thioether which can be converted onto a vinyl sulfone by oxidation and water elimination as described above.

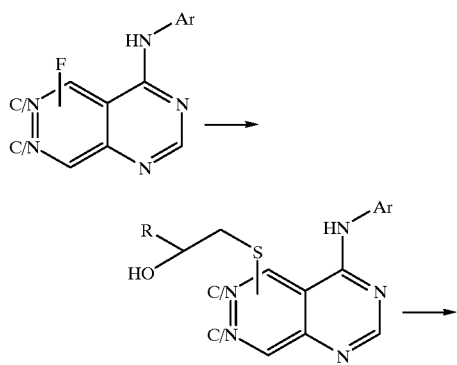

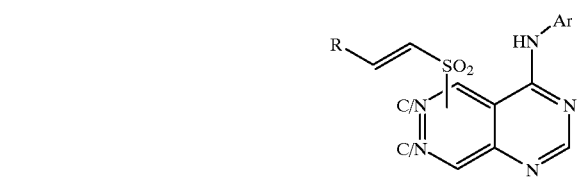
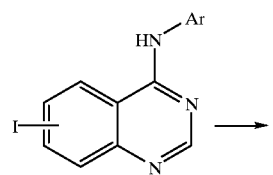

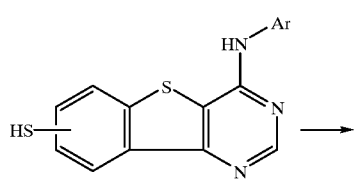
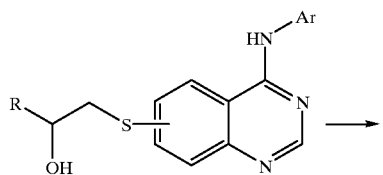

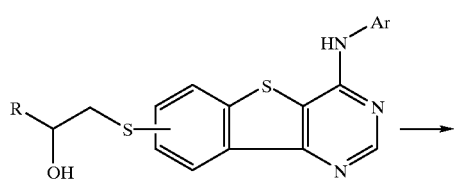
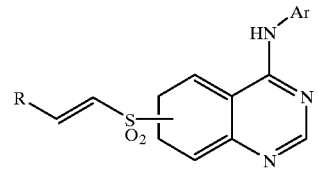

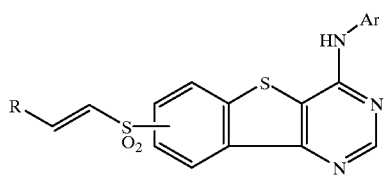

Hydrazing-Linked Alkylating Michael Acceptor Sidechains

Activated halides in pyridopyrimidines and pyrimidinopyrimidines and appropriately substituted quinazolines can be displaced by a (N-alkyl) hydrazine. Alternatively, an amino-derivative of the desired ring nucleus can be diazotized, and then reduced to the hydrazine. The distal nitrogen of the hydrazine can then be acylated, sulfonylated or phosphorylated, by methods well-known to one skilled in the art.

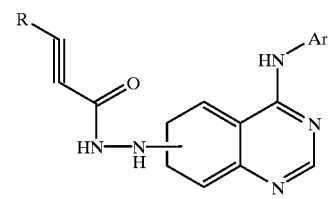

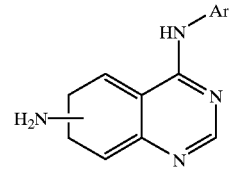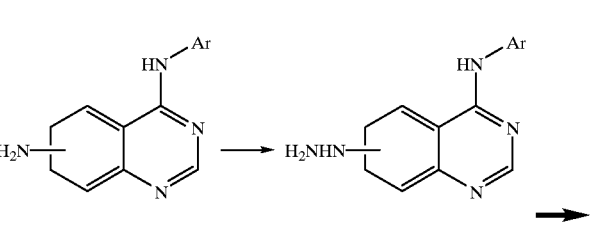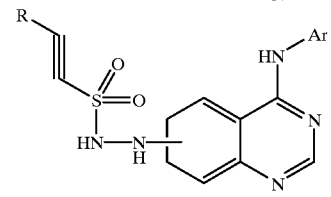

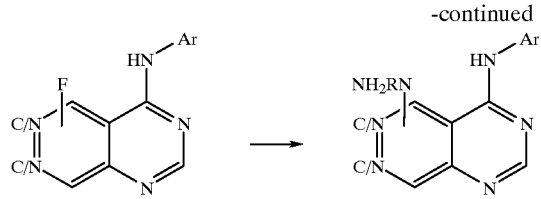
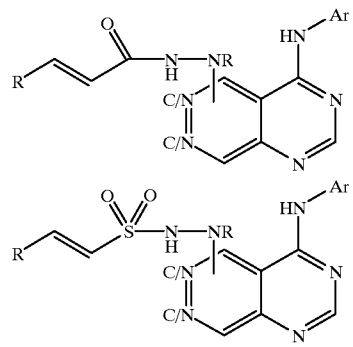

Hydroxylamino-O-Linked Alkylating Michael Acceptor Sidechains

Activated halides in pyridopyrimidines and pyrimidinopyrimidines and appropriately substituted quinazolines can be displaced by a suitably O-protected (N-alkyl) hydroxylamine. Alternatively, a nitroderivative of the desired ring nucleus can be synthesized, and then reduced to the hydroxylamine under appropriate mildly reducing conditions. The oxygen of the hydroxylamine can then be acylated, sulfonylated or phosphorylated, by methods well-known to one skilled in the art.

Methyleneamino-N-Linked Alkylating Michael Acceptor Sidechains

Activated halides in pyridopyrimidines and pyrimidinopyrimidines and appropriately substituted quinazolines can be displaced by cyanide, preferably in the presence of copper or nickel salt catalysis. Alternatively, an amino-derivative of the desired ring nucleus can be diazotized, and then converted to the nitrile as described above. In some cases, the nitrile functionality can be incorporated into the heterocycle earlier in the synthesis, either as itself, or via a carboxylic acid or aldehyde, both of which can readily be

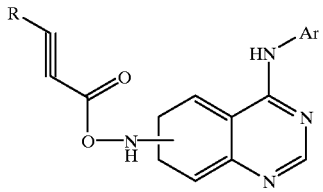
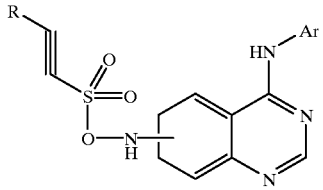
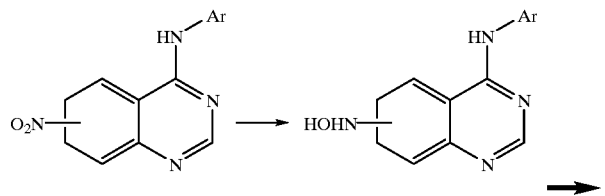
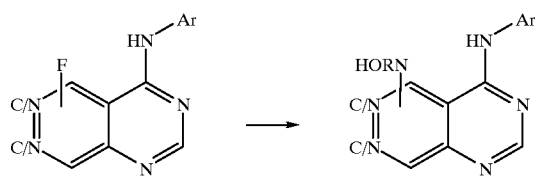
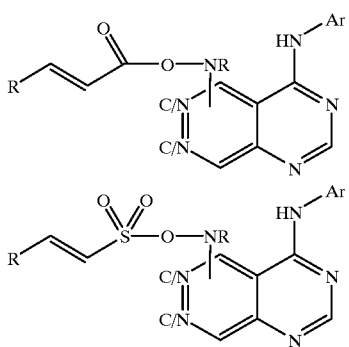

turned into nitrile compounds by one skilled in the art. Reduction of the nitrile to a methyleneamine is followed by nitrogen acylation, sulfonylation or phosphorylation, by methods well-known to one skilled in the art.

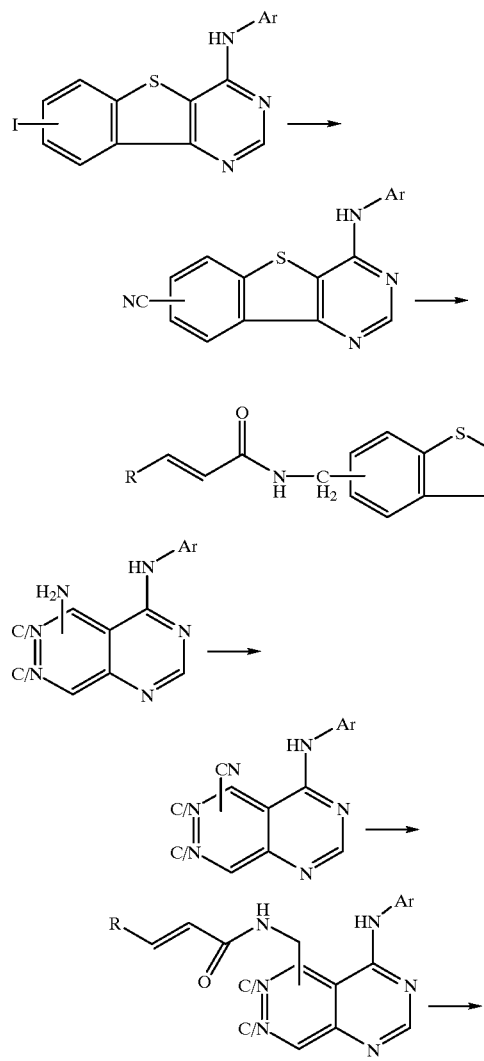

Methyleneoxy-O-Linked Alkylating Michael Acceptor Sidechains

Hydroxymethyl compounds can be incorporated into appropriate heterocycles in many ways obvious to one skilled in the art. For example, iodoquinazolines may be carbonylated in a Heck reaction, and then reduced with NaBH$_4$ to the desired precursor. Aminopyridopyrimidines may be diazotized, converted to the nitrile, partially reduced to an imine, hydrolysed, and the resultant aldehyde reduced to hydroxymethyl. The oxygen of the hydroxymethyl can then be acylated, sulfonylated or phosphorylated, by methods well-known to one skilled in the art.

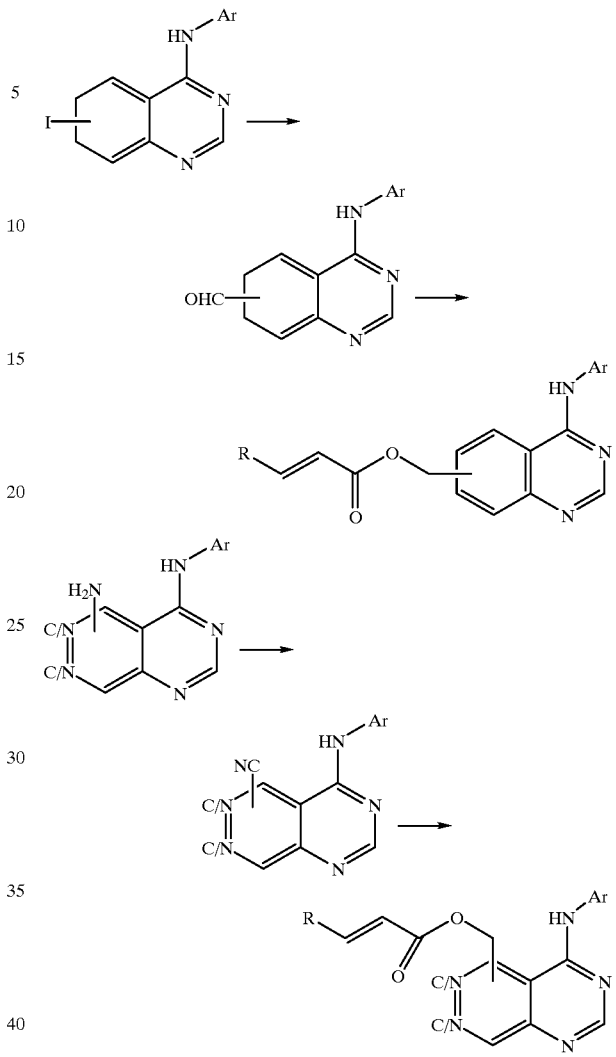

Ethano-Linked Alkylating Michael Acceptor Sidechains

Michael addition of a cuprate, derived via an organozincate from an iodoquinazoline, to a divinylketone, or appropriately mono-masked derivative, followed by unmasking of the second unsaturated functionality, if required, will give compounds of the desired type. Aldehydes derived from pyridopyrimidines or pyrimidopyrimidnes as described above can be homologated to the desired compounds by a wide variety of techniques such as the one illustrated, by one skilled in the art.

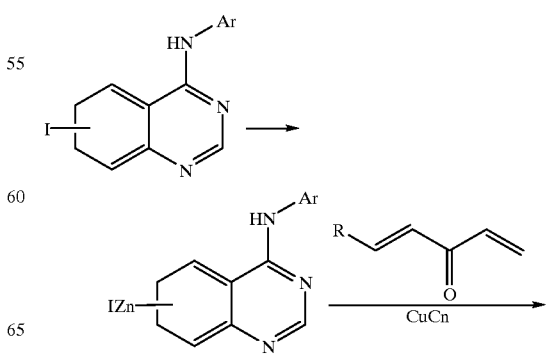

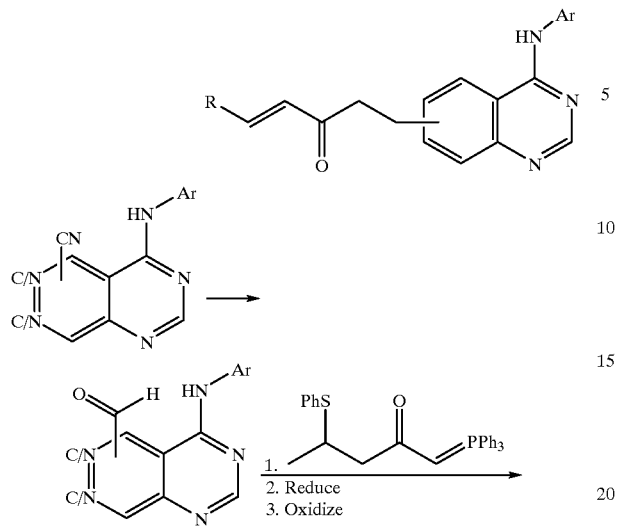

Aminomethyl-C-Linked Alkylating Michael Acceptor Sidechains

Amino-heterocycles of the type described throughout this application can be alkylated by various double bond-masked equivalents of 1-bromobut-3-en-2-one, followed by unmasking of the unsaturation by methods known to one skilled in the art.

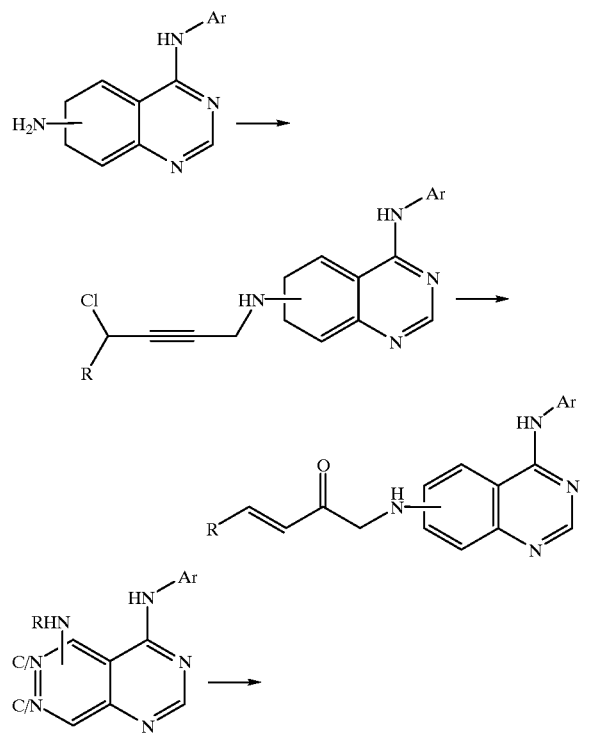

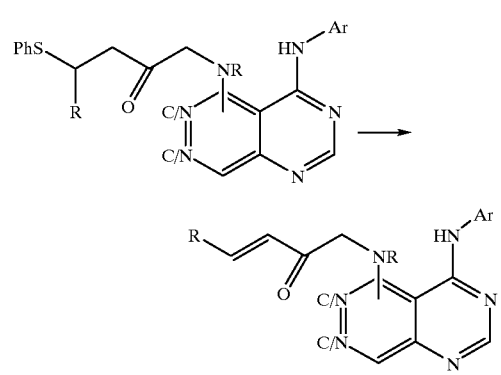

Hydroxymethyl-C-Linked Alkylating Michael Acceptor Sidechains

Hydroxy-heterocycles made as described previously from methoxy-heterocycles can be alkylated by various double bond-masked equivalents of 1-bromobut-3-en-2-one, followed by unmasking of the unsaturation by methods known to one skilled in the art. Alternatively, alkylation of the phenol can be accomplished with chloroacetic acid, followed by conversion to an acyl chloride and Stille coupling of that acyl halide with an appropriate alkenyl stannane.

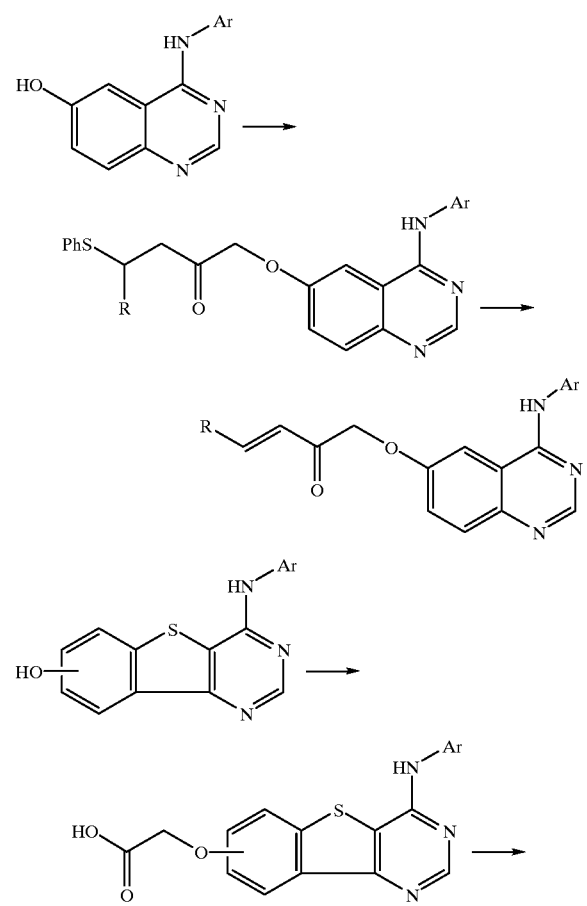

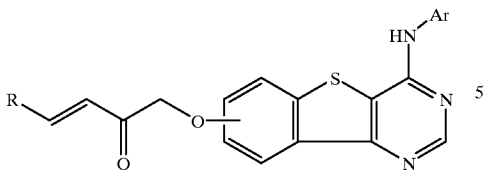

Thiomethyl-C-Linked Alkylating Michael Acceptor Sidechains

Appropriate mercapto-heterocycles, made by displacement of activated halides on the heteroaromatic ring, can be alkylated by various double bond-masked equivalents of 1-bromobut-3-en-2-one, followed by unmasking of the unsaturation by methods known to one skilled in the art. Alternatively, alkylation of the thiol can be accomplished with chloroacetic acid, followed by conversion to an acyl chloride and Stille coupling of that acyl halide with an appropriate alkenyl stannane.

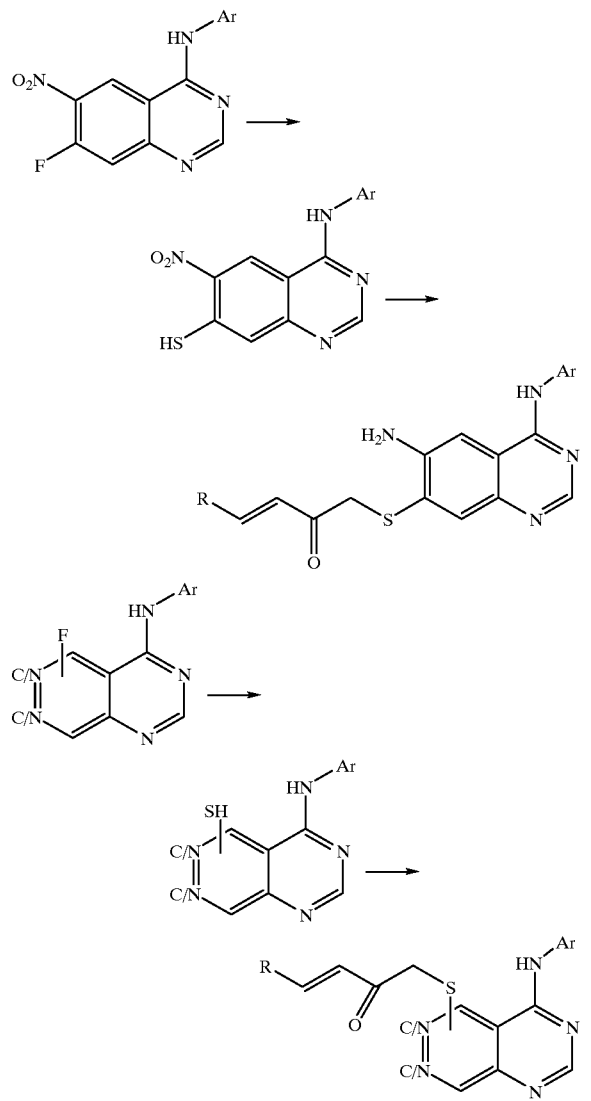

EXAMPLE 1

N-[4-(3-Bromo-phenylamino)-pyrido[4 3-d] pyrimidin-7-yl]-N-(3-morpholin-4-yl-propyl)-acrylamide

GENERAL METHOD A:

N-[4-(3-Bromo-phenylamino)-pyrido[4,3-d]pyrimidin7-yl]-N-(3-morpholin-4-yl-propyl)-acrylamide can be made by acylation of 7-amino-4-[(3-bromophenyl)amino]pyrido [4,3-d]pyrimidine [*J Med Chem,* 1995:3780] by methods familiar to one skilled in the art. For example, acylation with acrylic acid can be achieved through the use of a standard condensing agent such as 1-(3-dimethylaminopropyl)-3-ethylcarbodiimide HCl (EDAC) or through the use of acryloyl chloride and a tertiary base such as diisopropyl ethylamine as an acid scavenger.

N-alkylation of the acrylamides can then be achieved by methods familiar to one skilled in the art. For example, conversion of the amide to its monoanion by treatment with standard reagents such as sodium hydride followed by displacement on an appropriate halide such as N-(3-chloropropyl)morpholine or N-(4-chlorobutyl)morpholine affords the desired alkylated amide.

GENERAL METHOD B:

Alternatively, N-[4-(3-bromo-phenylamino)pyrido[4,3-d] pyrimidin-7-yl]-N-(3-morpholin-4-yl propyl)-acrylamide can be made by treating 7-fluoro-4-[(3-bromophenyl)amino] pyrido-[4,3-d]pyrimidine with N-(3-aminopropyl) morpholine in dimethylsulfoxide followed by acylation with acrylic acid and a coupling reagent such as 1-(3-dimethylaminopropyl)-3-ethylcarbodiimide HCl (EDAC) or acryloyl chloride and a tertiary base such as diisopropyl ethylamine according to methods familiar to those skilled in the art. See, for example, WO 9519774 Al.

EXAMPLE 2

N-[4-(3-Bromo-phenylamino)-pyrido[3,4-d] pyrimidin-6-yl]-N-(3-morpholin-4-yl-propyl)-acrylamide To a stirred solution of 4-[(3-bromophenyl)amino]6-[(3-morpholinopropyl)amino]pyrido[3,4-d]pyrimidine (400 mg, 0.90 mmol), (prepared from 4-[(3-bromophenyl) amino]-6-fluoropyrido[3,4-d]pyrimidine and 3-morpholinoprop-1-ylamine) DMAP (40 mg) and Et$_3$N (excess, 2.0 mL) at 0° C. under N$_2$ was added acryloyl chloride (1.2 mol eq., 1.08 mmol, 89 µL). After 1 hour stirring, a further two portions of acid chloride (89 µL each) were added over the next 2 hours, and the reaction was then stirred at 20° C. for 1 hour, diluted with water and extracted with EtOAc. The combined organic extracts were washed with brine, dried over anhydrous Na$_2$SO$_4$, and concentrated under reduced pressure before being chromatographed on silica gel eluting with MeOH/EtOAc (1:9) to MeOH/EtOAc (1:5) to give N-[4-[(3-bromophenyl)amino]pyrido[3,4-d]pyrimidin6-yl]-N-[3-morpholinopropyl]acrylamide] (142 mg, 32%) as a cream powder, mp (CH$_2$Cl$_2$/hexane) 178–180° C.

$^1$H NMR [(CD$_3$)$_2$SO]: δ 10.15 (s, 1H, NH), 9.15 (s, 1H, aromatic), 8.80 (s, 1H, aromatic), 8.47 (s, 1H, aromatic), 8.21 (br s, 1H, H-2'), 7.92 (br d, J =7.6 Hz, 1H, H-6'), 7.41 (t, J =8.0 Hz, 1H, H-5'), 7.37 (dt, J =8.1 Hz, J =1.6 Hz, J 1.6 Hz, 1H, H-4'), 6.25 (m, 2H, CH$_2$CHCO, CH$_2$CHCO), 5.66 (m, 1H, CH$_2$CHCO), 3.98 (t, J =7.5 Hz, 2H, CH$_2$NRCO), 3.46 (t, J =4.5 Hz, 4H, morpholino methylene), 2.29 (t, J =7.1 Hz, 2H, CH$_2$CH$_2$CH$_2$NRCO), 2.24 (br s, 4H, morpholino methylene), 1.73 (quintet, J =7.2 Hz, 2H, CH$_2$CH$_2$CH$_2$)

$^{13}$C NMR: δ 164.84, 156.69, 155.80, 151.83, 150.05, 143.01, 140.02, 130.51, 129.27, 127.88, 126.76, 124.32, 121.19, 120.82, 113.02, 66.02 (x2), 55.05, 53.02 (x2), 45.85, 24.63.

Analysis calculated for $C_{23}H_{25}BrN_6O_2 \cdot H_2O$ requires: C, 53.6; H, 5.3; N, 16.3%. Found: C, 53.8; H, 5.0; N, 16.3%.

EXAMPLE 3

N-[4-(3-Bromo-phenylamino)-auinazolin-7-yl] acrylamide

To an ice-cold solution of 0.158 g (0.5 mM) of 7-amino-4-(3-bromoanilino)-quinazoline [*J Med Chem*, 1995:3482] and 0.108 g of acrylic acid in 5.0 mL of dry dimethylformamide (DMF) was added 0.288 g of 1-(3-dimethylaminopropyl)-3-ethylcarbodiimide HCl (EDAC). After stirring for 5 minutes, the mixture became a solution, and the ice bath was removed. The reaction continued to stir at room temperature for 3 hours. The reaction was then poured into a mixture of ice and water and made basic with the addition of a saturated solution of sodium bicarbonate. This aqueous mixture was extracted three times with ethyl acetate, and the pooled extracts were dried over magnesium sulfate. The solution was filtered and concentrated in vacuo to afford a light yellow solid. The solid was dissolved in 100 mL of methanol, filtered, and concentrated in vacuo to approximately 10 mL. The solid which precipitated from solution was collected and dried in vacuo at 80° C. to give 50 mg of N-[4-(3-bromophenylamino)-quinazolin-7-yl] acrylamide, mp >265° C. Chemical ionization mass spectra: m/e 369.

$^1$H NMR (D$_6$-dimethyl sulfoxide): δ 5.86 (dd, 1H, J =10.1, J=1.9), 6.36 (dd, 1H, J =17.0, J =1.9), 6.51 (dd, 1H, J =16.9, J =10.1), 7.30 (m, 1H), 7.36 (t, 1H, J =8.1), 7.82 (dd, 1H, J =9.2, J =2.2), 7.9 (d, 1H, J =8.0), 8.25 (dd, 1H, J =3.6, J =1.9), 8.50 (d, 1H, J =8.9), 8.61 (s, 1H), 9.79 (s, 1H, —NH), 10.61 (s, 1H, —NH).

Analysis calculated for $C_{17}H_{13}BrN_4O$: C, 55.30; H, 3.55; N, 15.17. Found: C, 55.49; H, 3.63; N, 15.26.

EXAMPLE 4

N-[4-[(3-Bromophenyl)amino]quinazolin-7-yl]-N-[3-morpholinopropyl]acrylamide

To a solution of 4-[(3-bromophenyl)amino]-7-fluoroquinazoline (0.60 g, 1.89 mmol) in Dimethylsulfoxide (DMSO) (10 mL) was added 4-(3-aminopropyl)morpholine (7.54 mmol, 1.10 mL). The reaction mixture was heated at 110° C. for 26 hours and then diluted with water, basified by the addition of saturated NaHCO$_3$ and then extracted with EtOAc. The combined organic extracts were washed with brine, dried over anhydrous Na$_2$SO$_4$, and concentrated in vacuo. Column chromatography on Grade III alumina with gradient elution from EtOAc to EtOAc/MeOH (98:2) followed by recrystallization from EtOAc/hexane gave 4-[(3-bromophenyl)amino]-7-[(3-morpholinopropyl)amino] quinazoline (0.65 g, 78%) as cream crystals, mp 162–162.5° C.

$^1$H NMR [(CD$_3$)$_2$SO, 200 MHz]: δ 9.41 (s, 1H, NH), 8.43 (s, 1H, H-2), 8.24 (br s, IH, H-2'), 8.18 (d, J =9.2 Hz, 1H, H-5), 7.87 (br d, J =8.1 Hz, 1H, H-6'), 7.35–7.18 (m, 2H, H-4', 5'), 6.88 (dd, J =1.9 Hz, J =9.1 Hz, 1H, H-6'), 6.65 (t, J =5.3 Hz, 1H, CH$_2$NH), 6.62 (br s, 1H, H-8), 3.60 (t, J =4.6 Hz, 4H, morpholino methylene), 3.19 (dt, J =6.4 Hz, J =6.4 Hz, J =5.8 Hz, 1H, CH$_2$CH$_2$NH), 2.43–2.33 (m, 6H, morpholino methylene, CH$_2$CH$_2$CH$_2$NH), 1.75 (quintet, J =6.8 Hz, 1H, CH$_2$CH$_2$CH$_2$).

$^{13}$C NMR: δ 156.56, 154.27, 152.41, 152.32, 141.60, 130.15, 124.90, 123.41, 123.31, 121.06, 119.87, 116.51, 105.68, 102.21, 66.13 (x2), 55.81, 53.31 (x2), 40.46, 25.14.

To a solution of the above 4-[(3-bromophenyl)amino]-7-[(3-morpholinopropyl)amino]quinazoline (0.10 g, 0.230 mmol) in dry DMF (5.0 mL) under N$_2$ was added acrylic acid (0.565 mmol, 39 μL), Et$_3$N (100 μL), and 1-(3-dimethylaminopropyl)-3-ethylcarbodiimide hydrochloride (EDCI.HCl) (0.565 mmol, 108 mg), the reaction mixture was stirred at room temperature for 4 days with additional acrylic acid (40 μL), triethylamine Et$_3$N (100 μL), and EDCI.HCl (100 mg) being added each day. The DMF was then removed in vacuo and the resulting residue diluted with saturated NaHCO$_3$ and extracted with EtOAc. The combined organic extracts were washed with brine, dried over anhydrous Na$_2$SO$_4$, and concentrated at reduced pressure. Column chromatography on silica gel with gradient elution from MeOH/EtOAc/CH$_2$Cl$_2$ (1:4:5) to MeOH/EtOAc/CH$_2$Cl$_2$ (2:4:4) gave at higher R$_f$; N-[4-[(3bromophenyl)amino]quinazolin-7-yl]-N[3-morpholinopropyl]acrylamide (39 mg, 35%) as a white powder, mp (EtOAc/hexane) 86–88° C. (decomp).

$^1$H NMR [(CD$_3$)$_2$SO, 200 MHz]: δ 9.96 (s, 1H, NH), 8.68 (s, 1H, H-2), 8.63 (d, J =8.7 Hz, 1H, H-5), 8.23 (br s, 1H, H-2'), 7.91 (dt, J =7.3 Hz, J =2.0 Hz, J =2.0 Hz, 1H, H-6'), 7.68–7.58 (m, 2H, aromatic), 7.42–7.31 (m, 2H, aromatic), 6.18 (m, 2H, CH$_2$CHCO, CH$_2$CHCO), 5.63 (dd, J =2.0 Hz, J =10.0 Hz, 1H, CH$_2$CHCO), 3.90 (t, J =7.1 Hz, 2H, CH$_2$CH$_2$CH$_2$NCO), 3.51 (t, J =4.3 Hz, 4H, morpholino methylene), 2.50 (br s, 2H, CH$_2$CH$_2$CH$_2$NCO), 2.28 (br s, 4H, morpholino methylene), 1.67 (quintet, J =6.5 Hz, 2H, CH$_2$CH$_2$CH$_2$). At lower R$_f$; recovered starting material, 4-[(3-bromophenyl)amino]-7-[(3-morpholinopropyl)amino] quinazoline (34%) identical with an authentic sample.

EXAMPLE 5

3-[4-(3-Bromo-phenylamino)-quinazolin-7-ylcarbamoyl]acrylic acid

To a 5° C. solution of 0.158 g of 7-amino-4-(3-bromoanilino)-quinazoline (*J Med Chem*, 1995:3482) in 10 mL of tetrahydrofuran was added 0.059 g of maleic anhydride. The cold solution stirred for 15 minutes, and then the ice bath was removed. The reaction warmed to room temperature where it continued stirring for 15 hours. The suspension was heated under reflux for 30 minutes and then stirred at room temperature another 15 hours. Another 0.059 g of maleic anhydride and 20 mL of tetrahydrofuran were added, and the reaction was refluxed for an additional 2 hours. After another 15 hours at room temperature, the reaction was refluxed for 15 hours. The reaction was filtered, and the light tan solid was recrystallized first from dimethylformamide and then a second time from methanol to afford 0.036 g of the desired product.

$^1$H NMR [(CD$_3$)$_2$SO]: δ 12.95 (br s, 1H, exchanges with D$_2$O), 11.04 (br s, 1H, exchanges with D$_2$O), 9.81 (br s, 1H, exchanges with D$_2$O), 8.62 (s, 1H), 8.49 (d, J =9.2 Hz, 1H), 8.24 (s, 1H), 8.17 (d, J =1.7 Hz, 1H), 7.90 (d, J =8.4 Hz, 1H), 7.78 (d, J =9.2 Hz, 1H), 7.36 (t, J =8.1 Hz, 1H), 7.30 (dd, J =1 Hz, 9 Hz, 1H), 6.50 (d, J =12.1 Hz, 1H), 6.37 (d, J =11.8 Hz, 1H);

CIMS m/z (relative %): 411.3 (95), 412.3 (23), 413.3 (100), 414.3 (21).

Analysis calculated for $C_{18}H_{13}BrN_4O_3$: C, 52.32; H, 3.17; N, 13.56. Found: C, 52.57; H, 3.51; N, 13.16.

EXAMPLE 6

3-[4-(3-Bromo-phenylamino)-quinazolin-7-ylcarbamoyl]acrylic acid ethyl ester

To an ice cold solution of 0.158 g of 7-amino-4(3-bromoanilino)-quinazoline and 0.216 g of monoethyl fumarate in 3 mL of dry dimethylformamide was added 0.288 g of 1-(3-dimethylaminopropyl)-3-ethylcarbodiimide HCl (EDAC). 7-Amino-4-(3-bromoanilino)quinazoline can be made by methods well-known to those skilled in the art. See, for example, J Med Chem, 1995:3482, which is hereby incorporated by reference. After stirring at 5° C. for 5 minutes, the ice bath was removed, and the reaction was permitted to warm to room temperature where it stirred for 15 hours. The reaction was poured into cold water, and the suspension was made basic with the addition of a saturated sodium bicarbonate solution. The resulting solid was collected by filtration, washed with water, and then recrystallized from 50 mL of ethanol to afford 0.052 g of the desired product, mp >260° C.

$^1$H NMR [(CD$_3$)$_2$SO]: δ 10.99 (br s, 1H, exchanges with D$_2$O), 9.82 (br s, 1H, exchanges with D$_2$O), 8.62 (s, 1H), 8.52 (d, J =8.9 Hz, 1H), 8.24 (s, 2H), 7.90 (d, J =8.2 Hz, 1H), 7.81 (dd, J =1.7 Hz, 8.9 Hz, 1H), 7.34 (m, 2H), 7.26 (d, J =15.7 Hz, 1H), 6.79 (d, J =15.4 Hz, 1H), 3.33 (q, J =7.0 Hz, 14.2 Hz, 2H), 1.28 (t , J =7.0 Hz, 3H);

CIMS m/z (relative %): 440 (19%), 441 (100), 442 (37), 443 (78).

Elemental analysis calculated for C$_{20}$H$_{17}$BrN$_4$O$_3$: C, 54.44; H, 3.88; N, 12.70; Br, 18.11. Found: C, 54.32; H, 3.85; N, 12.76; Br, 17.89.

EXAMPLE 7

N-(3-Bromo-phenyl)-quinazolin-4-yl-amine

N-(3-Bromo-phenyl)-quinazolin-4-yl-amine was prepared according to methods well-known in the art. See, for example, J Med Chem, 1995;38(18):3482–3487.

EXAMPLE 8

4-(3-Bromo-phenylamino)-6,7-dimethoxyquinazoline 4-(3-Bromo-phenylamino)-6,7-dimethoxyquinazoline is synthesized according to methods well-known in the art. See, for example, European Patent Application Number 566 226 Al.

EXAMPLE 9

But-2-enoic acid [4-(3-bromo-phenylamino)-quinazolin-7yl]-amide

To an ice cold solution of 0.158 g of 7-amino-4(3-bromoanilino)-quinazoline (J Med Chem, 1985:3482) in 5 mL of tetrahydrofuran was added dropwise a solution of 0.105 g of crotonic acid chloride in 5 mL of tetrahydrofuran. When the addition was complete, the ice bath was removed and the reaction stirred at room temperature for 15 hours. The reaction was filtered to remove the yellow solid which was washed with tetrahydrofuran and recrystallized from 20 mL of boiling methanol to afford 0.060 g of the desired product, mp >250° C.

$^1$H NMR (CD$_3$)$_2$SO]: δ 11.44 (br s, 1H, exchanges with D$_2$O), 11.04 (s, 1H, exchanges with D$_2$O), 8.92 (s, 1H), 8.78 (d, J =9.2 Hz, 1H), 8.52 (d, J =1.9 Hz, 1H), 8.05 (t, J =1.8 Hz, 1H), 7.91 (dd, J =2.1 Hz, 9.3 Hz, 1H), 7.76 (m, 1H), 7.52 (m, 1H), 7.45 (t, J =8.0 Hz, 1H), 6.70 (m, 1H), 6.28 (dd, J =1.7 Hz, 15.1 Hz, 1H), 1.92 (dd, J =1.6 Hz, 6.9 Hz, 3H);

CIMS: 382 (21), 383 (100), 384 (34), 385 (64).

Analysis calculated for C$_{18}$H$_{15}$BrN$_4$O.1 HCl.0.5 H$_2$O: C, 50.43; H, 4.00; N, 13.07; Br, 18.64; Cl, 8.27. Found: C, 50.71; H, 4.00; N, 12.98; Br, 18.93; Cl, 7.51.

EXAMPLE 10

N-[4-(3-Bromo-phenylamino)-6-(3-morpholin-4-yl-propylamino)-quinazolin-7-yl]-acrylamide Treatment of 6-chloro-7-nitroquinazolin-4-one (Aust J Chem, 1995;48:227–232) with thionyl chloride or POCl$_3$ affords the 4,6-dichloro-7-nitroquinazoline. Reaction with 3-bromoaniline affords a mixture of 4-(3-bromophenylamino)-6-chloro-7-nitroquinazoline and 4-chloro-6-(3-bromophenylamino)-7-nitroquinazoline which are separated by column chromatography. Treatment of the desired 4-(3-bromophenylamino)-6-chloro-7-nitroquinazoline with N-(3-aminopropyl)morpholine and subsequent reduction of the nitro functionality with, for example, iron in acetic acid affords 7-amino-4-(3-bromo-phenylamino)-6-(3-morpholin4-yl-propylamino)-quinazoline. Acylation to afford the acrylamide is accomplished according to method of Example 3.

EXAMPLE 11

N-[4-[(3-Bromophenyl)amino]quinazolin-6-yl] acrylamide

To a solution of 6-amino-4-[(3-bromophenyl)amino] quinazoline (2.0 g, 6.35 mmol) in dry DMF (20 mL) under N$_2$ was added acrylic acid (12.7 mmol, 0.87 mL). The resulting solution was cooled to 0° C. and 1-(3-dimethylaminopropyl)-3-ethylcarbodiimide hydrochloride (EDCI.HCl) (7.62 mmol, 1.46 g) was added. The reaction was stirred at 0° C. for 15 minutes and then allowed to warm to room temperature and stirred for a further 2 hours, after which additional acrylic acid (0.30 mL) and EDCI.HCl (0.30 g) were added. After a further 2 hours, the reaction was complete by tlc, solvent was removed under reduced pressure, and the resulting residue diluted with saturated NaHCO$_3$ and repeatedly extracted with EtOAc. The combined organic extracts were washed with brine, dried over anhydrous Na$_2$SO$_4$, and concentrated under reduced pressure. Column chromatography on grade III alumina eluting with EtOAc/MeOH (95:5) followed by recrystallization from EtOAc/hexane gave a spongy white solid, which upon several hours under high vacuum gave N-[4-[(3-bromophenyl)amino]quinazolin-6-yl]acrylamide (1.06 g, 45%) as a cream powder, mp 258–261° C.

$^1$H NMR [(CD$_3$)$_2$SO, 200 MHz]: δ 10.51 (s, 1H, CONH), 9.93 (s, 1H, NH), 8.83 (br s, 1H, H-5), 8.59 (s, 1H, H-2), 8.18 (br s, 1H, H-2'), 7.94–7.78 (m, 3H, H-6', 8, 5'), 7.40–7.27 (m, 2H, H-7, 4'), 6.54 (dd, J =9.8 Hz, J =17.0 Hz, 1H, CH$_2$CHCO), 6.36 (dd, J =2.1 Hz, J =16.9 Hz, 1H, CH$_2$CHCO), 5.85 (dd, J =2.0 Hz, J =9.7 Hz, 1H, CE$_2$CHCO).

Mass spectrum (CI): 371 (95, $^{81}$BrMH$^+$), 370 (53, $^{81}$BrM$^+$), 369 (100, $^{79}$BrMH$^+$), 368 (33, $^{79}$BrM$^+$).

Analysis calculated for C$_{17}$H$_{13}$BrN$_4$O requires: C, 55.30; H, 3.55; N, 15.17%. Found: C, 55.19; H, 3.34; N, 14.88%.

EXAMPLE 12

N-[4-(N,N-Dimethylamino)-quinazolin-6-yl] acrylamide

A suspension of 6-nitroquinazolone (3.50 g, 18.5 mmol) in neat SOCl$_2$ (30 mL) containing two drops of DMF was refluxed for 3 hours until it became clear. The excess SOCl$_2$ was removed under reduced pressure, and dry benzene was added and then evaporated under reduced pressure to remove all traces of SOCl$_2$. The resulting crude 4-chloro- 6-nitroquinazoline was dissolved in dry $CH_2Cl_2$ (50 mL) and washed with saturated $Na_2CO_3$ (x2), and this solution was then added to a solution of 4-amino-2-bromo-N,N-dimethylbenzylamine (20.3 mmol, 4.64 g) in i-PrOH (60 mL) containing $Et_3N$ (excess, 7.0 mL). The resulting reaction mixture was heated at reflux for 3 hours and then concentrated under reduced pressure, diluted with water, and extracted with EtOAc. The combined organic extracts were dried over anhydrous $Na_2SO_4$, concentrated under reduced pressure, and chromatographed on silica gel eluting with $CH_2Cl_2$/EtOAc (1:1) to MeOH/$CH_2Cl_2$/EtOAc (2:9:9) to give 4-N,N-dimethylamino-6-nitroquinazoline (2.56 g, 64%), as yellow crystals, mp ($CH_2Cl_2$) 131–133° C.

$^1$H NMR [$(CD_3)_2SO$], (400 MHz): δ 9.02 (d, J =2.4 Hz, 1H, H-5), 8.59 (s, 1H, H-2), 8.47 (dd, J =2.5 Hz, J =9.2 Hz, 1H, H-7), 7.85 (d, J =9.2 Hz, 1H, H-8), 3.46 (s, 6H, $N(CH_3)_2$).

Further elution gave 2-bromo-N,N-dimethyl-4-(6-nitroquinazolin-4-yl)benzylamine (0.62 g, 8%), as a yellow powder, mp ($CH_2Cl_2$) 198–200° C.

$^1$H NMR [$(CD_3)_2SO$], (400 MHz): δ 10.47 (br s, 1H, NH), 9.66 (d, J =2.4 Hz, 1H, H-5), 8.77 (s, 1H, H-2), 8.57 (dd, J =9.2 Hz, J =2.5 Hz, 1H, H-7), 8.21 (d, J =2.0 Hz, 1H, H-2$^1$), 7.95 (d, J =9.1 Hz, 1H, H-8), 7.91 (dd, J =8.4 Hz, 1H, H-6'), 7.49 (d, J =8.5 Hz, 1H, H-5'), 3.46 (s, 2H, $CH_2N(CH_3)_2$), 2.22 (s, 6H, $N(CH_3)_2$).

Analysis calculated for $C_{17}H_{16}BrN_5O_2 \cdot 1.5H_2O$ requires: C, 47.6; H, 4.5; N, 16.3%. Found: C, 47.7; H, 4.2; N, 15.7%.

To a refluxing solution of the above 4-N,N-dimethylamino-6-nitroquinazoline amine (1.20 g, 5.50 mmol) in EtOH/$H_2O$ (2:1, 90 mL) containing glacial acetic acid (4.0 mL) was added freshly washed (1N HCl then distilled $H_2O$) iron powder (4 mol eq., 1.24 g) in portions. Identical reaction procedure and workup as above gave, after chromatography on silica gel eluting with $CH_2Cl_2$/EtOAc (1:1) to MeOH/$CH_2Cl_2$/EtOAc (1:4:5), 4-N,N-dimethylamino-6-aminoquinazoline (0.87 g, 84%), as a pale brown powder, mp (dihydrochloride salt from MeOH/$Et_2O$) 258–261° C.

$^1$H NMR (dihydrochloride salt), [$(CD_3)_2SO$], (400 MHz): δ 14.8 (br s, 1H, NH$^+$), 8.65 (s, 1H, H-2), 7.79 (m, 2H, H-5, H-8), 7.57 (dd, J =2.1 Hz, J =8.9 Hz, 1H, H-7), 5.70 (br s, 3H, $NH_3^+$), 3.55 (s, 6H, $N(CH_3)_2$).

To a stirred solution containing the above 4-N,N-dimethylamino-6-aminoquinazoline (0.65 g, 3.45 mmol), acrylic acid (4 mol eq., 13.8 mmol, 0.95 mL), and pyridine (excess, 1.3 mL) in DMA (20 mL) under $N_2$ was added 1-(3-dimethylaminopropyl)-3-ethylcarbodiimide hydrochloride (EDCI.HCl) (2 mol eq., 6.90 mmol, 1.32 g). The standard procedure above was followed to give after chromatography on silica gel eluting with EtOAc/$CH_2Cl_2$ (1:1) to MeOH/$CH_2Cl_2$/EtOAc (1:4:5), [4-(N,N-dimethylamino) quinazolin-6-yl]acrylamide (350 mg, 42%) as a cream powder, mp ($CH_2Cl_2$/hexane) 204–206° C.

$^1$H NMR [$(OD_3)_2SO$], (400 MHz): δ 10.49 (s, 1H, CONH), 8.80 (d, J =2.2 Hz, 1H, H-5), 8.46 (s, 1H, H-2), 7.88 (dd, J =2.4 Hz, J =9.1 Hz, 1H, H-7), 7.73 (d, J =9.0 Hz, 1H, H-8), 6.47 (dd, J =17.0 Hz, J =10.1 Hz, 1H, $CH_2CHCO$), 6.34 (dd, J =17.0 Hz, J =2.0 Hz, 1H, $CH_2CHCO$), 5.83 (dd, J =10.1 Hz, J =2.0 Hz, 1H, $CH_2CHCO$), 3.32 (s, 6H, $N(CH_3)_2$).

EXAMPLE 13

N-[4-(3-Methyl-phenylamino)-quinazolin-7-yl] acrylamide

To a stirred solution of 7-amino-4-[(3-methylphenyl) amino]quinazoline (123 mg, 0.49 mmol), acrylic acid (0.04 mL, 0.58 mmol), triethylamine (0.15 mL, 1.1 mmol) in DMF (1.5 mL) at 0° C. was added 1-(3-dimethylaminopropyl)-3-ethylcarbodiimide hydrochloride (123 mg, 0.64 mmol). The resulting light yellow mixture was stirred at 25° C. for 20 hours and quenched with water. The solid was collected and purified by sonication with a mixture of $CH_2Cl_2$/EtOAc/MeOH to give the desired product as a yellow solid (75 mg, 49%), mp 269.7–270° C.

$^1$H NMR [$(CD_3)_2SO$]: δ 10.63 (s, 1H, NH), 9.68 (s, 1H, NH), 8.58 (s, 1H, H2), 8.54 (d, J =9.3 Hz, 1H, H6), 8.25 (d, J=2.2 Hz, 1H, H8), 7.83 (dd, J =9.0, 1.9 Hz, 1H, H5), 7.71 (m, 2H, H2', H6'), 7.32 (t, J =8.3 Hz, 1H, H5'), 6.99 (d, J =7.1 Hz, 1H, H4'), 6.56 (dd. J =16.8, 10.0 Hz, 1H, CH=$CH_2$), 6.40 (dd. J =17.1, 5.0 Hz, 1H, CH=$CH_2$), 5.9 (dd, J =10.3, 2.0 Hz, 1H, CH=$CH_2$), 2.39 (s, 3H, $CH_3$).

Mass Spectrum (CI): 305 (100, MH$^+$), 304 (31.84, M$^+$).

Calculated for $C_{18}H_{16}N_4O \cdot 0.4H_2O$: C, 69.39; H, 5.44; N, 17.94%. Found: C, 69.19; H, 5.19; N, 17.67%.

EXAMPLE 14

N-[4-(3-Chloro-phenylamino)-quinazolin-7-yl] acrylamide 1-(3-dimethylaminopropyl)-3-ethylcarbodiimide hydrochloride (288 mg, 1.5 mmol) was added to a solution of 6-amino-4[(3-chlorophenyl)amino]guinazoline (136 mg, 0.5 mmol) and acrylic acid (108 mg, 1.5 mmol) in dimethylformamide (DMF) (5 mL), stirred under nitrogen at 0° C. After 15 minutes the reaction mixture was stirred at 25° C. for 18 hours, and then poured onto ice-water (50 mL) and after 1 hour the precipitate was collected by Buchner filtration. The residue was rinsed, air dried, dissolved in the minimum of 25° C. methanol (MeOH) (60 mL), concentrated at 25° C. under reduced pressure to below 10 mL, and recrystallized at 0° C. to give N-[4-[(3-chlorophenyl)amino] quinazolin-7-yl]acrylamide (33 mg, 20%) as a light orange solid, mp 296.5–298.5° C.

Calculated for $C_{17}H_{13}ClN_4O \cdot 0.08$ $CH_3OH \cdot 0.25$ $H_2O$: C, 61.82; H, 4.20; N, 116.89%. Found: C, 61.92, H, 4.23; N, 116.72%.

$^1$H NMR [$(CD_3)_2SO$]: δ 10.61 (brs, 1H, NH), 9.80 (s, 1H, NH), 8.62 (s, 1H, H2), 8.50 (d, J =9.0 Hz, H5), 8.25 (d, J =2.0 Hz, 1H, H8), 8.13 (t, J =2.0 Hz, 1H, H2'), 7.87–7.78 (m, 2H, H6 & H6'), 7.42 (t, J =8.2 Hz, 1H, H5'), 7.16 (dd, J =2.2, 7.9 Hz, 1H, H4'), 6.51 (dd, J =10.0, 17.1 Hz, 1H, CH=$CH_2$), 6.35 (dd, J =1.8, 17.1 Hz, 1H, CH=$CH_2$), 5.86 (dd, J =1.8, 10.1 Hz, 1H, CH=$CH_2$).

Mass Spectrum (CI) 327 (32, $^{37}$ClMH$^+$), 326 (25, $^{37}$ClM$^+$, $^{13}$C $^{35}$ClMH$^+$), 325 (100, $^{35}$ClMH$^+$), 322 (22, $^{35}$ClMH$^+$).

EXAMPLE 15

N-[4-(3-Bromo-phenylamino)-quinazolin-7-yl] methacrylamide

To a stirred solution of 7-amino-4-[(3-bromophenyl) amino]quinazoline (J Med Chem, 1995;38:3482) (150 mg, 0.48 mmol) in dry DMF (20 mL) was added methacrylic acid (200 mg) and 1-(3-dimethylaminopropyl)-3-ethylcarbodiimide hydrochloride (EDCI.HCl) (2.5 mol, 228 mg), the reaction mixture was stirred overnight then further amounts of EDCI.HCl (230 mg) and methacrylic acid (200 mg) were added. After a further 2 days stirring the solvent was removed under vacuum and the residue diluted with saturated $NaHCO_3$, extracted with ethyl acetate (EtOAc) and then the combined organic extracts were dried over anhydrous Na$_2$SO$_4$, concentrated under reduced pressure and chromatographed on silica gel eluting with MeOH/CH$_2$Cl$_2$/EtOAc (5:45:50) to MeOH/CH$_2$Cl$_2$/EtOAc (10:40:50) to give N-[4-[(3-bromophenyl)amino]quinazolin-7-yl]-2-methyl-acrylamide (43 mg, 24%) as a pale brown solid, np (CH$_2$Cl$_2$/hexane) 255–259° C.

$^1$H NMR [(CD$_3$)$_2$SO], (400 MHz) δ 10.22 (s, 1H, CONH), 9.76 (s, 1H, NH), 8.61 (s, 1H, H-2), 8.48 (d, J =9.2 Hz, 1H, H-5), 8.26 (m, 2H, H-2', 8), 7.92 (m, 2H, H-6', 6), 7.36 (t, J =8.0 Hz, 1H, H-5'), 7.30 (br d, J =8.3 Hz, 1H, H-4'), 5.92 (s, 1H, CH$_2$C(CH$_3$)CO), 5.63 (s, 1H, CH$_2$C(CH$_3$)CO), 2.00 (s, 3H, CH$_2$C(CH$_3$)CO).

Analysis calculated for C$_{18}$H$_{15}$BrN$_4$O requires: C, 56.4; H, 4.0; N, 14.6%. Found: C, 56.1; H, 4.0; N, 14.1%.

EXAMPLE 16

N-[4-(3-Bromo-phenylamino)-quinazolin-7-yl]ethenylsulfonamide

A solution of 7-amino-4-[(3-bromophenyl)amino]quinazoline (J Med Chem, 1995;38:3482) (500 mg, 1.59 mmol), triethylamine (Et$_3$N) (0.60 mL) and dimethylamine pyridine (DMAP) (catalytic) in tetrahydrofuran (THF) (30 mL) was reacted with chloroethanesulfonyl chloride (1.6 mol eq., 2.54 mmol, 265 μL) at 25° C. for 1 hour, stirred under N$_2$. The reaction mixture was diluted with saturated NaHCO$_3$ and extracted with EtOAc. The combined organic extracts were washed with brine, dried over anhydrous Na$_2$SO$_4$, concentrated under reduced pressure, and chromatographed on silica gel eluting with MeOH/CH$_2$Cl$_2$/EtOAc (3:47:50). Crystallization from CH$_2$Cl$_2$/hexane, gave N-[4-[(3-bromophenyl)amino]quinazolin-7-yl]vinylsulfonamide (80 mg, 12%) as a cream powder, mp 218° C. decomposes (dec).

$^1$H NMR [(CD$_3$)$_2$SO], (400 MHz) δ 10.73 (s, 1H, SO$_2$NH), 9.80 (s, 1H, NH), 8.59 (s, 1H, H-2), 8.47 (d, J =9.1 Hz, 1H, H-5), 8.21 (br s, 1H, H-2'), 7.87 (br d, J=8.0 Hz, 1H, H-6'), 7.47 (d, J =2.1 Hz, 1H, H-8), 7.40 (dd, J =9.0 Hz, J =2.2 Hz, 1H, H-6), 7.36 (t, J =8.0 Hz, 1H, H-5'), 7.30 (br d, J =8.0 Hz, 1H, H-4'), 6.93 (dd, J =16.4 Hz, J =9.9 Hz, 1H, CH$_2$CHSO$_2$) 6.28 (d, J =16.4 Hz, 1H, CH$_2$CHSO$_2$), 6.15 (d, J =9.9 Hz, 1H, CH$_2$CHSO$_2$).

Analysis calculated for C$_{16}$H$_{13}$BrN$_4$O$_2$S requires: C, 47.4; H, 3.2%. Found: C, 47.3; H, 3.5%.

EXAMPLE 17

N-[4-(3-Bromo-Phenylamino)-quinazolin-7-yl]propanamide

To a solution of 7-amino-4-[(3-bromophenyl)amino]quinazoline (163 mg, 0.52 mmol) in dry THF (3 mL) stirred under N$_2$ at 25° C. was added dropwise propionyl chloride (0.05 mL, 0.58 (mmol). A yellow solid formed at once. After 1 hour the solid was collected by Buchner filtration and washed with ether then dried. Recrystallized from wet methanol afforded the desired product as bright yellow solid (81 mg, 38%), mp 282–283° C.

$^1$H NMR [(CD$_3$)$_2$SO]: δ 11.4 (brs, 1H, NH), 10.76(s, 1H, NH), 8.90 (s, 1H, H8), 8.64 (d, J =9.0 Hz, 1H, H6), 8.42 (s, 1H, H2), 8.06 (s, 1H, H2'), 7.80(dd, J =9.2, 1.9 Hz, 1H, H5), 7.74 (d, J =7.8 Hz, 1H, H4'), 7.50 (d, J =8.0 Hz, 1H, H6'), 7.45 (t, J =8.0 Hz, 1H, H5'), 2.48 (q, J =7.6 Hz, 2H, CH$_2$), 1.13 (t, J =7.5 Hz, 3H, CH$_3$).

Mass Spectrum (APCI): 373 (100, $^{81}$BrMH$^+$), 372 (21, $^{81}$BrM$^+$), 371 (96, $^{79}$BrMH$^+$).

Calculated for C$_{17}$H$_{15}$N$_4$BrO·HCl 0.2H$_2$O: C, 49.64; H, 4.02; N, 13.63% Found: C, 49.48; H, 3.91; N, 13.57%.

EXAMPLE 18

N-[4-[(3-Chlorophenyl)amino]quinazolin-6-yl]acrylamide 1-3-dimethylaminopropyl)-3-ethylcarbodiimide hydrochloride (1902 mg, 1 mmol) was added to a solution of 6-amino-4[(3-chlorophenyl)amino]quinazoline (136 mg, 0.5 mmol) acrylic acid (74 mg, 1.0 mmol) and pyridine (201 mg, 2.5 mmol) in THF/DMF (4:1, 2.5 mL), stirred under nitrogen at 0° C. After 20 minutes the reaction mixture was stirred at 25° C. for 3 hours, and then poured onto water (12.5 mL), and extracted with EtOAc (2×10 mL). The combined extracts were treated with dilute hydrochloric acid (0.5 M, 10 mL), and the precipitate was collected by Buchner filtration, rinsed with water (10 mL), ether (2×10 mL), and air dried to give N-[4-[(3-chlorophenyl)amino]quinazolin-6-yl] acrylamide hydrochloride (93 mg, 48%) as a dull yellow solid, mp 223–227° C.

Calculated for C$_{18}$H$_{13}$ClN$_4$O·HCl.1.5 H$_2$O: C,52.59; H, 4.41;N, 14.43%. Found: C, 52.43, H, 4.37; N, 14.27%.

$^1$H NMR[(CD$_3$)$_2$SO]: δ 11.46 (brs, 1H, NH), 11.05 (s, 1H, NH), 9.13 (d, J =2.0 Hz, 1H, H5), 8.90 (s, 1H, H2), 8.12 (dd, J =2.0, 9.0 Hz, 1H, H7), 7.99 (d, J =9.0 Hz, 1H, H8), 7.88 (t, J =2.0 Hz, 1H, H2'), 7.68 (dd, J =6.1, 1.0 Hz, 1H, H6'), 7.51 (t, J =8.0 Hz, 1H, H5'), 7.37 (dd, J =8.1, 1.2 Hz, 1H, H-4'), 6.63 (dd, J =10.3, 17.1 Hz, 1H, CH=CH$_2$), 6.37 (dd, J =1.6, 17.1 Hz, 1H, CH=CH$_2$), 5.87 (dd, J =1.7, 10. Hz, 1H, CH=CH$_2$).

Mass Spectrum, Chemical Ionization (CI): 327 (8, $^{37}$ClMH$^+$), 325 (37, $^{35}$ClMH$^+$), 135 (100).

EXAMPLE 19

N-[4-[(3-Methylphenyl)amino]quinazolin-6-yl]acrylamide

Isobutyl chloroformate (20.35 g, 0.15 mol) was added dropwise over 20 minutes to a solution of acrylic acid (10.82 g), 0.15 mol) and triethylamine (30.19 g, 0.30 mol) in THF (400 mL), stirred under nitrogen at 0° C. The slurry was stirred at that temperature for 30 minutes, and then 6-amino-4[(3-methylphenyl)amino]quinazoline (27.71 g, 107 mmol) in DMF (80 mL) was added dropwise over 45 minutes. After a further 4 hours, further mixed anhydride (from acrylic acid (3.61 g, 50 mmol), isobutyl chloroformate (6.80 g, 50 mmol) and triethylamine (10.1 g, 100 mmol) in THF (100 mL) at 0° C.) was added in one portion. After a further 15 minutes, the reaction mixture was stirred at 25° C. for 30 minutes, and then poured onto ice-water (1 L). Ether (200 mL) was added and the phases were separated. The aqueous phase was extracted with EtOAc (500 mL), and the combined organic phases were washed with water (500 mL), and saturated brine (250 mL). The solution was stirred with anhydrous MgSO$_4$ for 2 minutes, filtered, and silica gel (150 g) was added. The mixture was stripped to dryness, and used as the origin of a flash silica chromatography column (700 g), eluting with acetone/dichloromethane (25% 4 L, 35% 8 L, 40% 4 L). The solvent was stripped from the appropriate fractions and the residue was suspended in EtOAc (200 mL) refluxed for 5 minutes and sonicated at 60° C. for 20 minutes, then collected by Buchner filtration, rinsed with EtOAc (3×25 mL), and dried in a vacuum oven at 75° C. for 16 hours, to give N-[4-[(3-methyl-phenyl)amino]quinazolin-6-yl]acrylamide (11.38 g, 35%) as a light yellow solid, mp 247–8° C.

Calculated for $C_{18}H_{16}N_4O.0.1\ H_2O$: C, 70.61; H, 5.33; N, 18.30%. Found: C, 70.33; H, 5.19; N, 18.17%.

$^1$H NMR [$(CD_3)_2SO$]: δ 10.49 (brs, 1H, NH), 9.76 (brs, 1H, NH), 8.75 (d, J =2.5 Hz, 1H, H5), 8.52 (s, 1H, H2), 7.89 (dd, J =2.0, 9.2 Hz, 1H, H7), 7.77 (d, J =8.9 Hz, 1H, H8), 7.64–7.60 (m, 2H, H6' & H2'), 7.26 (dt, $J_d$=1.4 Hz, $J_t$=7.5 Hz, 1H, H5'), 6.94 (d, J =7.2 Hz, 1H, H4'), 6.53 (dd, J =10.1, 16.9 Hz, 1H, CH=CH$_2$), 6.34 (dd, J =1.9, 16.9 Hz, 1H, CH=CH$_2$), 5.84 (dd, J =1.9, 10.1 Hz, 1H, CH=CH$_2$) 2.34 (s, 3H, Me).

Mass Spectrum (CI) 305 (100, MH$^+$), 304 (49, M$^+$).

EXAMPLE 20

N-[4-[(3-(Trifluoromethyl) phenyl)amino] quinazolin-6-yl]acrylamide 1-(3-dimethylaminopropyl)-3-ethylcarbodiimide hydrochloride (212 mg, 1.1 mmol) was added to a solution of 6-amino-4[(3-(trifluoromethyl)phenyl)amino]quinazoline (153 mg, 0.5 mmol) acrylic acid (73 mg, 1.0 mmol) and pyridine (206 mg, 2.5 nmmol) in THF/DMF (4:1, 2.5 mL), stirred under nitrogen at 0° C. After 15 minutes the reaction mixture was stirred at 25° C. for 1 hour, and then recooled to 0° C. Dilute hydrochloric acid (0.5 M, 10 mL) was added, and after 15 minutes the precipitate was collected by Buchner filtration. The residue was rinsed with water (5 mL) and ether (2×5 mL) and dried in a vacuum oven at 75° C. overnight to give N-[4-[(3-(trifluoromethyl) phenyl)amino] quinazolin-6-yl]acrylamide hydrochloride (87 mg, 45%) as a light greenish solid, mp 195–199° C.

Calculated for $C_{18}H_{13}F_3N_4O.HCl.0.5\ H_2O$: C, 53.54; H, 3.74;N, 13.88%. Found: C, 53.70; H, 3.72; N, 13.73%.

$^1$H NMR [$(CD_3)_2SO$]: δ 11.59 (brs, 1H, NH), 10.99 (s, 1H, NH), 9.17 (d, J =2.0 Hz, H5), 8.92 (s, 1H, H2), 8.12 (s, 1H, H2'), 8.10 (dd, J =2.0, 9.2 Hz, 1H, H7), 8.04 (d, J =8.0 Hz, 1H, H6'), 7.98 (d, J =9.0 Hz, 1H, H8), 7.74 (t, J =7.9 Hz, 1H, H5'), 7.68 (d, J =7.8 Hz, 1H, H4'), 6.60 (dd, J =10.1, 16.9 Hz, 1H, CH=CH$_2$), 6.38 (dd, J =1.6, 16.9 Hz, 1H, CH=CH$_2$), 5.89 (dd, J =1.6, 10.1 Hz, 1H, CH=CH$_2$).

Mass Spectrum (CI) 359 (45, MH$^+$), 134 (100).

EXAMPLE 21

N-[4-[(3-Bromophenyl)amino]-7-[3-(4-morpholino) propoxy]quinazolin-6-yl]acrylamide Sodium metal (27.6 mmol, 0.63 g) was added to a solution of 3-morpholinopropan-1-ol (22.0 mmol, 3.20 g) in THF (60 mL) under N$_2$. The resulting suspension was stirred at 20° C. for 2 hours and then cannulated into a solution of 4-[(3-bromophenyl)amino]-7-fluoro-6-nitroquinazoline, J Med Chem, 1996(39):918) (2.0 g, 5.51 mmol) in THF (50 mL) under N$_2$. The solution was then heated at reflux for 24 hours before being diluted with water and extracted with EtOAc. The combined organic extracts were dried over anhydrous Na$_2$SO$_4$, concentrated under reduced pressure and chromatographed on alumina eluting with EtOAc/hexane (1:1) to MeOH/CH$_2$Cl$_2$/EtOAc (2:3:5) to give 4-[(3-bromophenyl)amino]7-[(3-morpholino)propyloxy]-6-nitroquinazoline (1.75 g, 65%) as a yellow powder, mp (MeOH) 216–220° C.

$^1$H NMR [$(CD_3)_2SO$]: δ 10.12 (s, 1H, NH), 9.24 (s, 1H, aromatic), 8.69 (s, 1H, aromatic), 8.19 (t, J =1.8 Hz, 1H, H-2'), 7.88 (dt, $J_d$=7.8 Hz, 3t =1.4 Hz, 1H, H-6'), 7.49 (s, 1H, aromatic), 7.38 (t, J =8.0 Hz, 1H, H-5'), 7.34 (d,$_t$=8.1 Hz, $J_t$=1.4 Hz, 1H, H-4'), 4.35 (t, J =6.2 Hz, 2H, CH$_2$CH$_2$CB$_2$O), 3.58 (t, J =4.6 Hz, 4H, morpholino methylene), 2.45 (t, J =7.0 Hz, 2H, NCH$_2$CH$_2$CH$_2$), 2.37 (br s, 4H, morpholino methylene), 1.94 (quintet, J =6.6 Hz, 2H, CH$_2$CH$_2$CH$_2$). $^{13}$C NMR: δ 157.76, 157.26, 153.76, 153.21, 140.32, 138.86, 130.37, 126.38, 124.26, 121.70, 121.13, 120.72, 110.11, 107.88, 67.87, 66.13 (x2), 54.42, 53.28 (x2), 25.30.

Analysis calculated for $C_{21}H_{22}BrN_5O_4.0.75\ H_2O$ requires: C, 50.3; H, 4.7; N, 14.0%. Found: C, 50.3; H, 4.4; N, 13.8%.

Freshly washed (1N HCl then distilled H$_2$O) iron powder (12 mmol, 0.686 g) was added in portions to a refluxing solution of the above nitroquinazoline (1.50 g, 3.07 mmol) in EtOH/H$_2$O (2:1, 80 mL) containing glacial acetic acid (2.0 mL). The resulting suspension was heated at reflux with vigorous stirring for 20 minutes then cooled, basified by the addition of concentrated NH$_3$ and filtered through a pad of celite. The celite pad was washed with EtOH before the filtrate was concentrated under reduced pressure, diluted with water, and extracted with EtOAc. The combined organic extracts were dried over anhydrous Na$_2$SO$_4$, concentrated under reduced pressure, and chromatographed on Grade III alumina eluting with CH$_2$Cl$_2$/EtOAc (1:1) to MeOH/EtOAc (2:98) to give 6-amino-4-[(3-bromophenyl) amino]-7[(3-morpholino)propyloxy]quinazoline (1.08 g, 77%) as a pale brown powder, mp (EtOAc/hexane) 158–160° C.

$^1$H NMR [$(CD_3)_2SO$], (400 MHz): δ 9.37 (s, 1H, NH), 8.40 (s, 1H, aromatic), 8.24 (t, J =1.9 Hz, 1H, H-2$^1$), 7.86 (ddd, J =8.2, 0.8, 1.8 Hz, 1H, H-6'), 7.42 (s, 1H, aromatic), 7.30 (t, J =8.1 Hz, 1H, H-5'), 7.21 (ddd, J =8.2, 1.0, 1.9 Hz, 1H, H-4'), 7.09 (s, 1H, aromatic), 5.36 (s, 2H, NH$_2$), 4.20 (t, J =6.2 Hz, 2H, CH$_2$CH$_2$CH$_2$O), 3.59 (t, J =4.6 Hz, 4H, morpholino methylene), 2.50 (t, J =7.3 Hz, 2H, NCH$_2$CH$_2$CH$_2$), 2.39 (br s, 4H, morpholino methylene), 1.99 (quintet, J =6.7 Hz, 2H, CH$_2$CH$_2$CH$_2$).

$^{13}$C NMR: δ 154.88, 151.94, 150.19, 144.84, 141.94, 138.50, 130.16, 124.66, 123.02, 121.09, 119.65, 110.42, 106.37, 100.81, 66.45, 66.14 (x2), 54.77, 53.29 (x2), 25.50.

Analysis calculated for $C_{21}H_{24}BrN_5O_2.0.25\ H_2O$ requires: C, 54.5; H, 5.3; N, 15.1%. Found: C, 54.6; H, 5.5; N, 15.0%.

To a stirred solution of the above 6-aminoquinazoline (0.50 g, 1.09 mmol), acrylic acid (6 mol, 6.54 mmol, 449 μL), and Et$_3$N (excess, 2.0 mL)in DMF (20 mL) under N$_2$ was added 1-(3-dimethyl-aminopropyl)3-ethylcarbodiimide hydrochloride (EDCI.HCl) (3 mol, 3.27 mmol, 627 mg). The reaction was stirred at 0° C. for 15 minutes and then allowed to warm to room temperature and stirred for a further 2 hours. The solvent was removed under reduced pressure, and the resulting residue was diluted with saturated NaHCO$_3$ and repeatedly extracted with EtOAc. The combined organic extracts were washed with brine, dried over anhydrous Na$_2$SO$_4$, and concentrated under reduced pressure. Chromatography on Grade III alumina eluting with EtOAc/hexane (9:1) to MeOH/EtOAc (2:98), N-[4-[(3-bromophenyl)amino]-7-[(3-morpholino)propyloxy] quinazolin-6-yl]acrylamide (329 mg, 59%) as a cream powder, mp (EtOAc/Et$_2$O/hexane) 170–172° C.

$^1$H NMR [$(CD_3)_2SO$]: δ 9.78 (s, 1H, CONH), 9.62 (s, 1H, NH), 8.89 (s, 1H, aromatic), 8.56 (s, 1H, aromatic), 8.18 (t, J =1.9 Hz, 1H, H-2'), 7.88 (br d, J =8.2 Hz, 1H, H-6'), 7.34 (t, J =8.1 Hz, 1H, H-5'), 7.30 (s, 1H, aromatic), 7.27 (ddd, J =7.9, 1.4, 0.8 Hz, 1H, H-4'), 6.72 (dd, J =17.0, 10.2 Hz, 1H, CH$_2$CHCO), 6.33 (dd, J =17.0, 1.9 Hz, 1H, CH$_2$CHCO), 5.83 (dd, J =10.2, 1.9 Hz, 1H, CH$_2$CHCO), 4.27 (t, J =6.3 Hz, 2H, CH$_2$CH$_2$CH$_2$O), 3.58 (t, J 4.6 Hz, 4H, morpholino methylene), 2.48 (t, J =7.1 Hz, 2H, NCH$_2$CH$_2$CH$_2$), 2.38 (br s, 4H, morpholino methylene), 1.99 (quintet, J =6.7 Hz, 2H, CH$_2$CH$_2$CH$_2$).

$^{13}$C NMR: δ 163.49, 156.68, 154.96, 153.92, 149.19, 141.20, 131.58, 130.19, 127.16, 126.95, 125.52, 123.97, 121.03, 120.52, 116.78, 108.80, 107.28, 66.96, 66.14 (x2), 54.54, 53.28 (x2), 25.31.

Analysis calculated for C$_{24}$H$_{26}$BrN$_5$O$_3$.0.5 H$_2$O requires: C, 55.3; H, 5.2; N, 13.4%. Found: C, 55.3; H, 4.9; N, 13.3%.

EXAMPLE 22

N-[4-[(3-Methyl-phenyl)amino]-7-[3-(4-morpholino)-propoxy]quinazolin-6-yl]acrylamide A suspension of 7-fluoro-6-nitroquinazolone (2.40 g, 11.48 mmol) in neat SOCl$_2$ (25 mL) containing 2 drops of DMF was refluxed for 3 hours until it became clear. The excess SOCl$_2$ was then removed in vacuo and dry benzene was added to the residue and then distilled under reduced pressure to remove all traces of SOCl$_2$ giving crude 4-chloro-7-fluoro-6-nitroquinazoline, which was dissolved in dry CH$_2$Cl$_2$ (50 mL) and added to a stirred solution of m-toluidine in isopropanol (i-PrOH) (30 mL). The reaction mixture was stirred at 20° C. for 30 minutes and then hexane (200 mL) was added to precipitate the product as the HCl salt. The precipitate was filtered, washed with hexane, and then dissolved in MeOH/H$_2$O (4:1, 150 mL) with gentle warming. Excess Et$_3$N was then added to the solution followed by water (400 mL) to precipitate the product as the free base which was then filtered, washed with water and dried under reduced pressure to give 7-fluoro-4-[(3-methylphenyl)-amino]-6-nitroquinazoline (3.01 g, 88%) as a yellow powder, mp (CH$_2$Cl$_2$/hexane) 191–192° C.

$^1$H NMR [(CD$_3$)$_2$SO]: δ 10.38 (s, 1H, NH), 9.62 (d, J =8.1 Hz, 1H, H-5), 8.67 (s, 1H, H-2), 7.80 (d, J =12.6 Hz, 1H, H-8), 7.63 (br d, J =8.2 Hz, 1H, H-6'), 7.60 (br s, 1H, H-2'), 7.31 (t, J =7.8 Hz, 1H, H-5'), 7.03 (br d, J =7.5 Hz, 1H, H-4'), 2.35 (s, 3H, ArCH$_3$).

Analysis calculated for C$_{15}$H$_{11}$FN$_4$O$_2$ requires: C, 60.4; H, 3.7; N, 18.8%. Found: C, 60.6; H. 3.6; N, 19.0%.

To a solution of 3-morpholinopropan-1-ol (8.40 mmol, 1.22 g) in THF (40 mL) under N$_2$ was added sodium metal (11.8 mmol, 0.27 g). The resulting suspension was stirred at 20° C. for 2 hours and then cannulated into a solution of 7-fluoro-4-[(3-methylphenyl)amino]-6-nitroquinazoline (0.70 g, 2.35 mmol) in THF (30 mL) under N$_2$. The reaction procedure and workup above were followed to give after chromatography on silica gel eluting with MeOH/CH$_2$Cl$_2$/EtOAc (5:45:50) to MeOH/CH$_2$C0.50/EtOAc (3:7:10) 4-[(3-methylphenyl)amino]-7-[(3-morpholino)propyloxy]-6-nitroquinazoline (0.87 g, 88%) as a yellow powder, mp (CH$_2$Cl$_2$/hexane) 169–170° C.

$^1$H NMR [(CD$_3$)$_2$SO]: δ 10.00 (s, 1H, NH), 9.26 (s, 1H, aromatic), 8.62 (s, 1H, aromatic), 7.64 (br d, J =8.1 Hz, 1H, H-6'), 7.62 (br s, 1H, H-2'), 7.45 (s, 1H, aromatic), 7.29 (t, J =7.8 Hz, 1H, H-5'), 6.99 (br d, J =7.5 Hz, 1H, H-4'), 4.34 (t, J =6.1 Hz, 2H, CH$_2$CH$_2$CH$_2$O), 3.58 (t, J =4.6 Hz, 4H, morpholino methylene), 2.46 (t, J=7.0 Hz, 2H, NCH$_2$CH$_2$CH$_2$), 2.38 (br s, 4H, morpholino methylene), 2.35 (s, 3H, CH$_3$Ar), 1.94 (quintet, J =6.6 Hz, 2H, CH$_2$CH$_2$CH$_2$).

Analysis calculated for C$_{22}$H$_{25}$N$_5$O$_4$ requires C, 62.4; H, 6.0; N, 16.5%. Found: C, 62.2; H, 6.1; N, 16.5%.

A solution of the above nitroquinazoline (0.71 g, 1.68 mmol) in MeOH/EtOAc (2:1, 60 mL) was hydrogenated (60 psi) over Pd-C for 6 hours and then filtered through celite. The filtrate was then concentrated under reduced pressure to give 6-amino-4-[(3-methylphenyl)amino]-7-[(3-morpholino)propyloxy]quinazoline which was used without further characterization. To a stirred solution of this (0.7 g, 1.8 mmol), acrylic acid (6 mol, 10.8 mmol, 776 μL), and Et$_3$N (excess, 4.0 mL) in DMF (20 mL) under N$_2$ was added 1-(3-dimethylaminopropyl)-3-ethylcarbodiimide hydrochloride (EDCI.HCl) (3 mol, 5.38 mmol, 1.03 g). The standard procedure above was followed to give after chromatography on silica gel eluting with CH$_2$Cl$_2$/EtOAc (1:1) to MeOH/CH$_2$Cl$_2$/EtOAc (3:7:10), N-[4-[(3-methylphenyl)amino]-7-1(3-morpholino)propyloxy]quinazolin-6-yl]acrylamide (175 mg, 22%) as a cream powder, mp (EtOAc/Et$_2$O) 69–72° C.

$^1$H NMR [(CD$_3$)$_2$SO], (400 MHz): δ 9.60 (s, 1H, exchangeable), 9.59 (s, 1H, NH), 8.86 (s, 1H, H5), 8.48 (s, 1H, H2), 7.62 (br d, J=8.0 Hz, 1H, H-6'), 7.61 (br s, 1H, H-2'), 7.26 (s, 1H, H8), 7.25 (t, J=7.8 Hz, 1H, H-5'), 6.92 (br d, J=7.4 Hz, 1H, H-4'), 6.70 (dd, J=16.9, 10.2 Hz, 1H, CH$_2$CHCO), 6.32 (dd, J=16.9, 1.9 Hz, 1H, CH$_2$CHCO), 5.82 (dd, J=10.2, 1.9 Hz, 1H, CH$_2$CHCO), 4.26 (t, J=6.3 Hz, 2H, CH$_2$CH$_2$CH$_2$O), 3.58 (t, J=4.6 Hz, 4H, morpholino methylene), 2.48 (t, J=7.1 Hz, 2H, NCH$_2$CH$_2$CH$_2$), 2.38 (br s, 4H, morpholino methylene), 2.33 (s, 3H, CH$_3$Ar), 1.99 (quintet, J=6.7 Hz, 2H, CH$_2$CH$_2$CH$_2$).

Analysis calculated for C$_{25}$H$_{29}$N$_5$O$_3$.0.25 H$_2$O requires: C, 66.4; H, 6.6; N, 15.5%. Found: C, 66.3; H, 6.9; N, 15.9%.

EXAMPLE 23

N-[4-[(3-Methylphenyl)amino]-7-[3-(4,N-methyl-1,N-piperazino)propoxyl]quinazolin-6-yl]acrylamide Sodium metal (10.1 mmol, 0.23 g) was added to a solution of 3-N-(4-methylpiperazinyl)propan-1-ol (6.71 mmol, 1.06 g) in THF (15 mL) under N$_2$. The resulting suspension was stirred at 20° C. for 2 hours and then cannulated into a solution of 7-fluoro-4-[(3-methylphenyl)amino]-6-nitroquinazoline (0.50 g, 1.68 mmol) in THF (20 mL) under N$_2$. The dark red solution was then heated at reflux for 24 hours before being diluted with water and extracted with EtOAc. The combined organic extracts were dried over anhydrous Na$_2$SO$_4$, concentrated under reduced pressure and chromatographed on alumina eluting with EtOAc/hexane (1:1) to EtOAc (2:3:5), to give 4-[(3-methylphenyl) amino]-7-[3-N-(4-methylpiperazinyl)propyloxy]-6-nitroquinazoline (0.67 g, 91%) as a yellow powder, mp (Et$_2$O/hexane) 155–156° C.

$^1$H NMR [(CD$_3$)$_2$SO]: δ 10.00 (s, 1H, NH), 9.26 (s, 1H, H5, H2H5), 8.61 (s, 1H, H2), 7.64 (br d, J=8.4 Hz, 1H, H-6'), 7.62 (br s, 1H, H-2'), 7.43 (s, 1H, H8), 7.29 (t, J=7.8 Hz, 1H, H-5'), 6.99 (br d, J=7.4 Hz, 1H, H-4'), 4.32 (t, J=6.0 Hz, 2H, CH$_2$CH$_2$CH$_2$O), 2.44 (t, J=7.0 Hz, 2H, NCH$_2$CH$_2$CH$_2$), 2.39–2.28 (br s, 8H, piperazinyl methylene), 2.34 (s, 3H, CH$_3$Ar), 2.14 (s, 3H, CH$_3$N), 1.92 (quintet, J=6.6 Hz, 2H, CH$_2$CH$_2$CH$_2$).

Analysis calculated for CH$_{28}$N$_6$O$_3$ requires: C, 63.3; H, 6.5; N, 19.3%. Found: C, 63.4; H, 6.8; N, 19.6%.

A solution of the above nitroquinazoline (0.61 g, 1.40 mmol) in MeOH/EtOAc (2:1, 50 mL) was hydrogenated (60 psi) over Pd-C for 5 hours and then filtered through celite. The filtrate was then concentrated under reduced pressure and chromatographed on Grade III alumina eluting with MeOH/EtOAc (5:95) to give 6-amino-4-[(3-methylphenyl) amino]-7-[3-N-(4-methylpiperazinyl) propyloxy] quinazoline (361 mg) which appeared to rapidly discolor and was used without further characterization. To a stirred solution of this (0.36 g, 0.89 mmol), acrylic acid (6 mol. 5.53 mmol, 366 μL), and Et$_3$N (excess, 2.0 mL) in DMF (20 mL) under N$_2$ was added 1-(3-dimethylaminopropyl)-3-ethylcarbodiimide hydrochloride (EDCI.HCl) (3 mol, 2.66 mmol, 511 mg). The standard procedure above was followed to give, after chromatography on Grade III alumina eluting with EtOAc to MeOH/EtOAc (2:98), N-[4-[(3-methylphenyl)amino)-7-[3-N-(4-methylpiperazinyl)propyloxy]quinazolin-6-yl]acrylamide (65 mg, 16%) as a colorless glass, mp (Et$_2$O/hexane) 60–66° C.

$^1$H NMR ((CD$_3$)$_2$SO]: δ 9.60 (s, 1H, NH), 9.59 (s, 1H, NH), 8.86 (s, 1H, H5), 8.48 (s, 1H, H2), 7.62 (br d, J=8.0 Hz, 1H, H-6'), 7.62 (br s, 1H, H-2'), 7.25 (t, J=8.1 Hz, 1H, H-5'), 7.25 (s, 1H, H8), 6.92 (br d, J=7.5 Hz, 1H, H-4'), 6.70 (dd, J=17.0 Hz, J=10.2 Hz, 1H, CH$_2$CHCO), 6.31 (dd, J=16.9, 1.8 Hz, 1H, CH$_2$CHCO), 5.83 (dd, J=10.2, 1.8 Hz, 1H, CH$_2$CHCO), 4.24 (t, J=6.3 Hz, 2H, CH$_2$CH$_2$CH$_2$O), 2.47 (t, J=7.1 Hz, 2H, NCH$_2$CH$_2$CH$_2$), 2.41–2.28 (br s, 8H, piperazinyl methylene), 2.33 (s, 3H, CH$_3$Ar), 2.15 (s, 3H, CH$_3$N), 1.97 (quintet, J=6.8 Hz, 2H, CH$_2$CH$_2$CH$_2$).

EI HRMS (M$^+$) C$_{26}$H$_{32}$N$_6$O$_2$ requires 460.2587. Found: 460.2576.

EXAMPLE 24

N-[4-[(3-Bromophenyl)amino]-7-[3-(4,N-methyl-1,N-piperazino)propoxy]quinazolin-6-yl]acrylamide To a solution of 3-N-(4-methylpiperazinyl)propan-1-ol (8.81 mmol, 1.39 g) in THF (40 mL) under N$_2$ was added sodium metal (13.2 mmol, 0.30 g). The resulting suspension was stirred at 20° C. for 2 hours and then cannulated into a solution of 4-[(3-bromophenyl)amino]-7-fluoro-6-nitroquinazoline [*J Med Chem*, 1996(39):918] (0.80 g, 2.20 mmol) in THF (30 mL) under N$_2$. Identical reaction procedure and workup as in the previous example gave, after chromatography on silica gel eluting with MeOH/CH$_2$Cl$_2$/EtOAc (1:9:10) to MeOH/CH$_2$Cl$_2$/EtOAc (2:3:5), 4-[(3-bromophenyl)amino]-7-[3-N-(4-methylpiperazinyl)propyloxy]-6-nitroquinazoline (0.36 g, 33%) as a yellow powder, mp (trihydrochloride salt) (MeOH/Et$_2$O) 233° C. (dec).

$^1$H NMR (free base, (CD$_3$)$_2$SO]: δ 10.12 (s, 1H, NH), 9.24 (s, 1H, H5), 8.69 (s, 1H, H2), 8.19 (br s, 1H, H-2'), 7.88 (br d, J=7.8 Hz, 1H, H-6'), 7.47 (s, 1H, H8), 7.38 (t, J=7.8 Hz, 1H, H-5'), 7.34 (dt, J$_d$=8.0, J$_t$=1.3 Hz, 1H, H-4'), 4.33 (t, J=6.1 Hz, 2H, CH$_2$CH$_2$CH$_2$O), 2.45 (t, J=7.0 Hz, 2H, NCH$_2$CH$_2$CH$_2$), 2.42–2.29 (br s, 8H, piperazinyl methylene), 2.15 (s, 3H, CH$_3$N), 1.92 (quintet, J=6.7 Hz, 2H, CH$_2$CH$_2$CH$_2$).

Analysis calculated for C$_{22}$H$_{25}$BrN$_6$O$_3$.3HCl.H$_2$O requires: C, 42.0; H, 4.8; N, 13.4; Cl, 16.9%. Found: C, 42.1; H, 4.5; N, 13.3; Cl, 16.9%.

Freshly washed (1N HCl then distilled H$_2$O) iron powder (4 mol eq., 0.138 g) was added in portions to a refluxing solution of the above nitroquinazoline (0.31 g, 0.62 mmol) in EtOH/H$_2$O (2:1, 50 mL) containing glacial acetic acid (1.0 mL). The resulting suspension was heated at reflux with vigorous stirring for 20 minutes then cooled, basified by the addition of concentrated NH$_3$, and filtered through a pad of celite. The celite pad was washed with EtOH before the filtrate was concentrated under reduced pressure, diluted with water, and extracted with EtOAc. The combined organic extracts were dried over anhydrous Na$_2$SO$_4$, concentrated under reduced pressure and chromatographed on Grade III alumina, eluting with MeOH/EtOAc (5:95), to give 6-amino-4-[(3-bromophenyl)amino]-7-[3-N-(4-methylpiperazinyl)propyloxy]quinazoline (238 mg, 82%) as a cream powder, mp (CH$_2$Cl$_2$) 171–172° C.

$^1$H NMR [(CD$_3$)$_2$SO]: δ 9.36 (s, 1H, NH), 8.38 (s, 1H, H2), 8.22 (t, J=1.9 Hz, 1H, H-2'), 7.86 (ddd, J=8.2, 0.8, 1.9 Hz, 1H, H-6'), 7.40 (s, 1H, H5), 7.30 (t, J=8.0 Hz, 1H, H-5'), 7.20 (ddd, J=8.3, 1.0, 1.9 Hz, 1H, H-4'), 7.09 (s, 1H, H8), 5.34 (s, 2H, NH$_2$), 4.19 (t, J=6.2 Hz, 2H, CH$_2$CH$_2$CH$_2$O), 2.49 (obscured t, J=7 Hz, 2H, NCH$_2$CH$_2$CH$_2$), 2.43–2.29 (br s, 8H, piperazinyl methylene), 2.16 (s, 3H, CH$_3$N), 1.97 (quintet, J=6.8 Hz, 2H, CH$_2$CH$_2$CH$_2$).

Analysis calculated for C$_{22}$H$_{27}$BrN$_6$O.1.25H$_2$O requires: C, 53.5; H, 6.0; N, 17.0%. Found: C, 53.5; H, 5.7; N, 17.0%.

Acrylic acid (6 mol, 2.84 mmol, 195 μL) and Et$_3$N (excess, 1.0 mL) in DMA (20 mL) under N$_2$ was added to a stirred solution of the above aminoquinazoline (223 mg, 0.47 mmol), and 1-(3-dimethylaminopropyl)-3-ethylcarbodiimide hydrochloride (EDCI.HCl) (3 mol, 1.42 mmol, 273 mg). The standard procedure above was followed to give after chromatography on Grade III alumina eluting with EtOAc/hexane (1:1) to MeOH/EtOAc (2:98), N-[4-[(3-bromophenyl)amino]-7-[3-N-(4-methylpiperazinyl)propyloxy]quinazolin-6-yl]acrylamide (145 mg, 58%) as a cream powder, mp (CH$_2$Cl$_2$/Et$_2$O/hexane) 105–107° C.

$^1$H NMR [(CD$_3$)$_2$SO]: δ 9.78 (s, 1H, CONH), 9.61 (s, 1H, NH), 8.89 (s, 1H, H5), 8.56 (s, 1H, H2), 8.17 (t, J=1.9 Hz, 1H, H-2'), 7.87 (br d, J=8.5 Hz, 1H, H-6'), 7.34 (t, J=8.1 Hz, 1H, H-5'), 7.28 (s, 1H, H8), 7.27 (br dt, J$_d$=8 Hz, J$_t$=1 Hz, 1H, H-4'), 6.72 (dd, J=17.0, 10.3 Hz, 1H, CH$_2$CHCO), 6.32 (dd, J=17.0, 1.9 Hz, 1H, CH$_2$CHCO), 5.83 (dd, J=10.2, 1.9 Hz, 1H, CH$_2$CHCO), 4.26 (t, J=6.3 Hz, 2H, CH$_2$CH$_2$CH$_2$O), 2.47 (t, J=7.1 Hz, 2H, NCH$_2$CH$_2$CH$_2$), 2.42–2.27 (br s, 8H, piperazinyl methylene), 2.15 (s, 3H, CH$_3$N), 1.98 (quintet, J=6.7 Hz, 2H, CH$_2$CH$_2$CH$_2$).

Analysis calculated for C$_{25}$H$_{29}$BrN$_6$O$_2$.0.5H$_2$O requires: C, 56.2; H, 5.7; N, 15.7%. Found: C, 56.3; H, 5.6; N, 15.5%.

EXAMPLE 25

N-[4-[(3-Bromophenyl)amino]-7-[3-(1,N-imidazyl)propoxy]quinazolin-6-yl]acrylamide To a suspension of hexane-prewashed sodium hydride (5.50 mmol, 220 mg of a 60% dispersion in mineral oil) in THF (20 mL) was cannulated a solution of 3-N-(imidazoyl)propan-1-ol (4.84 mmol, 0.61 g) in THF (30 mL). The resulting suspension was stirred at 20° C. under N$_2$ for 2 hours during which time the required sodium alkoxide partially precipitated from solution, Solid 4-[(3-bromophenyl)amino]-7-fluoro-6-nitroquinazoline [*J Med Chem*, 1996(39):918] (0.80 g, 2.20 mmol) was then added to this suspension to give a dark red solution which was heated at reflux for 24 hours before being diluted with water and extracted with EtOAc. The combined organic extracts were dried over anhydrous Na$_2$SO$_4$, concentrated under reduced pressure and chromatographed on silica gel eluting with CH$_2$Cl$_2$/EtOAc (1:1) to MeOH/CH$_2$Cl$_2$/EtOAc (3:7:10), 4-[(3-bromophenyl)amino]-7-[3-N-(imidazoyl)propyloxy]-6-nitroquinazoline (524 mg, 51%) as a yellow powder, mp (CH$_2$Cl$_2$/hexane) 212–215° C.

$^1$H NMR [(CD$_3$)$_2$SO]: δ 10.16 (s, 1H, NH), 9.30 (s, 1H, H5), 8.70 (s, 1H, H2), 8.19 (t, J=1.6 Hz, 1H, H-2'), 7.88 (dt, J$_d$=7.8 Hz, J$_t$=1.5 Hz, 1H, H-6'), 7.63 (s, 1H, imidazoyl methine), 7.48 (s, 1H, H8), 7.39 (t, J=7.9 Hz, 1H, H-5'), 7.35 (dt, J$_d$=8.0 Hz, J$_t$=1.6 Hz, 1H, H-4'), 7.21 (s, 1H, imidazoyl methine), 6.90 (s, 1H, imidazoyl methine), 4.22 (t, J=6.0 Hz, 2H, CH$_2$CH$_2$CH$_2$), 4.18 (t, J=6.8 Hz, 2H, CH$_2$CH$_2$CH$_2$), 2.26 (quintet, J=6.4 Hz, 2H, CH$_2$CH$_2$CH$_2$).

Analysis calculated for $C_{20}H_{17}BrN_6O_3$ requires: C, 51.2; H, 3.6; N, 17.9%. Found: C, 51.0; H, 3.6; N, 17.6%.

Freshly washed (1N HCl then distilled $H_2O$) iron powder (4 mol, 0.241 g) was added in portions to a refluxing solution of the above 6-nitroquinazoline (0.51 g, 1.08 mmol) in EtOH/$H_2O$ (2:1, 60 mL) containing glacial acetic acid (0.7 mL). Identical reaction procedure and workup as in the previous example gave, after chromatography on Grade III alumina eluting with MeOH/EtOAc (5:95), 6-amino-4-[(3-bromophenyl)amino]-7-[3-N-(imidazoyl)propyloxy] quinazoline (389 mg, 82%) as a off-white powder, mp ($CH_2Cl_2/Et_2O$) 178–180° C.

$^1$H NMR [$(CD_3)_2SO$]: δ 9.37 (s, 1H, NH), 8.38 (s, 1H, H2), 8.22 (t, J=1.8 Hz, 1H, H-2'), 7.86 (br d, J=8.1 Hz, 1H, H-6'), 7.66 (s, 1H, imidazoyl methine), 7.40 (s, 1H, H5), 7.30 (t, J=8.1 Hz, 1H, H-5'), 7.23 (s, 1H, imidazoyl methine), 7.21 (br d, J=7.7 Hz, 1H, H-4'), 7.06 (s, 1H, H8), 6.90 (s, 1H, imidazoyl methine), 5.45 (s, 2H, $NH_2$), 4.28 (t, J=7.1 Hz, 2H, $CH_2CH_2CH_2$), 4.10 (t, J=5.8 Hz, 2H, $CH_2CH_2CH_2$), 2.27 (quintet, J=6.5 Hz, 2H, $CH_2CH_2CH_2$).

Analysis calculated for $C_{20}H_{19}BrN_6O \cdot 0.5H_2O$ requires: C, 53.6; H, 4.5; N, 18.7%. Found: C, 53.6; H, 4.5; N, 18.6%.

To a stirred solution of 6-amino-4-[(3-bromophenyl) amino]-7-[3-N-(imidazoyl)propyloxy]quinazoline (383 mg, 0.87 mmol), acrylic acid (6 mol, 5.23 mmol, 359 µL), and pyridine (excess, 1.0 mL) in DMA (20 mL) under $N_2$ was added 1-(3-dimethylaminopropyl)-3-ethylcarbodiimide hydrochloride (EDCI.HCl) (5 mol, 4.36 mmol, 838 mg). The standard procedure above was followed to give after chromatography on Grade III alumina eluting with EtOAc/hexane (1:1) to MeOH/EtOAc (5:95), N-[4-[(3-bromophenyl)amino]-7-[3-N-(imidazoyl)propyloxy] quinazolin-6-yl]acrylamide (9 mg, 2%) as a cream powder, mp ($CH_2Cl_2/Et_2O$/hexane) 235–237° C.

$^1$H NMR [$(CD_3)_2SO$]: δ 9.79 (s, 1H, CONH), 9.60 (s, 1H, NH), 8.88 (s, 1H, H5), 8.55 (s, 1H, H2), 8.18 (t, J=1.9 Hz, 1H, H-2'), 7.87 (ddd, J=8.2, 1.8, 1.0 Hz, 1H, H-6'), 7.64 (s, 1H, imidazoyl methine), 7.34 (t, J=8.0 Hz, 1H, H-5'), 7.28 (br dt, $J_d$=8.0 Hz, $J_t$=1.2 Hz, 1H, H-4'), 7.27 (s, 1H, H8), 7.21 (t, J=1.3 Hz, 1H, imidazoyl methine), 6.89 (br s, 1H, imidazoyl methine), 6.73 (dd, J=17.0, 10.2 Hz, 1H, $CH_2CHCO$), 6.34 (dd, J=17.0, 1.8 Hz, 1H, $CH_2CHCO$), 5.85 (dd, J=10.2, 1.8 Hz, 1H, $CH_2CHCO$), 4.22 (t, J=6.9 Hz, 2H, $CH_2CH_2CH_2$), 4.14 (t, J=6.0 Hz, 2H, $CH_2CH_2CH_2$), 2.27 (quintet, J=6.4 Hz, 2H, $CH_2CH_2CH_2$).

Analysis calculated for $CH_{23}H_{21}BrN_6O_2 \cdot 0.75H_2O$ requires: C, 54.5; H, 4.5; N, 16.6%. Found: C, 54.5; H, 4.4; N, 16.2%.

EXAMPLE 26

N-[4-[(3-Bromophenyl)amino]-7-[4-(N,N-dimethylamino)butoxy]quinazolin-6-yl]acrylamide To a suspension of hexane prewashed sodium hydride (11.0 mmol, 440 mg of a 60% dispersion in mineral oil) in THF (20 mL) was cannulated a solution of 4-(N,N-dimethylamino)butan-1-ol (8.80 mmol, 1.03 g) in THF (30 mL). The resulting suspension was stirred at 20° C. under $N_2$ for 2 hours and then cannulated into a solution of 4-[(3-bromophenyl)amino]-7-fluoro-6-nitroquinazoline (*J Med Chem*, 1996;39:918–928) (0.80 g, 2.20 mmol) in THF (30 mL) under $N_2$. The dark red solution was then heated at reflux overnight. Identical workup as above gave, after chromatography on grade III alumina eluting with EtOAc to MeOH/EtOAc (5:95) to give 6-amino-4-[(3-bromophenyl) amino]-7-[4(N,N-dimethylamino)butyloxy]quinazoline (310 mg, 33%) as a pale brown powder, mp ($CH_2Cl_2$/hexane) 155–156° C.

$^1$H NMR [$(CD_3)_2SO$], (400 MHz): δ 9.36 (s, 1H, NH), 8.39 (s, 1H, aromatic), 8.23 (t, J=2.0 Hz, 1H, H-2'), 7.86 (br d, J=8.0 Hz, 1H, H-6'), 7.41 (s, 1H, aromatic), 7.30 (t, J=8.1 Hz, 1H, H-5'), 7.20 (ddd, J=8.2 Hz, J=0.8 Hz, J=1.8 Hz, 1H, H-4'), 7.09 (s, 1H, aromatic), 5.32 (s, 2H, $NH_2$), 4.17 (t, J=6.2 Hz, 2H, $CH_2CH_2CH_2CH_2O$), 2.47 (t, J=7.3 Hz, 2H, $NCH_2CH_2CH_2CH_2$), 2.15 (s, 6H, $N(CH_3)_2$), 1.84 (quintet, J=6.4 Hz, 2H, $CH_2CH_2CH_2CH_2$), 1.62 (quintet, J=6.9 Hz, 2H, $CH_2CH_2CH_2CH_2$).

Analytical calculated for $C_{20}H_{24}BrN_5O \cdot ½ H_2O$ requires: C, 54.7; H, 5.7; N, 15.9%. Found: C, 54.3; H, 5.8; N, 15.8%.

To a stirred solution of the above 6-aminoquinazoline (276 mg, 0.64 mmol), acrylic acid (6 mol eq., 3.85 mmol, 264 mL), and $Et_3N$ (excess, 1.0 mL) in DMA (10 mL) under $N_2$ was added 1-(3-dimethylaminopropyl)-3-ethylcarbodiimide hydrochloride (EDCI.HCl) (3 mol eq., 1.92 mmol, 369 mg). The standard procedure above was followed to give after chromatography on grade III alumina eluting with EtOAc/hexane (1:1) to MeOH/EtOAc (3:97), N-[4-[(3-bromophenyl)amino]-7-[4-(N,N-dimethylamino) butyloxy]-quinazolin-6-yl]acrylamide (98 mg, 32%) as a cream powder, mp ($CH_2Cl_2/Et_2O$) 112–115° C.

$^1$H NMR [$(CD_3)_2SO$], (400 MHz): δ 9.77 (s, 1H, CONH), 9.62 (s, 1H, NH), 8.88 (s, 1H, aromatic), 8.56 (s, 1H, aromatic), 8.17 (t, J=1.9 Hz, 1H, H-2'), 7.87 (ddd, J=8.2 Hz, J=1.8 Hz, J=1.0 Hz, 1H, H-6'), 7.34 (t, J=8.0 Hz, 1H, H-5'), 7.29 (s, 1H, aromatic), 7.27 (ddd, J=8.2 Hz, J=1.8 Hz, J=1.0 Hz, 1H, H-4'), 6.71 (dd, J=17.1 Hz, J=10.2 Hz, 1H, $CH_2CHCO$), 6.32 (dd, J=17.0 Hz, J=1.9 Hz, 1H, $CH_2CHCO$), 5.82 (dd, J=10.2 Hz, J=1.9 Hz, 1H, $CH_2CHCO$), 4.24 (t, J=6.6 Hz, 2H, $CH_2CH_2CH_2CH_2O$), 2.27 (t, J=7.2 Hz, 2H, $NCH_2CH_2CH_2CH_2$), 2.12 (s, 6H, $N(CH_3)_2$), 1.85 (quintet, J=6.9 Hz, 2H, $CH_2CH_2CH_2CH_2$), 1.60 (quintet, J=7.4 Hz, 2H, $CH_2CH_2CH_2CH_2$).

Analysis calculated for $C_{23}H_{26}BrN_5O_2 \cdot 1.25 H_2O$ requires: C, 54.5; H, 5.7; N, 13.8%. Found: C, 54.5; H, 5.3; N, 13.7%.

EXAMPLE 27

N-[4-[(3-Bromophenyl)amino]quinazolin-6-yl]-N-[3-morpholinopropyl]acrylamide

A stirred solution of N-[4-[(3-bromophenyl)amino] quinazolin-6-yl]acrylamide (1.78 g, 4.82 mmol), morpholine (excess, 4.0 mL) and p-toluenesulfonic acid (catalytic) in THF (50 mL) was heated at 50° C. for 4 hours before being concentrated under reduced pressure, diluted with water and extracted with EtOAc. The combined organic extracts were washed with brine, dried over anhydrous $Na_2SO_4$, concentrated under reduced pressure, and chromatographed on silica gel eluting with MeOH/$CH_2Cl_2$/EtOAc (15:40:45) to give N-[4-[(3-bromophenyl)amino] quinazolin-6-yl]-3-morpholino-propylamide (1.86 g, 78%) as a cream powder, mp (EtOAc) 184–186° C.

$^1$H NMR [$(CD_3)_2SO$]: δ 10.37 (s, 1H, CONH), 9.91 (s, 1H, NH), 8.72 (d, J=1.9 Hz, 1H, H-5), 8.58 (s, 1H, H-2), 8.17 (t, J=2.1 Hz, 1H, H-2'), 7.86 (m, 2H, H-7, 6'), 7.78 (d, J=8.9 Hz, 1H, H-8), 7.35 (t, J=8.0 Hz, 1H, H-5'), 7.29 (dt, $J_t$=1.2 Hz, $J_d$=8.0 Hz, 1H, H-4'), 3.40 (t, J=4.6 Hz, 4H, morpholino methylene), 2.69 (t, J=6.6 Hz, 2H, $NCH_2CH_2CONH$), 2.58 (t, J=6.6 Hz, 2H, $NCH_2CH_2CONH$), 2.44 (br s, 4H, morpholino methylene).

$^{13}$C NMR: δ 170.24, 157.18, 152.86, 146.48, 141.13, 136.87, 130.21, 128.39, 127.01, 125.74, 124.21, 121.03, 120.79, 115.40, 111.46, 66.09 (×2), 54.04, 53.00 (×2), 33.66.

Analysis calculated for $C_{21}H_{22}BrN_{52}$ requires: C, 55.3; H, 4.9; N, 15.3%. Found: C, 55.1; H, 5.2; N, 15.2%.

To a stirred solution of the above amide (0.85 g, 1.86 mmol) in THF (30 mL) under $N_2$ at 0° C. was added $BH_3.DMS$ (2 mol eq., 372 µL of a 10 M solution) dropwise. The resulting solution was allowed to warm to 25° C. and was stirred for 2 hours before being quenched by the cautious addition of 1N HCl (40 mL). The reaction mixture was then stirred at 50° C. for 2 hours, basified by the addition of saturated $Na_2CO_3$, and extracted with EtOAc. The combined organic extracts were washed with brine, dried over anhydrous $Na_2SO_4$, concentrated under reduced pressure, and chromatographed on silica gel eluting with $MeOH/CH_2Cl_2/EtOAc$ (3:8:8) to give 4-[(3-bromophenyl)amino]-6-[(3-morpholinopropyl)amino]quinazoline (130 mg, 16%) as a yellow glass (ca. 90% pure by NMR). This was used without further purification.

$^1H$ NMR [$(CD_3)_2SO$]: δ 9.40 (s, 1H, NHAr), 8.37 (s, 1H, H-2), 8.17 (t, J=1.9 Hz, 1H, H-2'), 7.91 (br d, J=8.2 Hz, 1H, H-6'), 7.54 (d, J=9.0 Hz, 1H, H-8), 7.34 (t, J=8.0 Hz, 1H, H-5'), 7.27 (m, 2H, H-4', 7), 7.16 (d, J=2.2 Hz, 1H, H-5), 6.25 (t, J=5.1 Hz, 1H, $CH_2NH$), 3.59 (t, J=4.5 Hz, 4H, morpholino methylene), 3.22 (q, J=6.0 Hz, 1H, $CH_2NH$), 2.45 (t, J=6.9 Hz, 2H, $CH_2CH_2CH_2NH$), 2.39 (br s, 4H, morpholino methylene), 1.82 (quintet, J=7.0 Hz, 2H, $CH_2CH_2CH_2$).

To a stirred solution of the above amine (133 mg, 0.30 mmol), acrylic acid (4 mol eq., 1.20 mmol, 83 µL), and $Et_3N$ (excess, 0.5 mL) in DMF (5.0 mL) under $N_2$ was added 1-(3-dimethylaminopropyl)-3-ethylcarbodiimide hydrochloride (EDCI.HCl) (2.0 mol, 0.60 mmol, 115 mg). The standard procedure above was followed to give, after chromatography on silica gel eluting with $EtOAc:CH_2Cl_2$ (1:1) to $MeOH/CH_2Cl_2/EtOAc$ (3:7:10), N-[4-[(3-bromophenyl)amino]quinazolin-6-yl]-N-[3-morpholinopropyl]acrylamide (39 mg, 26%) as a cream powder, mp ($CH_2Cl_2$/hexane) 171–175° C.

$^1H$ NMR [$(CD_3)_2SO$]: δ 9.86 (s, 1H, NH), 8.70 (s, 1H, H-2), 8.52 (d, J=2.0 Hz, 1H, H-5), 8.20 (t, J=1.9 Hz, 1H, H-2'), 7.91 (br d, J=8.6 Hz, 1H, H-6'), 7.89 (d, J=8.9 Hz, 1H, H-8), 7.79 (dd, J=8.8 Hz, J=2.1 Hz, 1H, H-7), 7.38 (t, J=7.9 Hz, 1H, H-5'), 7.33 (dt, $J_d$=8.4 Hz, $J_t$=1.7 Hz, 1H, H-4'), 6.22 (dd, J=16.7, 2.3 Hz, 1H, $CH_2CHCO$), 6.05 (br s, 1H, $CH_2CHCO$), 5.61 (br d, J=8.8 Hz, 1H, $CH_2CHCO$), 3.87 (t, J=7.4 Hz, 2H, $CH_2NRCO$), 3.49 (t, J=4.5 Hz, 4H, morpholino methylene), 2.28 (t, J=7.1 Hz, 2H, $CH_2CH_2CH_2NRCO$), 2.27 (br s, 4H, morpholino methylene), 1.69 (quintet, J=7.3 Hz, 2H, $CH_2CH_2CH_2$).DEI HRMS ($M^+$).

Calculated for $C_{24}H_{26}Br^{81}N_5O_2$: 497.1249 Found: 497.1250.

EXAMPLE 28

N-[4-(3-Bromo-phenylamino)-quinazolin-6-yl] propanamide

To a solution of 6-amino-4-[(3-bromophenyl)amino]quinazoline (157 mg, 0.5 mmol) in dry THF (3 mL) stirred under $N_2$ at 25° C. was added dropwise propionyl chloride (0.05 mL, 0.58 mmol). A yellow solid formed at once. After 45 minutes the solid was collected by filtration and washed with ether and dried. Recrystallized from wet methanol afforded the desired product (97 mg, 47%), mp 265–266° C.

$^1H$ NMR [$(CD_3)_2SO$]: δ 11.3 (brs, 1H, NH), 10.53 (s, 1H, NH), 9.02 (s, 1H, H5), 8.88 (s, 1H, H2), 8.00–7.97 (m, 2H, H7, H2'), 7.89 (d, J=9.1 Hz, 1H, H8), 7.71 (d, J=7.8 Hz, 1H, H6'), 7.50 (d, J=8.3 Hz, 1H, H4'), 7.45 (t, J=8.1 Hz, 1H, H5'), 2.45 (q, J=7.3 Hz, 2H, $CH_2$), 1.15 (t, J=7.5 Hz, 3H, $CH_3$).

Mass Spectrum (CI): 373 (84, $^{81}BrMH^+$), 372 (43, $^{81}BrM^+$), 371 (100, $^{79}BrMH^+$), 370 (28, $^{79}BrM^+$).

Calculated for $C_{17}H_{15}N_4BrO.HCl.0.5H_2O$: C, 49.00; H, 4.11; N, 13.45%. Found: C, 48.89; H, 3.97; N, 13.36%.

EXAMPLE 29

N-[4-[(3-Bromo-phenyl)amino]quinazolin-6-yl] methacrylamide

To a stirred solution of 6-amino-4-[(3-bromophenyl)amino]quinazoline (J Med Chem, 1995;38:3482) (0.50 g, 1.59 mmol) in THF (20 mL) under nitrogen was added $Et_3N$ (excess, 1.0 mL), a catalytic amount of DMAP and methacryloyl chloride (1.1 mol eq., 1.75 mmol, 171 µL) dropwise. The reaction was stirred at 25° C. for 1.5 hours over which time two further amounts (50 µL) of methacryloyl chloride were added. The reaction was then diluted with saturated $NaHCO_3$ and extracted with EtOAc. The combined organic extracts were dried over anhydrous $Na_2SO_4$, concentrated under reduced pressure and chromatographed on silica gel eluting with $CH_2Cl_2/EtOAc$ (1:1) to MeOH/$CH_2Cl_2$/EtOAc (5:45:50). Recrystallization from EtOAc gave N-[4-[(3-bromophenyl)amino]quinazolin-6-yl]-2-methylacrylamide (195 mg, 32%) as a cream powder, mp 244–245° C.

$^1H$ NMR [$(CD_3)_2SO$]: δ 10.15 (s, 1H, CONH), 9.90 (s, 1H, NH), 8.80 (br s, 1H, H-5), 8.60 (s, 1H, H-2), 8.20 (br s, 1H, H-2'), 7.97 (br d, J=8.6 Hz, 1H, H-7), 7.89 (br d, J=7.7 Hz, 1H, H-6'), 7.80 (d, J=8.9 Hz, 1H, H-8), 7.35 (t, J=8.0 Hz, 1H, H-5'), 7.30 (br d, J=7.5 Hz, 1H, H-4'), 5.94 (s, 1H, $CH_2C(CH_3)CO$), 5.62 (s, 1H, $CH_2C(CH_3)CO$), 2.02 (s, 3H, $CH_2C(CH_3)CO$).

$^{13}C$ NMR: δ 166.71, 157.17, 153.07, 146.69, 141.09, 139.93, 136.62, 130.23, 128.24, 128.11, 125.73, 124.11, 121.04, 120.66, 120.51, 115.19, 113.28, 18.60.

Analysis calculated for $C_{18}H_{15}BrN_4O$ requires: C, 56.4; H, 4.0; N, 14.6%. Found: C, 56.1; H, 3.9; N, 14.5%.

EXAMPLE 30

N-[4-(3-Bromo-phenylamino)-quinazolin-6-yl] ethenylsulfonamide

To a stirred solution of 6-amino-4-[(3-bromophenyl)amino]quinazoline (J Med Chem, 1995;38:3482) (0.30 g, 0.95 mmol) in THF (20 mL) under nitrogen was added $Et_3N$ (3.5 mol eq., 3.33 mmol, 245 µL), a catalytic amount of DMAP and chloroethanesulfonyl chloride (1.2 mol eq., 1.14 mmol, 119 µL) dropwise. The reaction was stirred at 25° C. for 1 hour and then diluted with saturated $NaHCO_3$ and extracted with EtOAc. The combined organic extracts were washed with brine, dried over anhydrous $Na_2SO_4$, concentrated under reduced pressure, and chromatographed on silica gel eluting with $MeOH/CH_2Cl_2/EtOAc$ (3:47:50). Crystallization from $CH_2Cl_2$/hexane gave N-[4-[(3-bromophenyl)amino]quinazolin-6-yl]vinylsulfonamide (210 mg, 54%) as a cream powder, mp 217° C. (dec).

$^1H$ NMR [$(CD_3)_2SO$]: δ 10.31 (s, 1H, $SO_2NH$), 9.96 (s, 1H, NH), 8.60 (s, 1H, H-2), 8.20 (d, J=2.0 Hz, 1H, H-5), 8.14 (br s, 1H, H-2'), 7.85 (br d, J=7.9 Hz, 1H, H-6'), 7.81 (d, J=8.9 Hz, 1H, H-8), 7.67 (dd, J=8.9, 2.1 Hz, 1H, H-7), 7.37 (t, J=8.0 Hz, 1H, H-5'), 7.32 (br d, J=8.1 Hz, 1H, H-4'), 6.90 (dd, J=16.4, 9.8 Hz, 1H, $CH_2CHSO_2$), 6.17 (d, J=16.4 Hz, 1H, $CH_2CHSO_2$), 6.06 (d, J=9.8 Hz, 1H, $CH_2CHSO_2$).

$^{13}$C NMR: δ 157.18, 153.47, 147.17, 140.83, 136.02, 135.48, 130.25, 129.03, 128.44, 127.77, 126.08, 124.60, 121.18, 121.03, 115.43, 114.01.

Analysis calculated for $C_{16}H_{13}BrN_4O_2S$ requires: C, 47.4; H, 3.2; N, 13.8%. Found: C, 47.7; H, 3.1; N, 13.8%.

EXAMPLE 31

N-[4-[(3-Bromophenyl)amino]quinazolin-6-yl]-E-but-2-enamide

To a solution of 6-amino-4-[(3-bromophenyl)amino] quinazoline (316 mg, 1.0 mmol) in THF (6 mL) stirred under $N_2$ at 0° C. was added trans-crotonyl chloride. A yellow solid formed upon addition. The solid was collected by Buchner filtration after 2.5 hours and sonicated with EtOAc to give the title compound (216 mg, 52%), mp 279–281° C.

$^1$H NMR [$(CD_3)_2SO$]: δ 11.55 (brs, 1H, NH), 10.78 (s, 1H, NH), 9.17 (d, J=1.9 Hz, 1H, H5), 8.97 (s, 1H, H2), 8.12 (dd, J=9.1, 2.0 Hz, 1H, H7), 8.05 (t, J=1.9 Hz, 1H, H2'), 7.99 (d, J=9.0 Hz, 1H, H8), 7.76 (dd, J=8.1, 2.0 Hz, 1H, H6'), 7.58 (dd, J=8.6, 1.7 Hz, 1H, H4'), 7.52 (t, J=8.1 Hz, 1H, H5') 7.036.–6.94 (m, 1H, [(CO)CH=], 6.34 (dd, J=15.1, 1.7 Hz, 1H, CH=CHCH$_3$), 1.98 (dd, J=6.8, 1.4 Hz, 3H, CH$_3$).

Mass Spectrum (CI): 385 (89, $^{81}$BrMH$^+$), 384 (51, $^{81}$BrM$^+$), 383 (100, $^{79}$BrMH$^+$), 382 (37, $^{79}$BrM$^+$).

Calculated for $C_{18}H_{15}N_4BrO\cdot HCl$: C, 51.51; H, 3.84; N, 13.35%. Found: C, 51.29; H, 3.52; N, 13.13%.

EXAMPLE 32

N-[4-[(3-Bromophenyl)amino]quinazolin-6-yl]-4,4,4-trifluoro-E-but-2-enamide 1-(3-dimethylaminopropyl)-3-ethylcarbodiimide hydrochloride (192 mg, 1.0 mmol) was added to a solution of 6-amino-4[(3-bromophenyl)amino]quinazoline (158 mg, 0.5 mmol) and 4,4,4,-trifluorobut-2-enoic acid (153 mg, 1.1 mmol) in THF/DMF (4:1, 2.5 mL), stirred under nitrogen at 0° C. After 1 hour water (10 mL) was added and after 15 minutes the precipitate was collected by Buchner filtration. The residue was rinsed with water (2×5 mL) and ether (10 mL) and air dried. The solid was suspended in EtOAc, (10 mL) refluxed briefly, and sonicated for 10 minutes, and the solid was collected by Buchner filtration, rinsed with EtOAc (5 mL) and dried in a vacuum oven at 75° C. for 1.5 hours to give N-[4-[(3-bromophenyl)amino]quinazolin-6-yl]4,4,4-trifluorobut-2-enamide 0.4 hydrochloride (76 mg, 33%) as a light yellow solid, mp 273–278° C.

Calculated for $C_{18}H_{13}BrF_3N_4O\cdot 0.4$ HCl: C, 47.85; H, 2.77; N, 12.40%. Found: C, 47.89, H, 2.66; N, 12.27%.

$^1$H NMR [$(CD_3)_2SO$]: δ 11.09 (brs, 1H, NH), 10.43 (s, 1H, NH), 8.90 (s, 1H, H2), 8.70 (s, 1H, H5), 8.11 (s, 1H, H2'), 7.97 (dd, J=2.5, 9.2 Hz, 1H, H7), 7.87 (d, J=9.0 Hz, 1H, H8), 7.81 (d, J=6.9 Hz, 1H, H6'), 7.41–7.33 (m, 2H, H5' & H4'), 7.11 (d, J=16.4 Hz, 1H, CH=CHCF$_3$), 7.03 (dq, $J_d$=16.4 Hz, $J_q$=6.4 Hz, 1H, CH=CHCF$_3$).

Mass Spectrum (CI) 439 (78 $^{81}$BrM$^+$), 437 (100 $^{79}$BrM$^+$).

EXAMPLE 33

N-[4-[(3-Bromophenyl)amino]quinazolin-6-yl]-propynamide 1-(3-Dimethylaminopropyl)-3-ethylcarbodiimide hydrochloride (200 mg, 1.04 mmol) was added to a solution of 6-amino-4-[(3-bromophenyl)-amino]quinazoline (158 mg, 0.5 mmol) and propiolic acid (0.08 mL, 1.1 mmol) in DMF (1.5 mL) stirred under $N_2$ at 0° C. The resulting solution was stirred at 0° C. for 30 minutes and quenched with water. The formed fine solid was collected by Buchner filtration then dissolved in methanol and purified by preparative tlc on silica, eluting with 10% MeOH/CHCl$_3$. The title compound was isolated as a yellow solid (21 mg, 12%), mp >310° C.

$^1$H NMR [$(CD_3)_2SO$]: δ 11.18 (brs, 1H, NH), 9.94 (s, 1H, NH), 8.75 (s, 1H, H5), 8.59 (s, 1H, H2), 8.15 (s, 1H, H2'), 7.85–7.79 (m, 3H, H7, H8, H6'), 7.37–7.28 (m, 2H, H5', H4'), 4.53 (s, 1H, CH).

Mass Spectrum (CI): 369 (47, $^{81}$BrMH$^+$), 368 (24, $^{81}$BrM$^+$), 367 (50, $^{79}$BrMH$^+$), 366 (13, $^{79}$BrM$^+$), 91 (100).

Calculated for $C_{17}H_{11}N_4BrO$: C, 55.61; H, 3.02; N, 15.26%. Found: C, 55.40; H, 2.84; N, 15.18%.

EXAMPLE 34

N-[4-[(3-Bromophenyl)amino]quinazolin-6-yl]but-2-ynamide

To a solution of 2-butynoic acid (196 mg, 2.3 mmol) and 1-(3-dimethylaminopropyl)-3-ethylcarbodiimide hydrochloride (385 mg, 2.0 mmol) in DMF (5 mL) stirring at 25° C. for 20 minutes was added 6-amino-4-[(3-bromophenyl) amino]quinazoline (316 mg, 1.0 mmol). The resulting solution was stirred under $N_2$ at 25° C. for 14 hours further 1-(3-dimethylaminopropyl)-3-ethylcarbodiimide hydrochloride (206 mg, 1.0 mmol) and 2-butynic acid (82 mg, 1.0 mmol) were. After another 8 hours further, 1-(3-dimethylaminopropyl)-3-ethylcarbodiimide hydrochloride (197 mg, 1.0 mmol) and the acid (93 mg, 1.0 mmol) were added to the reaction. After stirring at 25° C. a further 12 hours, the reaction was quenched with water. The yellow precipitate was collected, sonicated with acetone, treated with triethyl amine and purified by preparative tlc on silica, eluting with 1:1 EtOAc/acetone. The desired product was isolated as a yellow solid (20 mg, 4.7%), mp 281–283° C.

$^1$H NMR [$(CD_3)_2SO$]: δ 10.97 (brs, 1H, NH), 9.93 (s, 1H, NH), 8.76 (s, 1H, H5), 8.57 (s, 1H, H2), 8.14 (s, 1H, H2'), 7.84–7.76 (m, 3H, H7, H8, H4'), 7.34 (t, J=8.1 Hz, 1H, H5'), 7.29 (d, J=7.8 Hz, 1H, H6'), 2.09 (s, 3H, CH$_3$).

Mass Spectrum (APCI): 383 (100, $^{81}$BrMH$^+$), 382 (23, $^{81}$BrM$^+$), 381 (95, $^{79}$BrMH$^+$).

Calculated for $C_{18}H_{13}N_4BrO\cdot 0.3HCl\cdot 0.6C_3H_6O$: C, 55.69; H, 3.99; N, 13.12%. Found: C, 55.67; H, 3.96; N, 12.93%.

EXAMPLE 35

N-[4-(3-Bromo-phenylamino)-pyrido[4,3-d]pyrimidin-7-yl]-acrylamide

To a stirred solution of 7-amino-4-[(3-bromophenyl) amino]pyrido[4,3-d]pyrimidine (*J Med Chem*, 1995;38:3780) (140 mg, 0.46 mmol), DMAP (14 mg) and Et$_3$N (excess, 2.0 mL) at 0° C. under $N_2$ was added acryloyl chloride (4.8 mol eq., 182 μL) dropwise over 4 hours. The reaction was then stirred at 20° C. diluted with water and extracted with EtOAc. The combined organic extracts were washed with brine, dried over anhydrous $Na_2SO_4$ and concentrated under reduced pressure before being chromatographed on silica gel eluting with MeOH/CH$_2$Cl$_2$/EtOAc (5:45:50), to give N-[4-[(3-bromophenyl)amino]pyrido[4,3-d]pyrimidin-7-yl]acrylamide (12 mg, 7%) as a cream powder, mp (CH$_2$Cl$_2$/hexane) 215–220° C. (dec).

$^1$H NMR [$(CD_3)_2SO$]: δ 11.15 (s, 1H, CONH), 10.25 (s, 1H, NH), 9.67 (s, 1H, H5), 8.71 (s, 1H, H2), 8.40 (s, 1H,

H8), 8.21 (t, J=1.9 Hz, 1H, H-2'), 7.88 (dt, $J_d$=7.6 Hz, $J_t$=1.5 Hz, 1H, H-6'), 7.38 (t, J=7.7 Hz, 1H, H-5'), 7.36 (dt, $J_d$=7.7 Hz, $J_t$=1.5 Hz, 1H, H-4'), 6.68 (dd, J=17.1, 10.2 Hz, 1H, CH$_2$CHCO), 6.39 (dd, J=17.0, 1.8 Hz, 1H, CH$_2$CHCO), 5.86 (dd, J=10.1, 1.8 Hz, 1H, CH$_2$CHCO).

EXAMPLE 36

N-[4-(3-Bromo-phenylamino)-pyrido[3,4-d]pyrimidin-6yl]-acrylamide

A suspension of 6-fluoropyrido[3,4-d]pyrimidine-4(3H)-one (U.S. patent application Ser. No. 08/358,352, 1994) (1.65 g) in 50 mL thionyl chloride and several drops of dimethyl formamide was heated under reflux until a clear solution was obtained (20 minutes), and then for a further 30 minutes. The volatiles were removed under reduced pressure, and the residue was dissolved in dichloromethane and washed with aqueous Na$_2$CO$_3$. The solvent was dried and removed to give crude 4-chloro-6-fluoropyrido[3,4-d]pyrimidine which was dissolved in 2-propanol (50 mL) containing 3-bromoaniline (2.1 g). The mixture was heated under reflux for 15 minutes to give a precipitate, which was redissolved by the addition of triethylamine. After the addition of water, the solution was concentrated and cooled to give 4-[(3-bromophenyl)amino]-6-fluoropyrido[3,4-d]pyrimidine, (2.29 g), mp (MeOH) 219.5–221° C.

A mixture of 4-[(3-bromophenyl)amino]-6-fluoropyrido[3,4-d]pyrimidine (0.48 g) and 4-methoxybenzylamine (10.3 g) in ethanol (50 mL) was heated to 100° C. for 5 days. The resulting product was chromatographed on silica gel, eluting with CH$_2$Cl$_2$:EtOAc (3:1), to give 4-[(3-bromophenyl)amino]-6-[(4-methoxyphenyl)methylamino] pyrido[3,4-d]pyrimidine (0.18 g,) mp (aqueous methanol), 178–179.5° C. A 0.10 g portion of this was dissolved in 5 mL trifluoroacetic acid and heated under reflux for 1 hour, and the mixture was evaporated to dryness. The residue was partitioned between EtOAc and aqueous ammonia, and the crude product was chromatographed on alumina, eluting with CH$_2$Cl$_2$:MeOH (97:3) to give 6-amino-4-[(3-bromophenyl)amino]pyrido[3,4-d]pyrimidine (0.040 g,), mp (CH$_2$Cl$_2$) 241.5–242° C.

To a solution of 6-amino-4-[(3-bromophenyl)amino] pyrido[3,4-d]pyrimidine (J Med Chem, 1996;39:1823) (455 mg, 1.50 mmol) in dry THF (50 mL) at 0° C. under N$_2$ was added Et$_3$N (22.5 mmol, 1.61 mL), a catalytic amount of DMAP (45 mg) and acryloyl chloride (4.50 mmol, 366 μL). The reaction mixture was stirred for 1 hour and then additional acryloyl chloride (100 μL) was added and the reaction was allowed to warm to room temperature and stirred for another hour before being worked up as in the previous example, to give after column chromatography on silica gel eluting with MeOH/EtOAc (5:95), N-[4-[(3-bromophenyl)amino]pyrido[3,4-d]pyrimidin-6-yl] acrylamide (20 mg, 37%) as a cream powder, mp (EtOAc/MeOH) 238–245° C. (dec.).

$^1$H NMR [(CD$_3$)$_2$SO]: δ 11.07 (s, 1H, CONH), 10.33 (s, 1H, NH), 9.05 (s, 1H, H5 or H2), 9.03 (s, 1H, H2 or H5), 8.66 (s, 1H, H8), 8.18 (br s, 1H, H-2'), 7.89 (br d, J=7.6 Hz, 1H, H-6'). 7.40–7.33 (m, 2H, H-4', 5'), 6.70 (dd, J=17.0, 10.2 Hz, 1H, CH$_2$CHCO), 6.41 (dd, J=1.2, 16.9 Hz, 1H, CH$_2$CHCO), 5.87 (dd, J=1.2, 10.1 Hz, 1H, CH$_2$CHCO).

$^{13}$C NMR: δ 163.35, 156.82, 154.13, 150.87, 147.92, 141.64, 140.40, 131.25, 130.26, 127.86, 126.49, 124.76, 121.30, 121.02, 120.97, 103.43.

Analysis calculated C$_{16}$H$_{12}$BrN$_5$O.1.25 H$_2$O requires: C, 51.3; H, 3.4; N, 18.7%. Found: C, 51.1; H, 3.1; N, 18.4%.

EXAMPLE 37

N-[4-(3-Methyl-phenylamino)-pyrido[3,4-d]pyrimidin-6-yl]acrylamide

To a stirred solution of 6-amino-4-[(3-methylphenyl) amino]pyrido[3,4-d]pyrimidine, made from m-toluidine and 4-chloro-6-fluoropyrido[3,4-d]pyrimidine, followed by p-methoxybenzylamine and trifluoroacetic acid, as described in the previous example (140 mg, 0.56 mmol), DMAP (14 mg) and Et$_3$N (excess, 0.5 mL) at 0° C. under N$_2$ was added acryloyl chloride (2.7 mol eq., 123 μL) dropwise over 3 hours. The reaction was then stirred at 20° C. for 1 hour, diluted with water and extracted with EtOAc. The combined organic extracts were washed with brine, dried over anhydrous Na$_2$SO$_4$ and concentrated under reduced pressure before being chromatographed on silica gel eluting with CH$_2$Cl$_2$/EtOAc (1:1) to MeOH/CH$_2$Cl$_2$/EtOAc (2:48:50), to give N-[4-[(3-methylphenyl)amino]pyrido[3,4-d]pyrimidin-6-yl]acrylamide (41 mg, 24%) as a cream powder, mp (EtOAc/hexane) 221–223° C. (decomp).

$^1$H NMR [(CD$_3$)$_2$SO]: δ 11.03 (s, 1H, CONH), 10.18 (s, 1H, NH), 9.02 (s, 1H, H5 or H2), 9.01 (s, 1H, H2 or H5), 8.59 (s, 1H, H8), 7.63 (m, 2H, H-2', 6'), 7.29 (m, 1H, H-5'), 6.89 (br d, J=7.5 Hz, 1H, H-4'), 6.69 (dd, J=17.0, 10.2 Hz, 1H, CH$_2$CHCO), 6.37 (dd, J=17.0, 1.9 Hz, 1H, CH$_2$CHCO), 5.85 (dd, J=10.2, 1.9 Hz, 1H, CH$_2$CHCO), 2.35 (s, 3H, CH$_3$Ar).

Analysis calculated for C$_{17}$H$_{15}$N$_5$O requires: C, 66.9; H, 5.0; N, 22.9%. Found: C, 67.3; H, 5.2; N, 22.9%.

EXAMPLE 38

N-[4-(3-Bromo-phenylamino)-pyrido[3,4-d]pyrimidin-6-yl]-N-methyl acrylamide 1-(3-Dimethylaminopropyl)-3-ethylcarbodiimide hydrochloride (294 mg, 1.5 mmol) was added in one portion to a solution of 4-[3-bromophenyl)amino]-6-methylaminopyrido[3,4-d]pyrimidine (100 mg, 0.3 mmol), redistilled acrylic acid (75 μL, 1.05 mmol), pyridine, (0.3 mL) in 3:2 THF:DMA (1.8 mL) stirred under N$_2$ at 0° C. After 30 minutes the reaction was warmed to 25° C., and after 3.75 hours, further acrylic acid (25 μL) was added, and the solution was stirred for an additional 3 hours. The solution was quenched with water, and the solids were collected and air dried. The solids were triturated in hot dichloromethane:ethyl acetate and collected to leave the product (67 mg, 56%), mp 215–223° C. (dec).

$^1$H NMR [(CD$_3$)$_2$SO]: δ 10.11 (s, 1H, exchanges D$_2$O), 9.14 (s, 1 H), 8.80 (s, 1H), 8.45 (s, 1H), 8.22 (s, 1H), 7.91 (br d, J=7.7 Hz, 1H), 7.43–7.36 (m, 2H), 6.36–6.23 (m, 2H), 5.66 (dd, J=9.5, 3.0 Hz, 1 H), 3.44 (s, 3H).

CIMS m/z (relative %) 383 (23), 384 (100), 385 (40), 386 (99), 387 (20).

Analysis calculated for C$_{17}$H$_{14}$N$_5$OBr 0.4 H$_2$O: C, 52.16; H, 3.81; N, 17.89. Found: C, 52.25; H, 3.51; N, 17.76.

EXAMPLE 39

N-[4-(3-Bromo-phenylamino)-pyrido[3,4-d]pyrimidin-6-yl]-methacrylamide

To a solution of 6-amino-4-[(3-bromophenyl)amino] pyrido[3,4-d]pyrimidine (J Med Chem, 1996;39:1823) (250 mg, 0.82 mmol), Et$_3$N (excess, 2.0 mL) and DMAP (catalytic) in THF (30 mL) under nitrogen was added methacryloyl chloride (3×1.1 mol eq., total of 264 μL), the reaction conditions and work up were followed as above to give after column and preparative layer chromatography on silica gel eluting with EtOAc/CH$_2$Cl$_2$ (1:1), N-[4-[(3-bromophenyl)amino]pyrido-[3,4-d]pyrimidin-6-yl]-2-methylacrylamide (18 mg, 6%) as a cream powder, mp (CH$_2$Cl$_2$/hexane) 177–178° C.

$^1$H NMR [(CD$_3$)$_2$SO]: δ 10.61 (s, 1H, CONH), 10.29 (s, 1H, NH), 9.06 (s, 1H, H5), 8.93 (s, 1H, H2), 8.67 (s, 1H, H8), 8.19 (t, J=1.6 Hz, 1H, H-2'), 7.91 (dt, J$_d$=7.6 Hz, J$_t$=1.6 Hz, 1H, H-6'), 7.38 (t, J=7.9 Hz, 1H, H-5'), 7.34 (dt, J$_d$=8.1 Hz, J$_t$= 1.4 Hz, 1H, H-4'), 6.04 (s, 1H, CH$_2$C(CH$_3$)CO), 5.64 (s, 1H, CH$_2$C(CH$_3$)CO), 2.03 (s, 1H, CH$_2$C(CH$_3$)CO).

EI HRMS (M$^+$) C$_{17}$H$_{14}$Br$^{81}$N$_5$O requires 385.0361. Found 385.0360.

EXAMPLE 40

N-[4-(3-Bromo-phenylamino)-pyrido[3,4-d] pyrimidin-6-yl]-ethenylsulfonamide

A solution of 6-amino-4-[(3-bromophenyl)amino]pyrido [3,4-d]pyrimidine (*J Med Chem*, 1996;39:1823) (250 mg, 0.82 mmol), Et$_3$N (0.23 mL) and DMAP (catalytic) in THF (20 mL) was reacted with chloro-ethanesulfonyl chloride (1.4 mol eq., 1.15 mmol, 120 μL) as above to give after chromatography on silica gel eluting with MeOH/CH$_2$Cl$_2$/EtOAc (2:48:50) and crystallization from CH$_2$Cl$_2$/hexane, N-[4-[(3-bromophenyl)amino]pyrido[3,4-d]pyrimidin-6-yl]-vinylsulfonamide (53 mg, 16%) as a cream powder, mp 261–265° C.

$^1$H NMR [(CD$_3$)$_2$SO]: δ 11.02 (s, 1H, SO$_2$NH), 10.25 (s, 1H, NH), 9.02 (s, 1H, H5), 8.67 (s, 1H, H2), 8.15 (br s, 1H, H-2'), 8.00 (s, 1H, H8), 7.87 (dt, J$_d$=7.2 Hz, J$_t$=1.9 Hz, 1H, H-6'), 7.40 (br t, J=7.9 Hz, 1H, H-5'), 7.37 (br dt, J$_d$=7.8 Hz, J$_t$=1.9 Hz, 1H, H-4'), 7.07 (dd, J=16.5, 9.9 Hz, 1H, CH$_2$CHSO$_2$), 6.30 (d, J=16.5 Hz, 1H, CH$_2$CHSO$_2$), 6.09 (d, J=9.9 Hz, 1H, CH$_2$CHSO$_2$).

$^{13}$C NMR: δ 156.59, 154.34, 151.23, 147.43, 141.54, 140.18, 137.02, 130.36, 127.06, 126.73, 124.88, 121.43, 121.24, 121.07, 103.57.

Analysis calculated for C$_{15}$H$_{12}$BrN$_5$O$_2$S.0.25 H$_2$O requires: C, 43.9; H, 3.1; N, 17.0%. Found: C, 44.2; H, 3.0; N, 16.5%.

EXAMPLE 41

N-[4-(3-Bromo-phenylamino)-pyrido[3,4-d] pyrimidin-6-yl]-acrylamide

To a stirred solution of 6-amino-4-[(3-bromophenyl) amino]pyrido[3,2-d]pyrimidine (*J Med Chem*, 1996;39:1823) (46 mg, 0.15 mmol) and acrylic acid (6 mol eq., 0.91 mmol, 62 μL) in DMA (5.0 mL) under N$_2$ was added 1-(3-dimethylaminopropyl)-3-ethylcarbodiimide hydrochloride (EDCI.HCl) (4.0 mol eq., 0.61 mmol, 116 mg). The reaction mixture was stirred for 48 hours with additional amounts of acrylic acid and EDCI.HCl (62 μL/116 mg) being added every 12 hours it was then worked up as above to give after chromatography on silica gel eluting with EtOAc:CH$_2$Cl$_2$ (1:1) to MeOH/CH$_2$Cl$_2$/EtOAc (2:48:50), N-[4-[(3-bromophenyl)amino]pyrido[3,2-d] pyrimidin-6-yl]acrylamide (14 mg, 26%) as a cream powder, mp (CH$_2$Cl$_2$/hexane) 226–228° C.

$^1$H NMR [(CD$_3$)$_2$SO]: δ 11.13 (s, 1H, CONH), 9.57 (s, 1H, NH), 8.72 (s, 1H, H2), 8.69 (d, J=9.1 Hz, 1H, H8), 8.43 (t, J=1.9 Hz, 1H, H-2'), 8.30 (d, J=9.1 Hz, 1H, H7), 7.87 (br d, J=6.9 Hz, 1H, H-6'), 7.39 (t, J=8.1 Hz, 1H, H-5'), 7.33 (dt, J$_d$=8.2 Hz, J$_t$=1.3 Hz, 1H, H-4'), 6.68 (dd, J=17.0, 10.2 Hz, 1H, CH$_2$CHCO), 6.43 (dd, J=17.0, 1.8 Hz, 1H, CH$_2$CHCO), 5.91 (dd, J=10.2, 1.8 Hz, 1H, CH$_2$CHCO).

Analysis calculated for C$_{16}$H$_{12}$BrN$_5$O requires: C, 51.9; H, 3.3; N, 18.9%. Found: C, 51.7; H, 3.3; N, 18.8%.

EXAMPLE 42

N-[4-(3-Bromo-phenylamino)-benzo[b]thieno[3,2-d] pyrimidin-8-yl]acrylamide

To a solution of 8-amino-4-[(3-bromophenyl)amino] benzothieno-pyrimidine [see Patent Application WO 95/19970 1995] (100 mg, 0.26 mmol), acrylic acid (0.04 mL, 0.58 mmol), and triethylamine (0.07 mL, 0.5 mmol) in DMF (1.5 mL) stirred under N$_2$ at 25° C. was added 1-(3-dimethylaminopropyl)-3-ethylcarbodiimide hydrochloride (127 mg, 0.66 mmol). After 24 hours the reaction mixture was quenched with water and the light tan precipitate was collected by Buchner filtration and purified by preparative tlc on silica, eluting with 10% MeOH/CHCl$_3$ to give the desired product (25 mg, 23%) as a tan solid, mp 249.0–250.5° C.

$^1$H NMR [(CD$_3$)$_2$SO]: δ 10.50 (s, 1H, NH), 9.86 (s, 1H, NH), 8.86 (d, J=2.0 Hz, 1H, H9), 8.79 (s, 1H, H2), 8.19 (s, 1H, H2'), 8.17 (dd, J=8.0, 1.9 Hz, 1H, H7), 7.91 (dd, J=8.8, 2.2 Hz, 1H, H6), 7.84 (d, J=8.1 Hz, 1H, H6'), 7.35 (t, J=8.1 Hz, 1H, H5'), 7.29 (d, J=8.0 Hz, 1H, H4'), 6.50 (dd, J=16.9, 10 Hz, 1H, =CH), 6.33 (dd, J=16.8, 2.1 Hz, 1H, =CH$_2$), 5.82 (dd, J=10, 1.9 Hz, 1H, =CH$_2$).

Mass Spectrum (APCI): 427 (100, $^{81}$BrMH$^+$), 426 (21, $^{81}$BrM$^+$), 425 (93, $^{79}$BrMH$^+$).

Calculated for C$_{19}$H$_{13}$N$_4$BrOS.0.3HCl.0.25C$_3$H$_6$O: C, 52.49; H, 3.18; N. 12.19%. Found: C, 52.62; H, 3.31; N, 12.40%.

EXAMPLE 43

N-[4-(3-Bromo-phenylamino)-benzo[b]thieno[3,2-d] pyrimidin-6-yl]acrylamide

6-Amino-4-(3-bromoaniline)benzothieno[3,2-d] pyrimidine

2-Chloro-3-nitrobenzamide: DMF (3 drops) was added to a mixture of 2-chloro-3-nitrobezoic acid (0.99 g, 4.9 mmol), oxalyl chloride (0.47 mL, 5.4 mmol) in CH$_2$Cl$_2$ (20 mL) at 25° C. stirring under N$_2$. After gas formation ceased, all the solid went into solution. After 3 hours the solvent was removed under reduced pressure to leave a light yellow solid which was treated with cold NH$_4$OH (20 mL). 2-Chloro-3-nitrobenzamide was collected as an off-white solid (1.02 g, 100%).

$^1$H NMR [(CD$_3$)$_2$SO]: δ 8.12 (brs, 1H, NH2), 8.06 (dd, J=8.0, 1.7 Hz, 1H, H4), 7.87 (brs, 1H, NH2), 7.73 (dd, J=7.8, 1.7 Hz, 1H, H6), 7.63 (t, J=8.1 Hz, 1H, H5).

2-Chloro-3-nitrobenzonitrile: A solution of 2-chloro-3-nitrobenzamide (1.02 g, 4.9 mmol) in P$_2$O$_5$/(TMS)$_2$O/1,2-dichloroethane (30 mL) was heated at 85° C. for 18 hours. After it was cooled to 25° C., the solution was filtered through a plug of silica gel (60 mL), eluting with 5% methanol/CHCl$_3$ (400 mL). The combined washes were concentrated under reduced pressure to give 2-chloro-3-nitrobenzonitrile as an off-white solid (0.66 g, 74%).

$^1$H NMR [(CD$_3$)$_2$SO]: δ 8.42 (dd, J=8.1, 1.5 Hz, 1H, H4), 8.33 (dd, J=8.1, 1.7 Hz, 1H, H6), 7.81 (t, J=8.3 Hz, 1H, H5).

3-Amino-2-methylcarboxylate-7-nitrobenzothiophene: NEt$_3$ (0.16 mL, 1.15 mmol) was added dropwise to a solution of 2-chloro-3-nitrobenzonitrile (191 mg, 1.05 mmol), and methyl thioacetate (0.1 mL, 1.1 mmol) in DMSO (3 mL) at 25° C. stirring under $N_2$. The color of the solution turned dark orange. Thirty minutes later the reaction was quenched with ice water. The formed solid was collected by Buchner filtration and air dried to give methyl 3-amino-7-nitrobenzothiophene-2-carboxylate as a red-orange solid (244 mg, 92%).

$^1$H NMR [$(CD_3)_2SO$]: δ 8.67 (dd, J=8.1, 1.0 Hz, 1H, H6), 8.58 (dd, J=7.8, 0.8 Hz, 1H, H4), 7.72 (t, J=7.8 Hz, 1H, H5), 7.37 (brs, 2H, NH2).

6-Nitrobenzothieno[3,2-d]pyrimidone: A mixture of methyl 3-amino-7-nitrobenzothiophene-2-carboxylate (242 mg, 0.96 mmol) and formamidine acetate (0.51 g, 4.9 mmol) was heated up to 185° C. when 1.5 mL formamide was added to the reaction. After 1 hour at 185° C., the reaction was cooled to 25° C. The solid was collected and washed with water then dried. 6-Nitrobenzothieno [3,2-d] pyrimidone was isolated as a yellow solid (161.5 mg, 68%).

$^1$H NMR [$(CD_3)_2SO$]: δ 8.72 (d, J=8.1 Hz, 2H, H7, H9), 8.45 (s, 1H, H2), 7.91 (t, J=7.8 Hz, H8).

4-Chloro-6-nitrobenzothieno[3,2-d]pyrimidine: Dry DMF (5 drops) was added to a mixture of 6-nitrobenzothieno[3,2-d]pyrimidone (161 mg, 0.65 mmol) and oxalyl chloride (0.28 mL, 3.2 mmol) in 1,2-dichloroethane (5 mL). The reaction was heated at 85° C. for 7.5 hours then cooled to 25° C. The solid was Buchner filtered and washed with $CH_2Cl_2$ and air dried. 4-Chloro-6-nitrobenzothieno[3,2-d]pyrimidine was obtained as a gray solid (166 mg, 96% crude).

$^1$H NMR [$(CD_3)_2SO$]: δ 9.33 (s, 1H, H2), 8.99 (dd, J=7.9, 1.3 Hz, 1H, H7), 8.87 (dd, J=8.1, 1.0 Hz, 1H, H9), 8.03 (t, J=7.8 Hz, 1H, H8).

4-([3-Bromophenyl]amino)-6-nitrobenzothieno [3,2-d] pyrimidine: A mixture of 4-chloro-6-nitrobenzothienopyrimidine (166 mg, 0.62 mmol), m-bromoaniline (0.08 mL, 0.73 mmol) and m-bromoaniline hydrochloride (144 mg, 0.69 mmol) in isopropanol (4.5 mL) was heated at 85° C. stirring under $N_2$ for 7.5 hours. The dark brown solid was collected by Buchner filtration and washed with isopropanol and air dried to give 4-([3-bromophenyl]amino)-6-nitrobenzothieno[3,2-d]pyrimidine (145 mg, 67%), mp 247.0–248.1° C.

$^1$H NMR [$(CD_3)_2SO$]: δ 10.21 (s, 1H, NH), 8.89 (s, 1H, H2), 8.84 (dd, J=7.6, 1.1 Hz, 1H, H7), 8.75 (dd, J=8.0, 0.9 Hz, 1H, H9), 8.25 (s, 1H, H2'), 7.92 (t, J=7.8 Hz, 1H, H8), 7.89 (d, J=6.6 Hz, 1H, H4'), 7.39–7.31 (m, 2H, H5', H6').

MS (APCI): 403 (100, $^{81}$Br, MH$^+$), 402 (17.45, $^{81}$Br, M$^+$), 401 (93.01, $^{79}$Br, MH$^+$).

Calculated for $C_{16}H_9BrN_4O_2S \cdot HCl$: C, 43.90; H, 2.30; N, 12.80%. Found: C, 44.00; H, 2.43; N, 12.48%.

6-Amino-4-([3-bromophenyl]amino)benzothieno [3,2-d] pyrimidine: A solution of 4-([3-bromophenyl]amino)-6-nitrobenzothieno[3,2-d]pyrimidine (160 mg, 0.4 mmol) in methanol (10 mL) was subjected to hydrogenation with Raney Nickel (0.07 g) at 25° C. for 30 hours. After the reaction was done, the solvent was removed under reduced pressure to leave a dark brown solid. Recrystalization from wet methanol afforded 6-amino-4-([3-bromophenyl]amino) benzothieno[3,2-d]pyrimidine as a brown solid (70 mg, 43%), mp 217.6–218.8° C.

$^1$H NMR [$(CD_3)_2SO$]: δ 9.89 (s, 1H, NH), 8.77 (s, 1H, H2), 8.19 (t, J=1.9 Hz, H2'), 7.85 (ddd, J=8.1, 2.9, 1.2 Hz, 1H, H4'), 7.64 (dd, J=7.9, 1.0 Hz, 1H, H9), 7.34 (t, J=7.6 Hz, 2H, H8, H5'), 7.28 (td, J=8.1, 1.5 Hz, 1H, H6'), 6.95 (dd, J=7.4, 1.0 Hz, 1H, H7), 5.71 (brs, 2H, NH2).

MS (APCI): 373 (100, $^{81}$Br, MH$^+$), 372 (19.5, $^{81}$Br, M$^+$), 371 (96.87, $^{79}$Br, MH$^+$).

Calculated for $C_{16}H_{11}BrN_4S \cdot 0.3HCl \cdot 0.7\ CH_3OH$: C, 49.57; H, 3.51; N, 13.85%. Found: C, 49.47; H. 3.56; N. 13.84%.

To a solution of 6-amino-4-[(3-bromophenyl)amino] benzothieno-quinazoline (130 mg, 0.35 mmol), acrylic acid (0.05 mL, 0.73 mmol), and triethylamine (0.1 mL, 0.72 mmol) in DMF (3 mL) stirred under $N_2$ at 0° C. was added 1-(3-dimethylaminopropyl)-3-ethylcarbodiimide hydrochloride (144 mg, 0.75 mmol). The reaction gradually warmed up to 25° C. and was quenched with water after 20 hours. The formed yellow solid was collected and purified by sonication with acetone to give the desired product (40 mg, 27%), mp 216.4–217.2° C.

$^1$H NMR [$(CD_3)_2SO$]: δ 10.64 (s, 1H, NH), 9.84(s, 1H, NH), 8.77 (s, 1H, H2), 8.73 (d, J=1.5 Hz, 1H, H6), 8.31 (d, 1H, J=8.8 Hz, H8), 8.20 (s, 1H, H2'), 7.84 (d, J=8.3 Hz, 1H, H6'), 7.67 (dd, J=8.6, 1.7 Hz, 1H, H9), 7.34 (t, J=7.8 Hz, 1H, H5'), 7.28 (d, J=8.1 Hz, 1H, H4'), 6.50 (dd, J=16.9, 10.0 Hz, 1H, =CH), 6.34 (dd, J=17.1, 1.7 Hz, 1H, =$CH_2$), 5.83 (dd, J=10, 1.7 Hz, 1H =$CH_2$).

Mass Spectrum (APCI): 426.7 (100, $^{81}$BrMH$^+$), 425.7 (26.28, $^{81}$BrM$^+$), 424.7 (92, $^{79}$BrMH$^+$).

Calculated for $C_{19}H_{13}N_4BrOS \cdot 0.3HCl \cdot 0.8H_2O$: C, 52.28; H, 3.62; N, 12.26%. Found: C, 52.42; H, 3.49; N, 12.41%.

EXAMPLE 44

N-[4-(3-Bromo-phenylamino)-benzo[b]thieno[3,2-d] pyrimidin-7-yl]acrylamide

7-Nitrobenzo[b]thieno[3,2-d]-3H-pyrimid-4-one

2-Fluoro-4-nitrobenzoic acid: [25] To a solution of sodium dichromate (3.87 g, 13 mmol) in acetic acid (20 mL) was added 2-fluoro-4-nitrotoluene (1.55 g, 10 mmol) in portions, followed by dropwise addition of concentrated sulfuric acid (10 g). A strong exotherm was observed (100° C.) and the color changed from orange to green. The reaction was heated at 90° C. for 1 hour and cooled to 25° C. The reaction mixture was dissolved in water (30 ml) and white crystals formed upon cooling at 0° C. The white solid was collected by filtration washed with cold water and dried to give 2-fluoro4-nitrobenzoic acid (0.99 g, 53%).

$^1$H NMR (DMSO-$d_6$) δ: 8.16 (dd, J=10.0, 2.0 Hz, 1H), 8.10–8.03 (m, 2H).

2-Fluoro-4-nitrobenzamide: To a mixture of 2-fluoro-4-nitrobenzoic acid (0.98 g, 5.3 mmol) and oxalyl chloride (0.48 mL, 5.5 mmol) in dichloromethane (25 mL), stirred under nitrogen at 25° C., was added 3 drops of dimethyl formamide. Gas evolution! The solid slowly dissolved up and after 4 hours the volatiles were removed under reduced pressure. Saturated aqueous ammonia (5 mL) was added to the residue and the mixture was stirred for 10 minutes. The solid was extracted with chloroform (3×20 mL). The combined organic layer was washed with water, saturated brine, and dried (magnesium sulfate). The solvent was removed under reduced pressure to give 2-fluoro-4-nitrobenzamide (0.83 g, 85%) as a light yellow solid.

$^1$H NMR (DMSO-$d_6$): δ 8.15 (dd. J=10.0, 2.2 Hz, 1H), 8.06 (dd, J=8.5, 2.2 Hz, 1H), 8.02 (brs, 1H), 7.88 (brs, 1H), 7.81 (dd, J=8.3, 7.0 Hz, 1H). 2-Fluoro-4-nitrobenzonitrile: A mixture of 2-fluoro-4-nitrobenzamide (0.83 g, 4.6 mmol) and phosphorus pentoxide/hexamethyl disiloxane in 1,2-dichloroethane (20 mL) was heated under nitrogen at 100° C. for 4 hours. Upon cooling, the solution was poured onto a plug of silica gel and washed with hexane (200 mL) followed by 5% methanol/chloroform (400 mL). The methanol/chloroform washes were collected and concentrated under reduced pressure to give 2-fluoro-4-nitrobenzonitrile (0.71 g, 95%) as a beige solid.

$^1$H NMR (DMSO-$d_6$): δ 8.46 (dd, J=9.5, 2.0 Hz, 1H), 8.37–8.22 (m, 2H).

Methyl 3-amino-6-nitrobenzothiophene-2-carboxylate: Methyl thioglycollate (0.08 mL, 0.85 mmol) was added to a solution of 2-fluoro-4-nitrobenzonitrile (145 mg, 0.87 mmol), and triethylamine (0.14 mL, 1.0 mmol) in acetonitrile (20 mL) stirred under nitrogen at 25° C. After 3 hours further triethylamine (0.28 mL, 2.0 mmol) was added to the solution, which was stirred at 25° C. for a further 16 hours. The solvent was removed under reduced pressure to give a brown residue, which upon trituration with chloroform precipitated methyl 3-amino-6-nitrobenzothiophene-2-carboxylate (103 mg, 54%) as a red brown solid, mp 228.5–229.5° C.

$^1$H NMR (DMSO-$d_6$): δ 8.87 (d, J=2.0 Hz, 1H), 8.32 (d, J=9.0 Hz, 1H), 8.15 (dd, J=8.8, 2.0 Hz, 1H), 7.26 (brs, 2H), 3.77 (s, 3H).

Mass Spectrum (CI): 253 (100, MH$^+$), 252 (52, M$^+$).

7-Nitrobenzo[b]thieno[3,2-d]-3H-pyrimid-4-one: A mixture of methyl 3-amino-6-nitrobenzothiophene-2-carboxylate (20 mg, 0.08 mmol) and formamidine acetate (59 mg, 0.57 mmol) was heated at 190° C. for 5 hours and cooled to 25° C. The reaction residue was triturated with water, and 7-nitrobenzo[b]thieno[3,2-d]-3H-pyrimid-4-one (7 mg, 36%) was obtained by Buchner filtration as a dark brown solid, mp >320° C.

$^1$H NMR (DMSO-$d_6$): δ 9.21 (d, J=1.7 Hz, 1H), 8.39 (d, J=8.5 Hz, 1H), 8.38 (s, 1H), 8.32 (dd, J 8.8, 2.0 Hz, 1H).

Mass Spectrum (CI): 248 (100, MH$^+$), 247 (30, M$^+$).

Analysis calculated for $C_1OH_5N_3O_3S$: C, 48.58; H, 2.04; N, 17.00%. Found: C, 48.19; H, 2.09; N, 16.77%.

To a solution of 7-amino-4-[(3-bromophenyl)amino] benzothieno-pyrimidine (88 mg, 0.24 mmol), acrylic acid (0.03 mL, 0.44 mmol), and triethylamine (0.09 mL, 0.64 mmol) in DMF (3 mL), stirred under nitrogen at 0° C., was added 1-(3-dimethylaminopropyl)-3-ethylcarbodiimide hydrochloride (84 mg, 0.44 mmol). The reaction gradually warmed up to 25° C. and was quenched with water after 24 hours. The light brown precipitate was collected and purified by sonication with acetone. The desired product was isolated as a beige solid (59 mg, 37%), mp 251.0–252.4° C.

$^1$H NMR [(CD$_3$)$_2$SO]: δ 10.58 (s, 1H, NH), 9.92 (s, 1H, NH), 8.84 (s, 1H, H2), 8.28–8.24 (m, 2H, H6, H2'), 7.88 (d, 1H, J=6.8 Hz, H6'), 7.70 (dd, J=7.6, 1.2 Hz, 1H, H8), 7.65 (t, J=7.6 Hz, 1H, H9), 7.33 (t, J=8.0 Hz, 1H, H5'), 7.28 (dd, J=6.9, 1.8 Hz, 1H, H4'), 6.60 (dd, J=16.8, 10.0 Hz, 1H, =CH), 6.36 (dd, J=17.1, 1.9 Hz, 1H, =CH$_2$), 5.88 (dd, J=10.3, 1.7 Hz, 1H, =CH$_2$).

Mass Spectrum (APCI): 426.7 (100, MH$^+$), 425.7 (18.68, M$^+$).

Calculated for $C_{19}H_{13}N_4BrOS·H_2O$: C, 51.47; H, 3.41; N, 12.64%. Found: C, 51.42; H, 3.39; N, 12.40%.

EXAMPLE 45

N-[4-(3-Bromophenyl)amino]quinazolin-6-yl]buta-2,3-dienamide

To a solution of 6-amino-4-[(3-bromophenyl)amino] quinazoline (316 mg, 1.0 mmol), and 3-butynoic acid (173 mg, 2.06 mmol) in DMF (5 mL) stirred under nitrogen at 0° C. was added 1-(3-dimethylaminopropyl)-3-ethylcarbodiimide hydrochloride (384 mg, 2.0 mmol). After 1.5 hours the reaction was quenched with 0.1 M HCl solution (10 mL). The yellow precipitate was collected by Buchner filtration and washed with water followed by acetone. The solid was taken up into acetone with the addition of triethylamine. The formed solution was filtered through a 2-inch silica gel eluting with 50% acetone/CH$_2$Cl$_2$. The filtrate was collected and concentrated under reduced pressure to give the title compound as a yellow solid (247 mg, 56%), mp 268–270° C.

$^1$H NMR [(CD$_3$)$_2$SO]: δ 10.39 (s, 1H, NH), 9.93 (s, 1H, NH), 8.76 (d, J=2.2 Hz, 1H, H5), 8.58 (s, 1H, H2), 8.18 (s, 1H, H2'), 7.87 (dt, J=9.0, 1.9 Hz, 2H, H7, H8), 7.79 (d, J=8.8 Hz, 1H, H6'), 7.34 (t, J=7.9 Hz, 1H, H5'), 7.29 (d, J=8.3 Hz, 1H, H4'), 6.07 (t, J=6.5 Hz, 1H, CH=C=CH$_2$), 5.49 (d, J=6.6 Hz, 2H, =C=CH$_2$).

Mass Spectrum (APCI): 382.8 (88, $^{81}$BrMH$^+$), 381.8 (19, $^{81}$BrM$^+$), 380.7 (100, $^{79}$BrMH$^+$).

Calculated for $C_{18}H_{13}N_4BrO·0.8H_2O·0.8C_3H_6O$: C, 55.42; H. 4.42; N, 12.68%. Found: C, 55.13; H, 4.17; N, 12.87%.

EXAMPLE 46

N-[4-[(3-Bromophenyl)amino]quinazolin-6-yl]-E,4-oxopent-2-enamide

6-Amino-4-[(3-bromophenyl)amino]quinazoline (0.23 g, 0.75 mmol) and N-ethyl diisopropylamine (0.26 mL, 1.5 mmol) were added to a solution of E,4-oxopent-2-enoic acid (171 mg, 1.5 mmol) and EDAC.HCl (288 mg, 1.5 mmol) in THF/DMF (3:1, 4 mL) stirred under N$_2$ at 25° C. The ice bath was removed, and the reaction mixture was stirred at 25° C. for 4 hours, when further N-ethyl diisopropylamine (0.13 mL, 0.75 mmol), E,4-oxopent-2-enoic acid (86 mg, 0.75 mmol) and EDAC.HCl (144 mg, 0.75 mmol) were added. After stirring a further 14 hours at 25° C., the reaction mixture was added dropwise to stirred cold water (100 mL). The solid was collected, dissolved in MeOH (50 mL) and dried onto silica gel (3 g). This was used as the origin in a silica gel flash column (80 g) eluting with 10% MeOH/CH$_2$Cl$_2$. Concentration of pure fractions under reduced pressure gave N-[4–1(3-bromophenyl)amino)quinazolin-6-yl]-E,4-oxopent-2-enamide (0.14 g, 45%) as a yellow solid, mp 230° C. (decomp.).

$^1$H NMR [(CD$_3$)$_2$SO]: δ 10.91 (s, 1H, NH), 9.99 (s, 1H, NH), 8.87 (d, J=1.9 Hz, 1H, H5), 8.60 (s, 1H, H2), 8.17 (t, J=1.9 Hz, 1H, H2'), 7.85 (m, 3H, H7, H8, H6'), 7.37 (m, 2H, H5', H4'), 7.15 (d, J=15.7 Hz, 1H, H3-pentenyl), 6.99 (d, J=15.7 Hz, 1H, H2-pentenyl), 2.40 (s, 3H, Me).

Mass Spectrum (APCI): 412.7 (100, $^{81}$BrMH$^+$), 410.8 (98, $^{79}$BrMH$^+$).

Calculated for $C_{19}H_5BrN_4O_2$: C, 55.49; H, 3.68; N, 13.62%. Found: C, 55.21; H, 3.72; N, 13.35%.

EXAMPLE 47

N-[4-[(3-Bromophenyl)amino]quinazolin-6-yl]-E,4-ethoxy-4-oxobut-2-enamide

6-Amino-4-[(3-bromophenyl)amino)quinazoline (0.23 g, 0.75 mmol) and N-ethyl diisopropylamine (0.26 mL, 1.5 mmol) were added to a solution of E,4-ethoxy-4-oxobut-2-enoic acid (216 mg, 1.5 mmol) and EDAC.HCl (288 mg, 1.5 mmol) in THF/DMF (3:1, 4 mL) stirred under N$_2$ at 25° C. The ice bath was removed, and the reaction mixture was stirred at 25° C. for 4 hours, when further N-ethyl diisopropylamine (0.13 mL, 0.75 mmol), E,4-ethoxy-4-oxobut-2-enoic acid (108 mg, 0.75 mmol), and EDAC.HCl (144 mg, 0.75 mmol) were added. After stirring a further 14 hours at 25° C., the reaction mixture was added dropwise to stirred cold water (100 mL). The solid was collected, dissolved in MeOH (50 mL), and dried onto silica gel (3 g). This was used as the origin in a silica gel flash column (80 g) eluting with 10% MeOH/CH$_2$Cl$_2$. Concentration of pure fractions under reduced pressure gave N-[4-[(3-bromophenyl)amino] quinazolin-6-yl]-E,4-ethoxy-4-oxobut 2-enamide (0.19 g, 58%) as a yellow solid, mp >255° C.

$^1$H NMR [(CD$_3$)$_2$SO]: δ 10.93 (s, 1H, NH), 9.99 (s, 1H, NH), 8.89 (d, J=1.9 Hz, 1H, H5), 8.60 (s, 1H, H2), 8.16 (t, J=1.9 Hz, 1H, H2'), 7.85 (m, 3H, H7, H8, H6'), 7.33 (m, 3H, H5', H4', H3-pentenyl), 6.79 (d, J=15.4 Hz, 1H, H2-pentenyl), 4.24 (q, J=7.1 Hz, CH$_2$), 1.29 (t, J=7.1 Hz, 3H, Me).

Mass Spectrum (APCI): 442.8 (99, $^{81}$BrMH$^+$), 440.8 (100, $^{79}$BrMH$^+$).

Calculated for C$_{20}$H$_{17}$BrN$_4$O$_3$: C, 54.44; H, 3.88; N, 12.70%. Found: C, 54.59; H, 3.83; N, 12.67%.

EXAMPLE 48

N-[4-(3-Bromo-phenylamino)-pyrido[3,4-d] pyrimidin-6-yl]penta-2,4-dienamide

To a 0–5° C. solution of 6-amino-4-[(3-bromophenyl) amino]pyrido[3,4-d]pyrimidine (160 mg, 0.5 mmol), 80% trans-2,4-pentadienoic acid (245 mg, 2 mmol), and pyridine, (0.5 mL) in 2:1 THF:DMA (3 mL) stirred under N$_2$ was added in one portion 1-(3-dimethylaminopropyl)-3-ethylcarbodiimide hydrochloride (490 mg, 2.5 mmol). Cooling was removed, and the viscous mixture was stirred at 25° C. After 23 hours, the mixture was charged with additional trans-2,4-pentadienoic acid (125 mg), 1-(3-dimethylaminopropyl)-3-ethylcarbodiimide hydrochloride (240 mg), and 2:1 THF:DMA (2 mL). After stirring for another 19 hours, the mixture was diluted with water and ethyl acetate. The biphasic mixture was warmed, then filtered through celite with the filter pad washed well with water and hot ethyl acetate. The filtrate was extracted with ethyl acetate (3×), and the combined organic phases were washed with brine, dried (MgSO$_4$), and concentrated to a solid. The solid was dissolved in hot ethyl acetate and the solution purified by column chromatography over flash SiO$_2$ eluting with ethyl acetate. Product fractions were pooled and concentrated to a solid that was triturated in warm ethyl acetate. After cooling, the solids were collected and dried to leave the product (27 mg, 13%), mp 210–215° C.

$^1$H NMR [(CD$_3$)$_2$SO]: δ 11.04 (s, 1H, exchanges D$_2$O), 10.34 (s, 1H, exchanges D$_2$O), 9.04 (s, 1H), 9.02 (s, 1H), 8.66 (s, 1H), 8.17 (t, J=1.9 Hz, 1H), 7.89 (dt, J=7.7, 1.7 Hz, 1H), 7.40–7.27 (m, 3H), 6.60 (dt, J=16.9, 10.6 Hz, 1H), 6.53 (d, J=15.2 Hz, 1H), 5.75 (d, J=16.9 Hz, 1H), 5.56 (d, J=11.1 Hz, 1H).

Mass Spectrum (APCI) m/z (relative %): 395.9 (89), 396.9 (20), 397.9 (100), 398.9 (20).

Analysis calculated for C$_{18}$H$_{14}$N$_5$OBr.0.3 H$_2$O.0.2 C$_4$H$_8$O$_2$: C, 53.86; H, 3.89; N, 16.70. Found: C, 54.02; H, 3.77; N, 16.33.

EXAMPLE 49

N-[4-(3-Bromo-phenylamino)-pyrido[3,4-d] pyrimidin-6-yl]-N-(2-(N,N-dimethylamino)ethyl) acrylamide To a 0–5° C. solution of 4-[3-bromophenyl)amino]-6-(2-dimethylaminoethyl)aminopyrido[3,4-d]pyrimidine (387 mg, 1 mmol) and redistilled acrylic acid (0.25 mL, 3.6 mmol) in pyridine (5 mL) stirred under N$_2$ was added 1-(3-dimethylaminopropyl)-3-ethylcarbodiimide hydrochloride (980 mg, 5 mmol). After 30 minutes, cooling was removed, and the solution was stirred for an additional 45 minutes. The solution was diluted with 1% aqueous sodium bicarbonate and extracted with ethyl acetate (4×). The combined extracts were washed with brine, dried (MgSO$_4$), and concentrated to leave an oil that was crystallized from ethyl acetate at 5° C. overnight to leave product (122 mg, 28%), mp >160° C. (dec).

$^1$H NMR [(CD$_3$)$_2$SO]: δ 10.16 (s, 1H, exchanges D$_2$O), 9.15 (S, 1H), 8.80 (s, 1H), 8.43 (s, 1H), 8.22 (s, 1H), 7.93 (d, J=7.7 Hz, 1H), 7.42–7.35 (m, 2H), 6.29–6.22 (m, 2H), 5.66 (dd, J=9.0, 3.5 Hz, 1 H), 4.05 (t, J=7.1 Hz, 2H) 2.42 (t, J=7.1 Hz, 2H), 2.11 (s, 6H).

Mass Spectrum (APCI) m/z (relative %): 440.9 (99), 441.8 (23), 442.8 (100), 443.9 (24).

Analysis calculated for C$_{20}$H$_{21}$N$_6$OBr: C, 54.43; H, 4.80; N, 19.04. Found: C, 54.15; H, 4.65; N, 18.76.

EXAMPLE 50

4N-[4-(3-Bromo-phenylamino)-pyrido[3,4-d] pyrimidin-6-yl]E-but-2-enamide

To a 0–5° C. solution of 6-amino-4-[(3-bromophenyl) amino]pyrido[3,4-d]pyrimidine (32 mg, 0.1 mmol), trans-crotonic acid (35 mg, 0.4 mmol), in pyridine (0.4 mL) stirred under N$_2$ was added 1-(3-dimethylaminopropyl)-3-ethylcarbodiimide hydrochloride (98 mg, 0.5 mmol). Cooling was removed and the mixture was stirred at 25° C. After 2 hours, the solution was diluted with water, and the suspension was stirred for 15 minutes. The solids were collected, then dissolved in ethyl acetate. The solution was washed with 5% aqueous sodium bicarbonate, dried (MgSO$_4$), and filtered through flash SiO$_2$. The filtrate was concentrated to a solid that was triturated in hot ethyl acetate. The solids were collected to leave product, (11 mg, 28%) mp >260° C. (dec).

$^1$H NMR [(CD$_3$)$_2$SO]: δ 10.87 (s, 1H, exchanges D$_2$O), 10.31 (s, 1H, exchanges D$_2$O), 9.03 (s, 1H), 9.00 (s, 1H), 8.65 (s, 1H), 8.17 (s,1H), 7.89 (d, J=7.5 Hz, 1H), 7.39–7.33 (m, 2H), 6.99–6.90 (m, 1H), 6.39 (dd, J=15.4, 1.7 Hz, 1H), 1.91 (dd, J=7.0, 1.4 Hz, 3H.

Mass Spectrum (APCI) m/z (relative %): 381.8 (74), 382.8 (27), 383.8 (100), 384.8 (30), 385.9 (10).

Analysis calculated for C$_{17}$H$_{14}$N$_5$OBr.0.3 H$_2$O: C, 52.40; H, 3.78; N, 17.97. Found: C, 52.37; H, 3.65; N, 17.70.

EXAMPLE 51

N-[4-(3-Bromo-phenylamino)-pyrido[3,4-d] pyrimidin-6-yl]cinnamide

To a 0–5° C. solution of 6-amino-4-[(3-bromophenyl) amino]pyrido[3,4-d]pyrimidine (32 mg, 0.1 mmol), trans-cinnamic acid (60 mg, 0.4 mmol), in pyridine (0.4 mL) stirred under N$_2$ was added 1-(3-dimethylaminopropyl)-3-ethylcarbodiimide hydrochloride (98 mg, 0.5 mmol). Cooling was removed, and the mixture was stirred at 25° C. After 2 hours, the solution was diluted with water, and the suspension was stirred for 15 minutes. The solids were collected, then dissolved in ethyl acetate. The solution was washed with 5% aqueous sodium bicarbonate, dried (MgSO$_4$), and filtered through flash SiO$_2$. The filtrate was concentrated to a solid that was triturated in hot ethyl acetate. The solids were collected to leave product, (23 mg, 51%) mp 253–256° C.

$^1$H NMR [(CD$_3$)$_2$SO]: δ 11.07 (s, 1H, exchanges D$_2$O), 10.36 (s, 1H, exchanges D$_2$O), 9.06 (s, 2H; with D$_2$O wash, collapses to 9.06 [s, 1H] and 9.02 [s, 1H]), 8.67 (s, 1H), 8.19 (s, 1H), 7.90 (d, J=7.7 Hz, 1H), 7.72–7.65 (m, 3H), 7.51–7.34 (m, 5H), 7.14 (d, J=15.7, 1H).

Mass Spectrum (APCI) m/z (relative %): 445.9 (97), 446.9 (24), 447.9 (100), 448.9 (26).

Analysis calculated for C$_{22}$H$_{16}$N$_5$OBr.0.2 H$_2$O: C, 58.73; H, 3.67; N, 15.57. Found: C, 58.79; H, 3.66; N, 15.37.

EXAMPLE 52

N-[4-(3-Bromo-phenylamino)-pyrido[3,4-d]pyrimidin-6-yl]-E,3-chloroacrylamide

To a −20° C. solution of 6-amino-4-[(3-bromophenyl)amino]pyrido[3,4-d]pyrimidine (128 mg, 0.4 mmol), and cis-3-chloroacrylic acid acid (172 mg, 1.6 mmol) in pyridine (2 mL) stirred under N$_2$ was added 1-(3-dimethylaminopropyl)-3-ethylcarbodiimide hydrochloride (392 mg, 1.5 mmol). After 4.5 hours, additional cis-3-chloroacrylic acid acid (57 mg) and 1-(3-dimethylaminopropyl)-3-ethylcarbodiimide hydrochloride (130 mg) were added and the temperature was brought to −10° C. After a total reaction time of 7 hours, the viscous, dark mixture was diluted with DMF and the resultant solution was poured into 1:1 ethyl acetate:water. The resultant mixture was shaken vigorously and the phases separated. The aqueous phase was further extracted (2×), then the combined organic phases were washed with brine (2×), dried (MgSO$_4$), and filtered through flash SiO$_2$. The filtrate was concentrated to a solid that was dissolved in warm ethyl acetate. The solution was purified by column chromatography over flash SiO$_2$ eluting with ethyl acetate. The product fractions were pooled and concentrated to solid that was triturated in 1:1 ethyl acetate:tert-butyl methyl ether. The solids were collected and dried at 0.1 mm/25° C. to leave product (30 mg, 18%) of product, mp 165–175° C. (dec) following crystallization from ethyl acetate.

$^1$NMR [(CD$_3$)$_2$SO]: δ 11.09 (s, 1H, exchanges D$_2$O), 10.38 (s, EH, exchanges D$_2$O), 9.04 (s, 1H), 9.00 (s, 1H), 8.66 (s, 1H), 8.16 (t, J=1.9 Hz, 1H), 7.88 (dt, J=7.7, 1.7 Hz, 1H), 7.40–7.33 (m, 2H), 7.07 (d, J=8.0 Hz, 1H), 6.77 (d, J=8.0 Hz, 1H).

Mass Spectrum (APCI) m/z (relative %): 365.8 (29), 366.8 (36), 367.8 (35), 368.8 (35), 401.8 (82), 402.8 (18), 403.8 (100), 404.8 (20), 405.8 (29). Analysis calculated for C$_{16}$H$_{11}$N$_5$OBrCl.0.2 H$_2$O.0.2 C$_4$H$_8$O$_2$: C, 47.38; H, 3.08; N, 16.44. Found: C, 47.53; H, 3.15; N, 16.25.

EXAMPLE 53

N-[4-(3-Bromo-phenylamino)-pyrido[3,4-d]pyrimidin-6-yl]-propynamide

To a −20° C. solution of 6-amino-4-[(3-bromophenyl)amino]pyrido[3,4-d]pyrimidine (94 mg, 0.3 mmol), and propiolic acid (66 μL, 1.05 mmol) in pyridine (1.2 mL) stirred under N$_2$ was added 1-(3-dimethylaminopropyl)-3-ethylcarbodiimide hydrochloride (294 mg, 1.5 mmol). After 2.25 hours, additional propiolic acid (33 μL) and 1-(3-dimethylaminopropyl)-3-ethylcarbodiimide hydrochloride (147 mg) were added to the cold solution. After a total reaction time of 7.5 hours, the viscous, dark mixture was diluted with DMF, and the resultant solution was poured into 1:1 ethyl acetate:water. The resultant mixture was shaken vigorously and the phases separated. The aqueous phase was further extracted (2×), then the combined organic phases were washed with brine (2×), dried (MgSO$_4$), and filtered through flash SiO$_2$. The filtrate was concentrated to a solid that was dissolved in warm ethyl acetate. The solution was purified by column chromatography over flash SiO$_2$ eluting with ethyl acetate. The product fractions were pooled and concentrated to solid that was triturated in 1:1 ethyl acetate:tert-butyl methyl ether. The solids were collected and dried at 0.1 mm/25° C. to leave product (16 mg, 14%), mp >150° C. (dec).

$^1$H NMR [(CD$_3$)$_2$SO]: δ 11.69 (s, 1H, exchanges D$_2$O), 10.31 (s, 1H, exchanges D$_2$O), 9.05 (s, 1H), 8.83 (s, 1H), 8.68 (s, 1H), 8.15 (s, 1H), 7.87 (d, J=7.2 Hz, 1H), 7.40–7.33 (m, 2H), 4.54 (s, 1H).

Mass Spectrum (APCI) m/z (relative %): 365.8 (69), 366.8 (28), 367.8 (100), 368.9 (50), 369.9 (14).

Analysis calculated for C$_{16}$H$_{10}$N$_5$OBr.0.1 H$_2$O.0.1 C$_4$H$_8$O$_2$: C, 52.00; H, 2.93; N, 18.49. Found: C, 51.89; H, 2.78; N, 18.50.

EXAMPLE 54

N-[4-[(3-Bromo-phenyl)amino]quinazolin-6-yl]-E,4-(3-(N,N-dimethylamino)propoxy-4-oxobut-2-enamide tris trifluoroacetate A solution of 6-amino-4-[(3-bromophenyl)amino]quinazoline (158 mg, 0.5 mmol) in THF (10 mL) was added dropwise over 15 minutes to a solution of fumaroyl chloride (382 mg, 2.5 mmol) in THF (10 mL) stirred under N$_2$ at 0° C. After 1 hour at 0° C., the suspension was allowed to settle, and the supernatant was decanted. Fresh THF (5 mL) was added, and the suspension was stirred at 0° C. whilst a solution of 3-(N,N-dimethylamino)propan-1-ol (1.18 mL, 10 mmol) in THF (5 mL) was added dropwise. The suspension was stirred at 25° C. for 1 hour, the solvent was stripped under reduced pressure, and the residue was treated with cold water. The solid was collected by Buchner filtration, dissolved in a minimum DMF, and absorbed onto silica gel (2 g) and dried. The solid was used as the origin in silica gel flash chromatography (50 g) eluting with CH$_2$Cl$_2$/MeOH (2:1). The best fractions were pooled, and stripped, dissolved in acetic acid/water (3:2, 2.5 mL), passed through a 0.45μ filter, and purified by HPLC on a Vidac C18 218TP1022 reverse phase HPLC column, eluting with a 10% to 50% gradient of 0.1% TFA in water/0.1% TFA in CH$_3$CN over 60 minutes. The pure fractions were pooled and lyophilized to give N-[4-[(3-bromophenyl)amino]quinazolin-6-yl]-E,4-(3-(N,N-dimethylamino)propoxy-4-oxobut-2-enamide tris trifluoroacetate (51 mg, 12%) as a yellow solid, mp 60° C.

$^1$H NMR [(CD$_3$)$_2$SO]: δ 11.14 (s, 1H, NH), 10.85 (br s, 1H, NH), 9.57 (br s, 1H, NH), 9.01 (d, J=1.7 Hz, 1H, H5), 8.79 (s, 1H, H2), 8.07 (s, 1H, H2'), 8.02 (dd, J=2.1, 9.0 Hz, 1H, H7), 7.89 (d, J=8.9 Hz, 1H, H8), 7.78 (d, J=6.5 Hz, H6'), 7.43 (m, 2H, H4' & H5'), 7.34 (d, J=15.4 Hz, 1H, H3-butenyl), 6.84 (d, J=15.4 Hz, 1H, H2-butenyl), 4.26 (t, J=6.2 Hz, 2H, OCH$_2$), 3.19 (m, 2H, CH$_2$N), 2.81 (d, J=4.6 Hz, 6H, Me), 2.05 (m, 2H, CH$_2$).

Mass Spectrum (APCI): 499.8 (100, $^{81}$BrMH$^+$), 497.9 (97, $^{79}$BrMH$^+$).

Calculated for C$_{23}$H$_{24}$BrN$_5$O$_3$.3CF$_3$COOH: C, 40.15; H, 3.49; N, 8.07%. Found: C, 40.06; H, 3.36; N, 8.25%.

EXAMPLE 55

3-[4-(3-Bromo-phenylamino)-quinazolin-6-ylcarbamoyl]acrylic acid (Z)

To a solution of 6-amino-4-[(3-bromophenyl)amino]quinazoline (0.78 g, 2.5 mmol) in 8 mL of DMF was added maleic anhydride (0.266 g, 2.7 mmol), and the mixture was heated with stirring in a 70° C. oil bath for 2.5 hours. The resulting suspension was cooled to room temperature and then diluted with water. The solid was collected, washed sequentially with a mixture of toluene/DMF (1:1), water, and IPA. The solid was dried in vacuo at 60° C. for 16 hours to afford 3-[4-(3-bromophenylamino)-quinazolin-6-ylcarbamoyl]-acrylic acid (Z) (0.87 g, 86%) as a pale yellow powder, mp 224–225° C. (decomposition with gas evolution).

$^1$H NMR [(CD$_3$)$_2$SO]: δ 13.00 (br s, 1H, COOH), 10.85 (br s, 1H, NH), 9.96 (br s, 1H, NH), 8.73 (d, J=1.8 Hz, 1H, H5), 8.54 (s, 1H, H2), 8.11 (br s, 1H, Me$_2$NCH̲O), 7.91–7.75 (m, 4H), 7.32–7.24 (m, 2H), 6.46 (d, J=12.0 Hz, 1H, CH̲=CH), 6.35 (d, J=12.0 Hz, 1H, CH=CH̲), 2.84 (s, 3H, Me̲$_2$NCHO), 2.68 (s, 3H, Me̲$_2$NCHO).

Mass Spectrum (APCI): 412.8 (100, $^{81}$BrM$^+$), 410.8 (96, $^{79}$BrM$^+$); 413.8 (26, $^{81}$BrMH$^+$), 411.8 (24, $^{79}$BrMH$^+$).

Calculated for C$_{18}$H$_{13}$BrN$_4$O$_3$.0.81 DMF: C, 51.94; H, 3.98; N, 14.26%. Found: C, 51.97; H, 3.98; N, 14.40%.

EXAMPLE 56

N-[4-[(3-Bromophenyl)amino]quinazolin-6-yl]-E,4-(3-(N,N-dimethylamino)propylamino-4-oxobut-2-enamide A solution of 6-amino-4-[(3-bromophenyl)amino] quinazoline (158 mg, 0.5 mmol) in THF (10 mL) was added dropwise over 15 minutes to a solution of fumaroyl chloride (382 mg, 2.5 mmol) in THF (10 mL) stirred under N$_2$ at 0° C. After 1 hour at 0° C., the suspension was allowed to settle, and the supernatant was decanted. Fresh THF (5 mL) was added and the suspension was stirred at 0° C. whilst a solution of 3-(N,N-dimethylamino)prop-1-ylamine (1.26 mL, 10 mmol) in THF (5 mL) was added dropwise. The suspension was stirred at 25° C. for 1 hour, the solvent was stripped under reduced pressure, and the residue was treated with cold water. The solid was collected by Buchner filtration, dissolved in boiling MeOH (25 mL), filtered, and the solvent was removed under reduced pressure. The residue was dissolved in acetic acid/water (3:2, 2.5 mL), and purified by HPLC on a Vidac C18 218TP1022 reverse phase HPLC column, eluting with a 10% to 50% gradient of 0.1% TFA in water/0.1% TFA in CH$_3$CN over 60 minutes. The pure fractions were pooled and lyophilized to give N-[4-[(3-bromophenyl)amino]quinazolin-6-yl]-E,4-(3-(N,N-dimethylamino)prop-1-ylamino-4-oxobut-2-enamide tris trifluoroacetate (154 mg, 37%) as a yellow solid, mp 40° C.

$^1$H NMR [(CD$_3$)$_2$SO]: δ 11.02 (s, 1H, NH), 9.50 (br s, 1H, NH), 9.02 (d, J=1.7 Hz, 1H, H5), 8.82 (s, 1H, H2), 8.74 (t, J=5.7 Hz, 1H, NH), 8.05 (s, 1H, H2'), 8.02 (dd, J=2.1, 9.0 Hz, 1H, H7), 7.89 (d, J=8.9 Hz, 1H, H8), 7.76 (d, J=7.2 Hz, H6'), 7.45 (m, 2H, H4' & H5'), 7.17 (d, J=14.9 Hz, 1H, H3-butenyl), 7.05 (d, J=15.2 Hz, 1H, H2-butenyl), 3.26 (m, 2H, NCH$_2$), 3.08 (m, 2H, CH$_2$N), 2.79 (d, J=4.8 Hz, 6H, Me), 1.83 (m, 2H, CH$_2$).

Mass Spectrum (APCI): 498.8 (100, $^{81}$BrMH$^+$), 496.9 (97, $^{79}$BrMH$^+$).

Calculated for C$_{23}$H$_{25}$BrN$_6$O$_2$.3CF$_3$COOH: C, 41.49; H, 3.36; N, 10.01%. Found: C, 41.44; H, 3.60; N, 10.33%.

EXAMPLE 57

4-[(3-Bromo-phenyl)amino]-6-(ethenesulfonyl)-pyrido[3,4-d]pyrimidine

2-[4-(3-Bromo-phenylamino)-pyrido[3,4-d] pyrimidin-6-ylsulfanyl]-ethanol

A nitrogen purged solution of 2-mercaptoethanol (1.75 mL, 25 mmol), and 4-[3-bromophenyl)amino]-6-fluoropyrido[3,4-d]pyrimidine (1.6 g, 5 mmol), in DMSO (10 mL) was treated with anhydrous cesium carbonate (3.26 g, 10 mmol). The stirred solution was heated at 50° C. for 2 hours, then poured into 2% aqueous hydrochloric acid (180 mL). After stirring the suspension for 15 minutes, the solids were collected, washed well with water, and dissolved in DMF. The solution was poured into 1:1 water:ethyl acetate and the resultant mixture was extracted with ethyl acetate (3×). The combined extracts were washed with brine, dried (MgSO$_4$), and filtered through flash SiO$_2$. The filtrate was concentrated to a solid that was triturated in ethyl acetate. The solids were collected to give 1.24 g (66%) the product, mp 182–185° C. in two crops, and 98 mg (5%) of a third crop, mp 179–183° C.

$^1$H NMR [(CD$_3$)$_2$SO]: δ 10.03 (s, 1H, exchanges D$_2$O), 9.10 (s, 1H), 8.69 (s, 1H), 8.35 (s, 1H), 8.22 (t, J=1.9 Hz, 1H), 7.91 (dt, J=7.7, 1.9 Hz, 1H), 7.42–7.34 (m, 2H), 5.04 (t, J=5.5 Hz, exchanges D$_2$O, 1H), 3.68 (dd, J=6.8, 5.7 Hz, 2H), 3.36 (t, J=6.8 Hz, 2H).

Mass Spectrum (APCI) m/z (relative %): 374.8 (49), 375.8 (10), 376.9 (100), 377.8 (23), 378.9 (63), 379.8 (14).

Analysis calculated for C$_{15}$H$_{13}$N$_4$OSBr: C, 47.76; H, 3.47; N, 14.85. Found: C, 47.65; H, 3.38; N, 14.55.

2-[4-(3-Bromo-phenylamino)-pyrido[3,4-d] pyrimidine-6-sulfonyl]-ethanol

A 0–5° C. stirred suspension of 2-[4-(3-bromo-phenylamino)-pyrido[3,4-d]pyrimidin-6-ylsulfanyl]ethanol (755 mg, 2 mmol) in chloroform (30 mL) was treated with meta-chloroperbenzoic acid (1.27 g, 57–86%). The suspension was slowly warmed to 25° C. over a 4 hour period. After 14.5 and 17.5 hours, respectively, the suspension was treated with an additional charge of the oxidant (720 mg, 720 mg). After 19.5 hours total reaction time, the thin suspension was cooled to 0–5° C., and treated with DMSO (2 mL). Cooling was removed, and the solution was stirred for 30 minutes. The mixture was then distributed between ethyl acetate and 5% aqueous sodium bicarbonate. The organic phase was washed with brine, dried (MgSO$_4$), and concentrated to a reduced volume that was purified by flash SiO$_2$ column chromatography eluting with ethyl acetate. The product fractions were combined and concentrated to a solid that was crystallized from ethyl acetate to give the product (460 mg, 56%), mp 210–212° C. The filtrate was further processed to afford 84 mg (10%) of a second crop, mp 208–209° C.

$^1$H NMR (CF$_3$CO$_2$H): δ 10.96 (s, 1H), 10.90 (s, 1H), 10.42 (s, 1H), 9.47 (s, 1H), 9.16 (d, J=8.2 Hz, 1H), 9.05 (d, J=8.2 Hz, 1H), 8.83 (t, J=8.0, 1H), 5.81 (t, J=5.2 Hz, 2H), 5.43 (t, J=5.2 Hz, 2H).

Mass Spectrum (APCI) m/z (relative %): 378.7 (39), 380.7 (45), 408.7 (100), 409.7 (15), 410.7 (97), 411.7 (17).

Analysis calculated for C$_{15}$H$_{13}$N$_4$O$_3$SBr: C, 44.02; H, 3.20; N, 13.69. Found: C, 44.09; H, 3.14; N, 13.44.

4-[(3-Bromo-phenyl)amino]-6-(ethenesulfonyl)-pyrido[3,4-d]-pyrimidine

To a 0–5° C. stirred suspension of 2-[4-(3-bromo-phenylamino)-pyrido[3,4-d]pyrimidine-6-sulfonyl]ethanol (41 mg, 0.1 mmol), and triethylamine (31 μL, 0.22 mmol) in dichloromethane (0.5 mL) under N$_2$ was added dropwise methanesulfonyl chloride (9.3 μL, 0.12 mmol). Additional charges of methanesulfonyl chloride (9.3 μL, 9.3 μL) were added after 45 minutes, and 1.5 hours, the latter with additional triethylamine (50 μL). After reaction for a total of 2.5 hours, the cold solution was quenched with 5% aqueous sodium bicarbonate, then extracted with ethyl acetate (2×). The combined organic extracts were dried (MgSO$_4$) then filtered through a pad of flash SiO$_2$. The filtrate was concentrated to a solid that was crystallized from ethyl acetate to leave the product (17 mg, 44%), mp 214–217° C.

$^1$H NMR [(CD$_3$)$_2$SO]: δ 10.64 (s, 1H, exchanges D$_2$O), 9.30 (s, 1H), 9.25 (s, 1H), 8.87 (s, 1H), 8.16 (s, 1H), 7.89–7.85 (m, 1H), 7.39–7.33 (m, 2H), 7.17 (dd, J=10.0, 16.5 Hz, 1H), 6.46 (d, J=16.4 Hz, 1H), 6.37 (d, J=10.0 Hz, 1H).

EXAMPLE 58

N-(3-Bromo-phenyl)-N-[6-(2,5-dioxo-2,5-dihydro-pyrrol-1-yl)-quinazolin-4-yl]-acetamide Sodium acetate (0.10 g, 1.2 mmol) was added to a suspension of 3-[4-(3-bromo-phenylamino)-quinazolin-6-ylcarbamoyl]-acrylic acid (Z) (0.25 g, 0.61 mmol) in 5 mL of acetic anhydride, and the mixture was heated under reflux for 30 minutes. After cooling to room temperature, the reaction was filterd and the filtrate concentrated to dryness in vacuo. The residue was taken up in EtOAc and washed sequentially with saturated sodium bicarbonate, water, and brine. The EtOAc portion was dried over magnesium sulfate, filtered and concentrated to afford a faintly pink solid. The solid was recrystallized twice from EtOAc to afford N-(3-bromo-phenyl)-N-[6-[2,5-dioxo-2,5-dihydro-pyrrol-1-yl)-quinazolin-4-yl]-acetamide (0.104 g, 39%) as an off-white powder, mp 174–175° C.

$^1$H NMR [CDCl$_3$]: δ 9.24 (s, 1H, H2), 8.16 (d, J=9 Hz, 1H, H8), 8.10 (d, J=2 Hz, 1H, H5), 8.03 (dd, J=9 Hz, J=2 Hz, 1H, H7), 7.59 (t, 1H, J=2 Hz, H2'), 7.45 (m, 1H, H4'), 7.38 (m, 1H, H6'), 7.27 (d, 1H, J=7 Hz, H5'), 6.91 (s, 2H, C$\underline{H}$=C$\underline{H}$), 2.15 (s, 3H, CH$_3$).

Mass Spectrum (APCI): 438.7 (89, $^{81}$BrMH$^+$), 436.7 (79, $^{79}$BrMH$^+$); 439.7 (17, $^{81}$BrM$^+$), 437.7 (19, $^{79}$BrM$^+$); 470.7 (100, $^{81}$BrM+MeOH), 468.8 (95, $^{79}$BrM+MeOH).

Calculated for C$_{20}$H$_{13}$BrN$_4$O$_3$: C, 54.94; H, 3.00; N, 12.81%. Found: C, 54.90; H, 2.97; N, 12.61%.

The following compounds can be made using the schemes and examples provided above:

1-[4-(3-Bromo-phenylamino)-quinazolin-6-yl]-pyrrole-2,5-dione;

1-[4-(3-Bromo-phenylamino)-quinazolin-6-yl]-prop-2-en-1-one;

Acrylic acid 4-(3-bromo-phenylamino)-quinazolin-6-yl ester;

Methyl N-[4-[(3-bromophenyl)amino]-P-ethenylpyrido[3,4-d]pyrimidin-6-yl]phosphonamidate;

Acrylic acid 4-(3-bromo-phenylamino)-quinazolin-7-yl ester;

1-[4-(3-Bromo-phenylamino)-quinazolin-6-yl]-but-3-en-2-one;

Acrylic acid 4-(3-chloro-4-fluoro-phenylamino)-7-methoxy-quinazolin-6-yl ester;

N-[4-(3-Bromo-phenylamino)-7-(3-morpholin-4-yl-propoxy)-pyrido[3,2-d]pyrimidin-6-yl]-acryl amide;

Penta-2,3-dienoic acid [4-(3-bromo-phenylamino)-quinazolin-6-yl]-amide;

Propa-1,2-diene-1-sulfonic acid [4-(3-bromo-phenylamino)-quinazolin-6-yl]-amide;

Methyl N-[4-[(3-bromophenyl)amino]-6-quinazolinyl]-P-(1,2-propadienyl)phosphonamidate;

N-[1-(3-Bromo-phenylamino)-9H-2,4,9-triazafluoren-7-yl]-acrylamide;

N-[4-(3-Bromo-phenylamino)-9H-1,3,9-triazafluoren-6-yl]-acrylamide;

N-[4-(3-Chloro-4-fluoro-phenylamino)-quinazolin-6-yl]-acrylamide;

N-(4-Phenylmethylamino-quinazolin-6-yl)-acrylamide;

(S)-N-[4-(1-Phenyl-ethylamino)-quinazolin-6-yl]-acrylamide;

(R)-N-[4-(1-Phenyl-ethylamino)-quinazolin-6-yl]-acrylamide;

But-2-enedioic acid [4-(3-chloro-4-fluoro-phenylamino)-quinazolin-6-yl]-amide (3-dimethylaminopropyl)-amide;

N-[4-(3-Chloro-4-fluoro-phenylamino)pyrido[3,4-d]pyrimidin-6-yl]-acrylamide;

N-[4-(3-Chloro-4-fluoro-phenylamino)pyrido[3,4-d]pyrimidin-6-yl]-N-methyl-acrylamide;

But-2-enedioic acid [4-(3-chloro-4-fluoro-phenylamino)-pyrido[3,4-d]pyrimidin-6-yl]-amide (3-dimethylamino-propyl)-amide;

But-2-enedioic acid [4-(3-chloro-4-fluoro-phenylamino)-pyrido[3,4-d]pyrimidin-6-yl]-amide (3-imidazol-1-yl-propyl)-amide;

4,4-Difluoro-8-morpholin-4-yl-oct-2-enoic acid [4-(3-chloro-4-fluoro-phenylamino)-pyrido[3,4-d]pyrimidin-6-yl]-amide;

8-Dimethylamino-4,4-difluoro-oct-2-enoic acid (4-(3-chloro-4-fluoro-phenylamino)-pyrido[3,4-d]pyrimidin-6-yl]-amide;

7-Dimethylamino-4,4-difluoro-hept-2-enoic acid [4-(3-chloro-4-fluoro-phenylamino)-pyrido[3,4-d]pyrimidin-6-yl]-amide;

4,4-Difluoro-7-morpholin-4-yl-hept-2-enoic acid [4-(3-chloro-4-fluoro-phenylamino)-pyrido[3,4-d]pyrimidin-6-yl]-amide;

6-Dimethylamino-hex-2-ynoic acid [4-(3-chloro-4-fluoro-phenylamino)-pyrido[3,4-d]pyrimidin-6-yl]-amide;

6-Morpholin-4-yl-hex-2-ynoic acid [4-(3-chloro-4-fluoro-phenylamino)-pyrido[3,4-d]pyrimidin-6-yl]-amide;

7-Dimethylamino-hept-2-ynoic acid [4-(3-chloro-4-fluoro-phenylamino)-pyrido(3,4-d]pyrimidin-6-yl]-amide;

7-Morpholin-4-yl-hept-2-ynoic acid [4-(3-chloro-4-fluoro-phenylamino)-pyrido[3,4-d]pyrimidin-6-yl]-amide;

5-Dimethylamino-pent-2-ynoic acid [4-(3-chloro-4-fluoro-phenylamino)-pyrido[3,4-d]pyrimidin-6-yl]-amide;

5-Morpholin-4-yl-pent-2-ynoic acid [4-(3-chloro-4-fluoro-phenylamino)-pyrido[3,4-d]pyrimidin-6-yl]-amide;

5-Imidazol-1-yl-pent-2-ynoic acid [4-(3-chloro-4-fluoro-phenylamino)-pyrido[3,4-d]pyrimidin-6-yl]-amide;

5-(4-Methyl-piperazin-1-yl)-pent-2-ynoic acid [4-(3-chloro-4-fluoro-phenylamino)-pyrido[3,4-d]pyrimidin-6-yl]-amide;

4-[4-(3-Chloro-4-fluoro-phenylamino)-pyrido[3,4-d]pyrimidin-6-ylcarbamoyl]-but-3-enoic acid 2-(4-methyl-piperazin-1-yl)-ethyl ester;

4-[4-(3-Chloro-4-fluoro-phenylamino)-pyrido[3,4-d]pyrimidin-6-ylcarbamoyl]-but-3-enoic acid 2-(imidazol-1-yl)-ethyl ester;

Pent-2-enedioic acid 1-{[4-(3-chloro-4-fluoro-phenylamino)-pyrido[3,4-d]pyrimidin-6-yl]-amide}5-[(3morpholin-4-yl-propyl)-amide];

Pent-2-enedioic acid 1-{[4-(3-chloro-4-fluoro-phenylamino)-pyrido[3,4-d]pyrimidin-6-yl]-amide}5-[(3-diethylamino-propyl)-amide];

4-[4-(3-Chloro-4-fluoro-phenylamino)-pyrido[3,4-d]pyrimidin-6-ylcarbamoyl]-but-3-enoic acid 2-morpholin-4-yl-ethyl ester;

Pent-2-enedioic acid 1-{[4-(3-chloro-4-fluoro-phenylamino)-pyrido[3,4-d]pyrimidin-6-yl]-amide}5-{[3-4-methyl-piperazin-1-yl)-propyl]-amide};

(3-Chloro-4-fluoro-phenyl)-{6-[2-(3-dimethylamino-propoxy)-ethenesulfonyl]-pyrido[3,4-d]pyrimidin-4-yl}amine;

(3-Chloro-4-fluoro-phenyl)-(6-{2-[4-(4-methyl-piperazin-1-yl)-butylamino]-ethenesulfonyl}pyrido[3,4-d]pyrimidin-4-yl)-amine;

(3-Chloro-4-fluoro-phenyl)-[6-(5-morpholin-4-yl-pent-1-ene-1-sulfonyl)-pyrido[3,4-d]pyrimidin-4-yl}amine;

3-Chloro-4-fluoro-phenyl)-(6-ethenesulfinyl-pyrido[3,4-d]pyrimidin-4-yl]-amine;

3-[4-(1-Phenyl-ethylamino)-quinazolin-6-ylcarbamoyl]-acrylic acid 2-morpholin-4-yl-ethyl ester;

But-2-enedioic acid (4-imidazol-1-yl-butyl)-amide [4-(1-phenyl-ethylamino)-quinazolin-6-yl]-amide;

4-[4-(1-Phenyl-ethylamino)-quinazolin-6-ylcarbamoyl]-but-3-enoic acid 3-diethylamino-propyl ester;

Pent-2-enedioic acid 5-{[2-(4-methyl-piperazin-1-yl)-ethyl]-amide}1-{[4-(1-phenyl-ethylamino)-quinazolin-6-yl]-amide};

4,4-Difluoro-7-morpholin-4-yl-hept-2-enoic acid [4-(1-phenyl-ethylamino)-quinazolin-6-yl]-amide;

7-Dimethylamino-4,4-difluoro-hept-2-enoic acid [4-(1-phenyl-ethylamino)-quinazolin-6-yl]-amide;

7-Imidazol-1-yl-hept-2-ynoic acid [4-(1-phenyl-ethylamino)-quinazolin-6-yl]-amide;

6-Dimethylamino-hex-2-ynoic acid [4-(1-phenyl-ethylamino)-quinazolin-6-yl]-amide;

But-2-enedioic acid [4-(3-bromo-phenylamino)pyrido[3,4-d]pyrimidin-6-yl]-amide (3-dimethylaminopropyl)-amide;

But-2-enedioic acid [4-(3-bromo-phenylamino)pyrido[3,4-d]pyrimidin-6-yl]-amide (3-imidazol-1-yl-propyl)-amide;

4,4-Difluoro-8-morpholin-4-yl-oct-2-enoic acid [4-(3-bromo-phenylamino)-pyrido[3,4-d]pyrimidin-6-yl]-amide;

8-Dimethylamino-4,4-difluoro-oct-2-enoic acid [4-(3-bromo-phenylamino)-pyrido[3,4-d]pyrimidin-6-yl]-amide;

7-Dimethylamino-4,4-difluoro-hept-2-enoic acid (4-(3-bromo-phenylamino)-pyrido[3,4-d]pyrimidin-6-yl]-amide;

4,4-Difluoro-7-morpholin-4-yl-hept-2-enoic acid [4-(3-bromo-phenylamino)-pyrido[3,4-d]pyrimidin-6-yl]-amide;

6-Dimethylamino-hex-2-ynoic acid [4-(3-bromo-phenylamino)-pyrido[3,4-d]pyrimidin-6-yl]-amide;

6-Morpholin-4-yl-hex-2-ynoic acid [4-(3-bromo-phenylamino)-pyrido[3,4-d]pyrimidin-6-yl]-amide;

7-Dimethylamino-hept-2-ynoic acid [4-(3-bromo-phenylamino)-pyrido[3,4-d]pyrimidin-6-yl]-amide;

7-Morpholin-4-yl-hept-2-ynoic acid [4-(3-bromo-phenylamino)-pyrido[3,4-d]pyrimidin-6-yl]-amide;

5-Dimethylamino-pent-2-ynoic acid [4-(3-bromo-phenylamino)-pyrido[3,4-d]pyrimidin-6-yl]-amide;

5-Morpholin-4-yl-pent-2-ynoic acid [4-(3-bromo-phenylamino)-pyrido[3,4-d]pyrimidin-6-yl]-amide;

5-Imidazol-1-yl-pent-2-ynoic acid [4-(3-bromo-phenylamino)-pyrido[3,4-d]pyrimidin-6-yl]-amide;

5-(4-Methyl-piperazin-1-yl)-pent-2-ynoic acid [4-(3-bromo-phenylamino)-pyrido[3,4-d]pyrimidin-6-yl]-amide;

4-[4-(3-Bromo-phenylamino)-pyrido[3,4-d]pyrimidin-6-ylcarbamoyl]-but-3-enoic acid 2-(4-methyl-piperazin-1-yl)-ethyl ester;

4-[4-(3-Bromo-phenylamino)-pyrido[3,4-d]pyrimidin-6-ylcarbamoyl]-but-3-enoic acid 2-imidazol-1-yl-ethyl ester;

Pent-2-enedioic acid 1-{[4-(3-bromo-phenylamino)-pyrido[3,4-d]pyrimidin-6-yl]-amide}5-[(3-morpholin-4-yl-propyl)-amide];

Pent-2-enedioic acid 1-{[4-(3-bromo-phenylamino)-pyrido[3,4-d]pyrimidin-6-yl]-amide}5-[(3-diethylamino-propyl)-amide];

4-[4-(3-Bromo-phenylamino)-pyrido[3,4-d]pyrimidin-6-ylcarbamoyl]-but-3-enoic acid 2-morpholin-4-yl-ethyl ester;

Pent-2-enedioic acid 1-{[4-(3-bromo-phenylamino)-pyrido[3,4-d]pyrimidin-6-yl]-amide}5-{[3-(4-methyl-piperazin-1-yl)-propyl]-amide};

(3-Bromo-phenyl)-{6-[2-(3-dimethylamino-propoxy)-ethenesulfonyl]-pyrido[3,4-d]pyrimidin-4-yl}-amine;

(3-Bromo-phenyl)-(6-{2-[4-(4-methyl-piperazin-1-yl)-butylamino]-ethenesulfonyl}-pyrido[3,4-d]pyrimidin-4-yl)-amine;

(3-Bromo-phenyl)-[6-(5-morpholin-4-yl-pent-1-ene-1-sulfonyl)-pyrido[3,4-d]pyrimidin-4-yl]-amine;

(3-Bromo-phenyl)-(6-ethenesulfinyl-pyrido[3,4-d]pyrimidin-4-yl)-amine;

But-2-enedioic acid [4-(3-chloro-4-fluoro-phenylamino)-quinazolin-6-yl]-amide (3-dimethylaminopropyl)-amide;

But-2-enedioic acid [4-(3-chloro-4-fluoro-phenylamino)-quinazolin-6-yl]-amide (3-imidazol-1-yl-propyl)-amide;

4,4-Difluoro-8-morpholin-4-yl-oct-2-enoic acid [4-(3-chloro-4-fluoro-phenylamino)-quinazolin-6-yl]-amide;

8-Dimethylamino-4,4-difluoro-oct-2-enoic acid [4-(3-chloro-4-fluoro-phenylamino)-quinazolin-6-yl]-amide;

7-Dimethylamino-4,4-difluoro-hept-2-enoic acid [4-(3-chloro-4-fluoro-phenylamino)-quinazolin-6-yl]-amide;

4,4-Difluoro-7-morpholin-4-yl-hept-2-enoic acid [4-(3-chloro-4-fluoro-phenylamino)-quinazolin-6-yl]-amide;

6-Dimethylamino-hex-2-ynoic acid [4-(3-chloro-4-fluoro-phenylamino)-quinazolin-6-yl]-amide;

6-Morpholin-4-yl-hex-2-ynoic acid [4-(3-chloro-4-fluoro-phenylamino)-quinazolin-6-yl]-amide;

7-Dimethylamino-hept-2-ynoic acid [4-(3-chloro-4-fluoro-phenylamino)-quinazolin-6-yl]-amide;

7-Morpholin-4-yl-hept-2-ynoic acid [4-(3-chloro-4-fluoro-phenylamino)-quinazolin-6-yl]-amide;

5-Dimethylamino-pent-2-ynoic acid [4-(3-chloro-4-fluoro-phenylamino)-quinazolin-6-yl]-amide;

5-morpholin-4-yl-pent-2-ynoic acid [4-(3-chloro-4-fluoro-phenylamino)-quinazolin-6-yl]-amide;

5-Imidazol-1-yl-pent-2-ynoic acid [4-(3-chloro-4-fluoro-phenylamino)-quinazolin-6-yl]-amide;

5-(4-Methyl-piperazin-1-yl)-pent-2-ynoic acid [4-(3-chloro-4-fluoro-phenylamino)-quinazolin-6-yl]-amide;

Pent-2-enedioic acid 1-{[4-[3-chloro-4-fluoro-phenylamino)-quinazolin-6-yl]-amide}5-[(3-morpholin-4-yl-propyl)-amide];

Pent-2-enedioic acid 1-{[4-(3-chloro-4-fluoro-phenylamino)-quinazolin-6-yl]-amide}5-[(3diethylamino-propyl)-amide];

4-[4-(3-Chloro-4-fluoro-phenylamino)-quinazolin-6-ylcarbamoyl]-but-3-enoic acid 2-morpholin-4-yl-ethyl ester;

Pent-2-enedioic acid 1-{[4-(3-chloro-4-fluoro-phenylamino)-quinazolin-6-yl]-amide}5-{[3-(4-methyl-piperazin-1-yl)-propyl]-amide};

(3-Chloro-4-fluoro-phenyl)-{6-[2-(3-dimethylamino-propoxy)-ethenesulfonyl]-quinazolin-4-yl}-amine;

(3-Chloro-4-fluoro-phenyl)-(6-{2-[4-(4-methyl-piperazin-1-yl)-butylamino]-ethenesulfonyl}-quinazolin-4-yl)-amine;

But-2-enedioic acid [4-(3-bromo-phenylamino)-quinazolin-6-yl]-amide (3-dimethylamino-propyl)-amide;

But-2-enedioic acid [4-(3-bromo-phenylamino)-quinazolin-6-yl]-amide (3-imidazol-1-yl-propyl)-amide;

4,4-Difluoro-8-morpholin-4-yl-oct-2-enoic acid [4-(3-bromo-phenylamino)-quinazolin-6-yl]-amide;

8-Dimethylamino-4,4-difluoro-oct-2-enoic acid [4-(3-bromo-phenylamino)-quinazolin-6-yl]-amide;

7-Dimethylamino-4,4-difluoro-hept-2-enoic acid [4-(3-bromo-phenylamino)-quinazolin-6-yl]-amide;

4,4-Difluoro-7-morpholin-4-yl-hept-2-enoic acid [4-(3-bromo-phenylamino)-quinazolin-6-yl]-amide;

6-Dimethylamino-hex-2-ynoic acid [4-(3-bromo-phenylamino)-quinazolin-6-yl]-amide;

6-Morpholin-4-yl-hex-2-ynoic acid [4-(3-bromo-phenylamino)-quinazolin-6-yl]-amide;

7-Dimethylamino-hept-2-ynoic acid [4-(3-bromo-phenylamino)-quinazolin-6-yl]-amide;

7-Morpholin-4-yl-hept-2-ynoic acid [4-(3-bromo-phenylamino)-quinazolin-6-yl]-amide;

5-Dimethylamino-pent-2-ynoic acid [4-(3-bromo-phenylamino)-quinazolin-6-yl]-amide;

5-Morpholin-4-yl-pent-2-ynoic acid [4-(3-bromo-phenylamino)-quinazolin-6-yl]-amide;

5-Imidazol-1-yl-pent-2-ynoic acid [4-(3-bromo-phenylamino)-quinazolin-6-yl]-amide;

5-(4-Methyl-piperazin-1-yl)-pent-2-ynoic acid [4-(3-bromo-phenylamino)-quinazolin-6-yl]-amide;

4-[4-(3-Bromo-phenylamino)-quinazolin-6-ylcarbamoyl]-but-3-enoic acid 2-(4-methyl-piperazin-1-yl)-ethyl ester;

4-[4-(3-Bromo-phenylamino)-quinazolin-6-ylcarbamoyl]-but-3-enoic acid 2-imidazol-1-yl-ethyl ester;

Pent-2-enedioic acid 1-{[4-(3-bromo-phenylamino)-quinazolin-6-yl]-amide}5-[(3-morpholin-4-yl-propyl)-amide];

Pent-2-enedioic acid 1-{[4-(3-bromo-phenylamino)-quinazolin-6-yl]-amide}5-[(3-diethylamino-propyl)-amide];

4-[4-(3-Bromo-phenylamino)-quinazolin-6-ylcarbamoyl]-but-3-enoic acid 2-morpholin-4-yl-ethyl ester;

Pent-2-enedioic acid 1-{[4-(3-bromo-phenylamino)-quinazolin-6-yl]-amide}5-{[3-(4-methyl-piperazin-1-yl)-propyl]-amide};

3-[4-(1-Phenyl-ethylamino)-pyrido[3,4-d]pyrimidin-6-ylcarbamoyl]-acrylic acid 2-morpholin-4-yl-ethyl ester;

But-2-enedioic acid (4-imidazol-1-yl-butyl)-amide [4-(1-phenyl-ethylamino)-pyrido[3,4-d]pyrimidin-6-yl]-amide;

4-[4-(1-Phenyl-ethylamino)-pyrido[3,4-d]pyrimidin-6-ylcarbamoyl]-but-3-enoic acid 3-diethylamino-propyl ester;

Pent-2-enedioic acid 5-{[2-(4-methyl-piperazin-1-yl)-ethyl]-amide}1-{[4-(1-phenyl-ethylamino)-pyrido[3,4-d]pyrimidin-6-yl]-amide};

4,4-Difluoro-7-morpholin-4-yl-hept-2-enoic acid [4-(1-phenyl-ethylamino)-pyrido[3,4-d]pyrimidin-6-yl]-amide;

7-Dimethylamino-4,4-difluoro-hept-2-enoic acid (4-(1-phenyl-ethylamino)-pyrido[3,4-d]pyrimidin-6-yl]-amide;

7-Imidazol-1-yl-hept-2-ynoic acid [4-(1-phenyl-ethylamino)-pyrido[3,4-d]pyrimidin-6-yl]-amide;

6-Dimethylamino-hex-2-ynoic acid [4-(1-phenyl-ethylamino)-pyrido[3,4-d]pyrimidin-6-yl]-amide;

But-2-endioic acid [4-(3-chloro-4-fluoro-phenylamino)-7-fluoroquinazolin-6-yl]amide (3-dimethylaminopropyl)amide;

But-2-endioic acid [7-chloro-4-(3-chloro-4-fluoro-phenylamino)quinazolin-6-yl]amide (3-dimethylaminopropyl)amide;

N-[4-[3-(Bromophenyl)amino]-5-fluoro-7-[3-(4-morpholino)propoxy]quinazolin-6-yl]acrylamide; and N-[4-[(3-(Chloro-4-fluorophenyl)amino]-5-fluoro-7-(1,N-imidazoyl)propoxy]quinazolin-6-yl]acrylamide.

BIOLOGICAL METHODS

Tissue Culture

A431 human epidermoid carcinoma cells were obtained from the American Type Culture Collection, Rockville, Md. and maintained as monolayers in DMEM (Dulbecco's modified eagle medium)/F12, 50:50 (Gibco/BRL) containing 10% fetal bovine serum For growth inhibition assays, dilutions of the designated compound in 10 $\mu$L were placed in 24-well Linbro plates (1.7×1.6 cm, flat bottom) followed by the addition of cells (2×10$^4$) in 2 mL of media. The plates were incubated for 72 hours at 37° C. in a humidified atmosphere containing 5% $CO_2$ in air. Cell growth was determined by cell count with a Coulter Model AM electronic cell counter (Coulter Electronics, Inc., Hialeah, Fla.).

Purification of Epidermal Growth Factor Receptor Tyrosine Kinase

Human EGF receptor tyrosine kinase was isolated from A431 human epidermoid carcinoma cells by the following method. Cells were grown in roller bottles in dMEM/F12 media (Gibco/BRL) containing 10% fetal calf serum. Approximately 10$^9$ cells were lysed in 2 volumes of buffer containing 20 mM N-[2-hydroxyethyl]-piperazine-N'-[2- ethane sulfonic acid](Hepes), pH 7.4, 5 mM ethylene glycol-bis(β-aminoethyl ether) N, N, N', N'-tetraacetic acid (EGTA), 1% Triton X-100, 10% glycerol, 0.1 mM sodium orthovanadate, 5 mM sodium fluoride, 4 mM pyrophosphate, 4 mM benzamide, 1 mM dithiothreitol (DTT), 80 μg/mL aprotinin, 40 μg/mL leupeptin, and 1 mM phenylmethyl sulfonyl fluoride (PMSF). After centrifugation at 25,000×g for 10 minutes, the supernatant was applied to a fast Q sepharose column (Pharmacia Biotech., Inc., Piscataway, N.J.) and eluted with a linear gradient from 0.1 M NaCl to 0.4 M NaCl in 50 mM Hepes, 10% glycerol, pH 7.4. Enzyme active fractions were pooled, divided into aliquots, and stored at −100° C. Fibroblast growth factor receptor (FGFR), platelet-derived growth factor (PDGF), insulin, and c-src tyrosine kinases were obtained by methods well-known in the art. For example, see Fry, et al., "Strategies For The Discovery Of Novel Tyrosine Kinase Inhibitors With Anticancer Activity, *Anticancer Drug Design*, 1994;9:331–351.

Tyrosine Kinase Assays

Enzyme assays for $IC_{50}$ determinations were performed in 96 well filter plates (Millipore MADVN6550, Millipore, Bedford, Mass.). The total volume was 0.1 mL containing 20 mM Hepes, pH 7.4, 50 μM sodium vanadate, 40 mM magnesium chloride, 10 μM adenosine triphosphate (ATP) containing 0.5 μCi of [$^{32}$P]ATP, 20 μg of poly Glutamic acid/tyrosine (Sigma Chemical Co., St. Louis, Mo.), 10 ng of EGF receptor tyrosine kinase and appropriate dilutions of inhibitor. All components except the ATP are added to the well and the plate incubated with shaking for 10 minutes at 25° C. The reaction is started by adding [$^{32}$P]ATP, and the plate is incubated at 25° C. for 10 minutes. The reaction is terminated by addition of 0.1 mL of 20% trichloroacetic acid (TCA). The plate is kept at 4° C. for at least 15 minutes to allow the substrate to precipitate. The wells are then washed 5 times with 0.2 mL of 10% TCA and $^{32}$P incorporation determined with a Wallac beta plate counter (Wallac, Inc., Gaithersburg, Pa.). Assays using intracellular kinase domains of PDGF, FGF, and insulin receptors, as well as those for c-src, were performed as described for the EGF receptor except that 10 mM Manganese chloride was included in the reaction.

Western Blotting Procedure

Extracts were made by lysing the monolayers in 0.2 mL of boiling Laemlli buffer (2% sodium dodecyl sulfate, 5% beta-mercaptoethanol, 10% glycerol and 50 mM tris [hydroxymethyl]aminomethane (Tris), pH 6.8), and the lysates were heated to 100° C. for 5 minutes. Proteins in the lysate were separated by polyacrylamide gel electrophoresis and electrophoretically transferred to nitrocellulose. The membrane was washed once in 10 mM Tris, pH 7.2, 150 mM NaCl, 0.01% Azide (TNA), and blocked overnight in TNA containing 5% bovine serum albumin and 1% ovalbumin. The membrane was blotted for 2 hours with antiphosphotyrosine antibody (UBI, 1 μg/mL in blocking buffer) and then washed twice in TNA, once in TNA containing 0.05% Tween-20 detergent and 0.05% nonidet P-40 detergent and twice in TNA. The membranes were then incubated for 2 hours in blocking buffer containing 0.1 μCi/mL of [$^{125}$I] protein A and then washed again as above. After the blots were dry, they were loaded into a film cassette and exposed to X-AR X-ray film (Eastman Kodak Co., Rochester, N.Y.) for 1 to 7 days. Band intensities were determined with a Molecular Dynamics laser densitometer.

Autophosphorylation Assay

A431 human epidermoid carcinoma cells were grown in 6-well plates to about 80% confluency and then incubated in serum-free media for 18 hours. Duplicate sets of cells were treated with a range of concentrations of the designated compound to be tested as an inhibitor for 15 minutes. The cells were then stimulated with 100 ng/mL of EGF for 5 minutes and extracts made as described under the Western Blotting Procedure.

Irreversibility Test Protocol

A431 human epidermoid carcinoma cells were grown in 6-well plates to about 80% confluency and then incubated in serum-free media for 18 hours. Duplicate sets of cells were treated with 2 μM of designated compound to be tested as an irreversible inhibitor for either 1 or 2 hours. One set of cells was then stimulated with 100 ng/mL of EGF for 5 minutes and extracts made as described under the western blotting procedure. The other set of cells were washed free of the compound with warmed serum-free media, incubated for 2 hours, washed again, incubated another 2 hours, washed again, and then incubated a further 4 hours. This set of cells was then stimulated with EGF and extracts made similar to the first set of cells.

Results

Table 1 shows the $IC_{50}$ values of various compounds for inhibition of the isolated EGF receptor tyrosine kinase in the first column, and for inhibition of EGF-stimulated autophosphorylation of the EGF-receptor in A431 cells in the second column. Most compounds of the current invention inhibited the isolated enzyme with low nanomolar or subnanomolar potency and the majority had low nanomolar potency when inhibiting cellular autophosphorylation. Table 2 indicates the ability of A431 cells to recover EGF receptor autophosphorylation activity after complete suppression of the enzyme by these compounds followed by their removal from the medium. The first set of cell extracts (2nd column) shows that many of the compounds tested completely suppressed EGF receptor autophosphorylation after the initial 2 hour incubation. The third column in Table 2 shows the percent return of EGF receptor autophosphorylation activity after the washes and incubation in compound-free medium as described in the methods. At least 30 of the compounds retained 50% or greater inhibition of kinase activity after this treatment with at least 23 of the compounds showing 90%–100% inhibition of the original enzyme activity. Cells treated with all other compounds tested were able to recover 86% to 100% of their EGF-dependent autophosphorylation activity. Reversibility studies where the incubation time was carried out further indicate that the time required for return of 50% of the activity was 21 hours (Table 3). A specific sidechain requirement for irreversible interaction is illustrated by the fact that Compound 9, a very close analog of Compound 3 with equally potent inhibitory activity against the enzyme, was completely reversible. Furthermore the requirement for a conjugated alkene in the sidechain is demonstrated by comparing Compounds 3 and 11 with their saturated analogues 17 and 28. In these cases the compounds all show similar potency against the isolated enzyme and are not well differentiated in the autophosphorylation assay, but Compounds 17 and 28 have no inhibitory effect at the end of 8 hours washoff, whereas the irreversible inhibitors Compounds 3 and 11 have 89% and 100% inhibition of the enzyme at that time.

Table 4 illustrates that Compound 3 retains very high specificity for the EGF receptor tyrosine kinase as opposed to other tyrosine kinase enzymes and indicates that the active sidechain in Example 3 does not indiscriminately interact with other enzymes.

Finally, Compound 3 was tested for its ability to inhibit proliferation in A431 human epidermoid carcinoma cells.

An $IC_{50}$ of 0.30±0.09 micromolar was obtained indicating its ability to stop tumor growth.

The properties of an irreversible inhibitor are attractive because it would help circumvent or solve the potential problems of a short plasma half-life and/or a requirement for prolonged suppression of its target. One bolus injection at an appropriate dose of an irreversible inhibitor would in effect be enough to abolish the existing target activity, and the return of that activity would be dependent on the rate of resynthesis of the target. Since it is known that the half-life for turnover of the EGF receptor is 20 hours in A431 cells, an inhibitor could keep the receptor suppressed with administration once or twice a day. This eliminates the need for multiple injections, or the use of infusion or osmotic pumps. Alternatively, it can allow for lower doses to be used in multiple or continuous dosing regimens to achieve results with an irreversible inhibitor, as the receptor activity is no longer being repressed under equilibrium binding conditions.

TABLE 1

$IC_{50}$S OF EXAMPLES AGAINST ISOLATED EGFR KINASE ACTIVITY AND EGFR AUTOPHOSPHORYLATION IN A431 CELLS

| Example | EGFR Tyrosine Kinase $IC_{50}$ (nM) | Autophos- phorylation $IC_{50}$ (nM) |
|---|---|---|
| 2 | 2.7 | 156 |
| 3 | 0.36 | 14 |
| 4 | 89 | 2090 |
| 5 | 11 | |
| 6 | 104 | |
| 7 | 27 | 130 |
| 8 | 0.029 | 13 |
| 9 | 0.46 | 20 |
| 11 | 0.84 | 2.7 |
| 12 | 910 | >10000 |
| 13 | 1.6 | 90 |
| 14 | 0.25 | 53 |
| 15 | 1.2 | 16 |
| 16 | 3.7 | 2450 |
| 17 | 1.9 | 60 |
| 18 | 1.6 | 2.3 |
| 19 | 0.42 | 4.7 |
| 20 | 0.91 | 4.5 |
| 21 | 3.6 | 5.3 |
| 22 | 1.5 | 27 |
| 23 | 2 | 18 |
| 24 | 4 | 7.9 |
| 25 | 3 | 21 |
| 26 | 1.7 | 3 |
| 27 | 3.3 | 194 |
| 28 | 0.52 | 15 |
| 29 | 1.2 | 28 |
| 30 | 1.4 | 2.7 |
| 31 | 0.55 | 8.7 |
| 32 | 1.75 | 35 |
| 33 | 0.89 | 10 |
| 34 | 0.47 | 5.5 |
| 35 | 0.54 | 108 |
| 36 | 0.91 | 3.4 |
| 37 | 0.48 | 8.3 |
| 38 | 0.17 | 13 |
| 39 | 1.6 | 44 |
| 40 | 0.76 | 2.4 |
| 41 | 1.1 | 5.6 |
| 42 | 23 | 173 |
| 43 | 1.4 | 24 |
| 44 | 21 | 327 |
| 45 | 1.6 | 1039 |
| 46 | 1.2 | 120 |
| 47 | 2.7 | 67 |
| 48 | 1.1 | 27 |
| 49 | 4.2 | 2280 |

TABLE 1-continued $IC_{50}$S OF EXAMPLES AGAINST ISOLATED EGFR KINASE ACTIVITY AND EGFR AUTOPHOSPHORYLATION IN A431 CELLS

| Example | EGFR Tyrosine Kinase $IC_{50}$ (nM) | Autophos- phorylation $IC_{50}$ (nM) |
|---|---|---|
| 50 | 0.5 | 7.7 |
| 51 | 9.1 | 77 |
| 52 | 0.69 | 20 |
| 53 | 0.81 | 52 |
| 54 | 2.4 | 108 |
| 55 | 0.37 | >500 |
| 56 | 0.44 | 59 |
| 57 | 0.43 | >500 |
| 58 | 124 | >500 |

TABLE 2

RECOVERY OF EGF RECEPTOR AUTOPHOSPHORYLATION ACTIVITY IN A431 CELLS AFTER EXPOSURE TO 2 µM INHIBITOR

| Example No. | % Control After 2-Hour Incubation | % Control After 8 Hours in Drug-Free Media Incubation | Irreversible |
|---|---|---|---|
| 2 | 0 | 92 | N |
| 3 | 1 | 13 | Y |
| 4 | 55 | 98 | N |
| 5 | | | N |
| 6 | | | N |
| 7 | | | N |
| 8 | 0 | 95 | N |
| 9 | 0 | 99 | N |
| 11 | 0 | 0 | Y |
| 12 | 85 | 100 | N |
| 13 | 1 | 90 | N |
| 14 | 0 | 50 | Y |
| 15 | 0 | 85 | N |
| 16 | 30 | 85 | N |
| 17 | 0 | 100 | N |
| 18 | 0 | 0 | Y |
| 19 | 0 | 0 | Y |
| 20 | 0 | 0 | Y |
| 21 | 0 | 0 | Y |
| 22 | 0 | 0 | Y |
| 23 | 0 | 0 | Y |
| 24 | 0 | 0 | Y |
| 25 | 0 | 0 | Y |
| 26 | 0 | 0 | Y |
| 27 | 0 | 96 | N |
| 28 | 0 | 100 | N |
| 29 | 0 | 100 | N |
| 30 | 0 | 0 | Y |
| 31 | 0 | 35 | Y |
| 32 | 0 | 0 | Y |
| 33 | 0 | 0 | Y |
| 34 | 0 | 0 | Y |
| 35 | 0 | 20 | Y |
| 36 | 0 | 0 | Y |
| 37 | 0 | 0 | Y |
| 38 | 0 | 0 | Y |
| 39 | 0 | 80 | N |
| 40 | 0 | 0 | Y |
| 41 | 0 | 0 | Y |
| 42 | 12 | 50 | Y |
| 43 | 0 | 0 | Y |
| 44 | 13 | 42 | Y |
| 45 | 0 | 21 | Y |
| 46 | 19 | 59 | Y |
| 47 | 0 | 26 | Y |
| 48 | 0 | 53 | Y |
| 49 | 50 | 75 | N |
| 50 | 0 | 32 | Y |

TABLE 2-continued

RECOVERY OF EGF RECEPTOR AUTOPHOSPHORYLATION
ACTIVITY IN A431 CELLS AFTER EXPOSURE
TO 2 μM INHIBITOR

| Example No. | % Control After 2-Hour Incubation | % Control After 8 Hours in Drug-Free Media Incubation | Irreversible |
|---|---|---|---|
| 51 | 12 | 32 | Y |
| 52 | 0 | 0 | Y |
| 53 | 0 | 0 | Y |
| 54 | 0 | 3 | Y |
| 55 | 32 | 32 | Y |
| 56 | 0 | 0 | Y |
| 57 | 43 | 39 | Y |
| 58 | 81 | 95 | N |

TABLE 3

REVERSIBILITY OF EGF RECEPTOR AUTOPHOSPHORYLATION
INHIBITOR IN A431 CELLS TREATED FOR 2 HOURS WITH
2 μM OF COMPOUND 3 OR COMPOUND 9 INHIBITORS

| Hours in Drug-Free Media | Compound 3 % of Control Autophosphorylation | Compound 9 % of Control Autophosphorylation |
|---|---|---|
| 0 | 0 | 4 |
| 4 | 12 | 24 |
| 8 | 23 | 100 |
| 23 | 54 | 100 |

TABLE 4

EFFECT OF EXAMPLE 3 ON INHIBITION OF
DIFFERENT TYROSINE KINASES IC$_{50}$ (nM)

| EGFR | C-SRC | Insulin | PDGF | FGF1 |
|---|---|---|---|---|
| 0.36 | >2,500 | >50,000 | >50,000 | >50,000 |

In Vivo Data

Female nude mice (NCr nu/nu, Taconic Farms) 18–20 g were implanted SC with tumor fragments (approximately 30 mg) in the region of the right axilla on Day 0. The tumor used in this study was an NIH 3T3 fibroblast transfected with the h-EGF receptor (Decker, et al., *J Biol Chem*, 1990;265:7009–7015). This model is very tumorigenic, producing a 100% take rate, and doubles in volume in less than 2 days. The compound of Example 3 was administered intraperitoneally every 12 hours on Days 3 through 7 for a total of 10 injections (5 mice per group). The vehicle was 6% dimethyl acetamide in 50 mM lactate buffer, pH 4.0. Tumor volumes were recorded three times per week by measuring the length and width of the individual tumors and calculating the mass in milligrams according to the formula (a×b$^2$)/2, where a and b are the length and width of the tumor. Percent T/C (treated/control) was calculated based on the ratio of the median tumor volume of the treated tumors compared with the median tumor volume of the control tumors on specified measurement days.

Treatment at both 100 and 30 mg/kg/injection inhibited tumor growth by 40% to 50% as assessed on Days 7, 10, and 12 of the experiment. No activity was observed at 10 or 3 mg/kg/injection. No weight loss, lethality, or clinical signs of toxicity were observed at any dose level.

| | % T/C | | |
|---|---|---|---|
| | Day | | |
| Group | 7 | 10 | 12 |
| Control | 100 | 100 | 100 |
| Example No. 3 @ 100 (mg/kg/injection) | 57 | 70 | 57 |
| Example No. 3 @ 30 (mg/kg/injection) | 48 | 66 | 53 |
| Example No. 3 @ 3 (mg/kg/injection) | 115 | 138 | 113 |

Additional In Vivo Testing

Using a similar protocol to that described above, with the exception that six mice per group are used, and the dosing schedules are as described, several compounds have been tested against a variety of tumor xenografts, These include the h-EGF receptor transfected NIH 3T3-transfected fibroblast model described above; the A431 human epidermoid carcinoma, which heavily overexpresses the EGF receptor; the MCF7 human breast carcinoma, which is sensitive to EGF receptor inhibitors and known to express the EGF receptor and erbB-2 and erbB-3; the SK-OV-3 human ovarian carcinoma, which greatly overexpresses erbB-2: the AH-125 small cell lung cancer which overexpresses the EGF receptor; and the murine 16/c mammary adenocarcinoma.

Example 3

EGFR Tumor

IP dosing bid Days 3 through 7:

@100 mg/kg produced 4 day growth delay.
@30 mg/kg produced 2.5 day growth delay.
IP dosing bid Days 1 through 13:
@300 mg/kg no activity.
@190 and 120 mg/kg 1 day growth delay.
@75 mg/kg 5 day growth delay.

Example 11

MCF-7 Tumor

IP dosing bid Days 1–5, 8–12, 15–19:

@47 mg/kg 17.4 day growth delay.
@28 mg/kg 22.9 day growth delay.
Murine 16/c Mammary Adenocarcinoma
Inactive at doses of up to 120 mg/kg bid.
EGFR Tumor
IP dosing bid for 14 days:
@75 mg/kg produced 8.7 day growth delay.
@47 mg/kg 6.6 day growth delay.
@29 mg/kg 2.3 day growth delay.
@18 mg/kg 1.8 day growth delay.
@150 mg/kg toxic.
@75 mg/kg toxic.
IP dosing bid Days 3–7, 10–14, 17–21, 24–28:
@75 mg/kg 19.9 day growth delay.
@150 mg/kg toxic.
IP dosing once daily Days 3–17:
@75 mg/kg 11.7 day growth delay.

IP dosing once daily Days 3–7, 10–14, 17–21:
@75 mg/kg 5.3 day growth delay.
@150 mg/kg toxic.
A431 Tumor
IP dosing bid Days 7–11, 4–18, 21–25:
@28 mg/kg produced a 28.2 day growth delay.
PO dosing once daily Days 7–21:
@200 mg/kg produced a 3.5 day growth delay.
@100 mg/kg a 2 day growth delay.
SK-OV-3 Tumor
ID dosing bid Days 10–14, 17–21, 24–28:
@30 mg/kg produced 1.2 day growth delay.

Example 19

EGFR Tumor
IP dosing bid for 14 days:
@124 mg/kg produced 11.8 day growth delay.
@77 mg/kg 7.9 day growth delay.
@48 mg/kg 6.4 day growth delay.
@200 mg/kg toxic.
SK-OV-3 Tumor
ID dosing bid Days 10–14, 17–21, 24–28:
@30 mg/kg produced 1.3 day growth delay.
A431 Tumor
SC-Infusion (Alzet) Days 9–23:
@24 mg/kg/day produced a 14 day growth delay.
@12 mg/kg/day produced a 15 day growth delay.

Example 21

IP dosing bid:
@48 mg/kg toxic.
EGFR Tumor
IP dosing bid for 14 days:
@12.5 mg/kg produced 16.8 day growth delay.
@6.25 mg/kg 9.3 day growth delay.
@25 mg/kg toxic.
SC-Infusion (Alzet):
@200, 124, 77, and 48 mg/kg/day toxic.
AH-125 Tumor
SC-Infusion (Alzet) Days 19–33:
@20.6 mg/kg/day produced a 10.0 day growth delay.
@10.4 mg/kg/day produced a 9.5 day growth delay.
@5.5 mg/kg/day produced a 9.5 day growth delay.
A431 Tumor
SC-Infusion (Alzet) Days 9–23, 42–56:
@48 mg/kg/day produced a 55 day growth delay.
@24 mg/kg/day produced a 60 day growth delay.
@12 mg/kg/day produced a 51 day growth delay.

Example 36

EGFR Tumor
IP dosing bid for 7 days:
@48 mg/kg produced 10.3 day growth delay.
IP dosing bid for 14 days:
@25 mg/kg produced 8.7 day growth delay
@12.5 mg/kg 3.5 growth delay.
@50 mg/kg toxic.
SC-Infusion (Alzet):
@200, 124, 77 mg/kg/day toxic.

Example 40

IP dosing bid:
@48 and 20 mg/kg toxic.
EGFR Tumor
Inefficacious @10 and 5 mg/kg bid for 14 days.
SC-Infusion (Alzet):
@200, 124, 77, and 48 mg/kg/day toxic.

What is claimed is:
1. A compound having the formula I

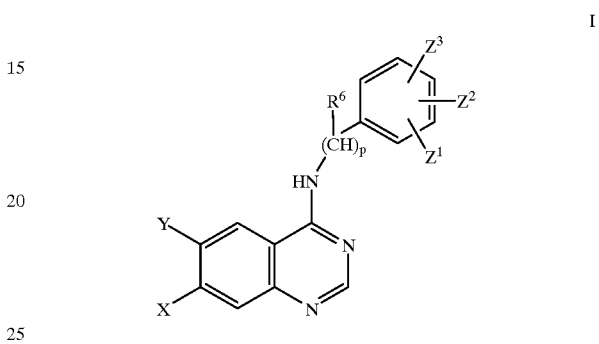

wherein X is —O(CH$_2$)$_n$morpholino, and Y is —D—E—F;

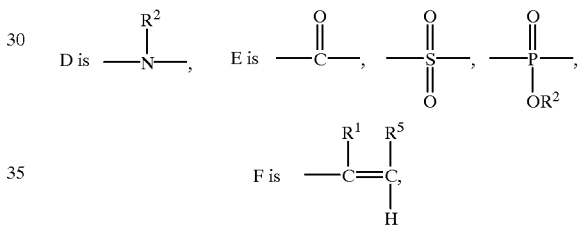

R$^1$ is hydrogen, halogen, or C$_1$–C$_6$ alkyl;
R$^2$, R$^3$, and R$^4$ are independently hydrogen, C$_1$–C$_6$ alkyl, —(CH$_2$)$_n$-N-piperidinyl, —(CH$_2$)$_n$-N-piperazinyl, —(CH$_2$)$_n$-N$_1$-piperazinyl, —(CH$_2$)$_n$-N-pyrrolidyl, —(CH$_2$)$_n$-pyridinyl, —(CH$_2$)$_n$-N-imidazoyl, —(CH$_2$)$_n$-imidazoyl, —(CH$_2$)$_n$-N-morpholino, —(CH$_2$)$_n$-N-thiomorpholino, —(CH$_2$)$_n$-N-hexahydroazepine or substituted C$_1$–C$_6$ alkyl, wherein the substituents are selected from —OH, —NH$_2$, or

A and B are independently hydrogen, C$_1$–C$_6$ alkyl, —(CH$_2$)$_n$OH, —(CH$_2$)$_n$-N-piperidinyl, —(CH$_2$)$_n$-N-piperazinyl, —(CH$_2$)$_n$-N$_1$-piperazinyl, —(CH$_2$)-N-pyrrolidyl, —(CH$_2$)$_n$-N-pyridyl, —(CH$_2$)$_n$-imidazoyl or —(CH$_2$)$_n$-N-imidazoyl;
Z$^1$, Z$^2$, or Z$^3$ are independently hydrogen, halogen, C$_1$–C$_6$ alkyl, C$_3$–C$_8$ cycloalkyl, C$_1$–C$_6$ alkoxy, C$_3$–C$_8$ cycloalkoxy, nitro, C$_1$–C$_6$ perfluoroalkyl, hydroxy, C$_1$–C$_6$ acyloxy, —NH$_2$, —NH(C$_1$–C$_6$ alkyl), —N(C$_1$–C$_6$ alkyl)$_2$, —NH(C$_3$–C$_8$cycloalkyl), —N(C$_3$–C$_8$ cycloalkyl)$_2$, hydroxymethyl, C$_1$–C$_6$ acyl, cyano, azido, C$_1$–C$_6$ thioalkyl, C$_1$–C$_6$ sulfinylalkyl, C$_1$–C$_6$ sulfonylalkyl, C$_3$–C$_8$ thiocycloalkyl, C$_3$–C$_8$ sulfinylcycloalkyl, $C_3$–$C_8$ sulfonylcycloalkyl, mercapto, $C_1$–$C_6$ alkoxycarbonyl, $C_3$–$C_8$ cycloalkoxycarbonyl, $C_2$–$C_4$ alkenyl, $C_4$–$C_8$ cycloalkenyl, or $C_2$–$C_4$ alkynyl; and $R^5$ is hydrogen, halogen, $C_1$–$C_6$-perfluoroalkyl, 1,1-difluoro($C_1$–$C_6$)alkyl, $C_1$–$C_6$alkyl, —($CH_2$)$_n$-N-piperidinyl, —($CH_2$)$_n$-piperazinyl, —($CH_2$)$_n$-piperazinyl, —($CH_2$)$_n$-N-pyrrolidyl, —($CH_2$)$_n$-pyridinyl, —($CH_2$)$_n$-N-imidazoyl, —($CH_2$)$_n$-N-morpholino, —($CH_2$)$_n$-N-thiomorpholino,

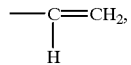

—CH=CH—($C_1$–$C_6$)alkyl, —($CH_2$)$_n$-N-hexahydroazepine, —($CH_2$)$_n$NH$_2$, —($CH_2$)$_n$NH($C_1$–$C_6$ alkyl), —($CH_2$)$_n$N($C_1$–$C_6$ alkyl)$_2$, -1-oxo($C_1$–$C_6$)alkyl, carboxy, ($C_1$–$C_6$)alkyloxycarbonyl, N-($C_1$–$C_6$)alkylcarbamoyl, phenyl or substituted phenyl, wherein the substituted phenyl can have from one to three substituents independently selected from $Z^1$, $Z^2$, $Z^3$ or a monocyclic heteroaryl group, and each $C_1$–$C_6$ alkyl group can be substituted with —OH, —NH$_2$ or —NAB, where A and B are as defined above, $R^6$ is hydrogen or $C_1$–$C_6$ alkyl; and n is 1 to 4, p is 0 or 1, and the pharmaceutically acceptable salts, esters, amides, and prodrugs thereof.

2. A compound of claim 1 wherein $Z^1$ and $Z^2$ are hydrogen, and $Z^3$ is a halogen.

3. A compound of claim 2 wherein $Z^3$ is bromine.

4. A compound of claim 3 wherein the bromine is located at the 3 or meta position of the phenyl ring.

5. A compound of claim 1 wherein $Z^1$ is hydrogen, $Z^2$ is fluorine, and $Z^3$ is chlorine.

6. A compound of claim 5 wherein the fluorine is located at the 4 position and the chlorine is located at the 3 position of the phenyl ring.

7. A compound of claim 1 wherein $R^2$ is hydrogen.

8. A compound of claim 1 wherein $R^2$ is —$CH_2$)$_n$-morpholino.

9. A compound of claim 1 wherein $R^5$ is carboxy, ($C_1$–$C_6$) alkyloxycarbonyl or $C_1$–$C_6$ alkyl.

10. A pharmaceutically acceptable composition that comprises a compound of claim 1.

11. A method of treating cancer, the method comprising administering to a patient having cancer a therapeutically effective amount of a compound of claim 1.

12. A method of treating restenosis, the method comprising administering to a patient having restenosis a therapeutically effective amount of a compound of claim 1.

13. A method of irreversibly inhibiting tyrosine kinases, the method comprising administering to a patient a tyrosine kinase inhibition a tyrosine kinase inhibiting amount of a compound of claim 1.

14. A method of treating psoriasis, the method comprising administering to a patient having psoriasis a therapeutically effective amount of a compound of claim 1.

15. A method of treating atherosclerosis, the method comprising administering to a patient having atherosclerosis a therapeutically effective amount of a compound of claim 1.

16. A method of treating endometriosis, the method comprising administering to a patient having endometriosis a therapeutically effective amount of a compound of claim 1.

17. A compound according to claim 1 wherein the compound is selected from the group consisting of N-[4-[(3-Bromophenyl)amino]-7-[3-(4-morpholino) propoxy]quinazolin-6-yl]acrylamide; and;

N-[4-[(3-Methylphenyl)amino]-7-[3-(4-morpholino) propoxy]quinazolin-6-yl]acrylamide.

* * * * *

UNITED STATES PATENT AND TRADEMARK OFFICE
CERTIFICATE OF CORRECTION

PATENT NO.    : 6,344,459 B1
DATED         : February 5, 2002
INVENTOR(S)   : Alexander James Bridges et al.

It is certified that error appears in the above-identified patent and that said Letters Patent is hereby corrected as shown below:

Column 92,
Line 27, "-O(CH2)nmrphonlino," should read -- -O(CH2)nmrphonlino or hydrogen, --.
Lines 43 and 57, "-(CH2)n-N1-piperazinyl," should read
-- -(CH2)n-N1-piperazinyl[N4-(C1-C6)alkyl] --.

Column 93,
Line 8, "piperazinyl," should read -- piperazinyl[N4-(C1-C6)alkyl] --.

Signed and Sealed this

First Day of July, 2003

JAMES E. ROGAN
*Director of the United States Patent and Trademark Office*